(12) United States Patent
Horvath et al.

(10) Patent No.: US 12,350,198 B2
(45) Date of Patent: Jul. 8, 2025

(54) SYSTEMS FOR LASER EYE SURGERY

(71) Applicant: Lensar, Inc., Orlando, FL (US)

(72) Inventors: Christopher Horvath, San Juan Capsitrano, CA (US); Vanessa Isabella Vera, San Juan Capistrano, CA (US)

(73) Assignee: Lensar, Inc., Orlando, FL (US)

( * ) Notice: Subject to any disclaimer, the term of this patent is extended or adjusted under 35 U.S.C. 154(b) by 0 days.

(21) Appl. No.: 15/718,125

(22) Filed: Sep. 28, 2017

(65) Prior Publication Data

US 2018/0085257 A1 Mar. 29, 2018

Related U.S. Application Data

(60) Provisional application No. 62/400,629, filed on Sep. 28, 2016.

(51) Int. Cl.
| | |
|---|---|
| *A61F 9/00* | (2006.01) |
| *A61B 17/02* | (2006.01) |
| *A61F 9/008* | (2006.01) |
| *A61B 3/13* | (2006.01) |
| *A61B 90/25* | (2016.01) |
| *A61B 90/98* | (2016.01) |
| *A61F 9/009* | (2006.01) |

(52) U.S. Cl.
CPC ...... *A61F 9/00834* (2013.01); *A61B 17/0231* (2013.01); *A61B 3/13* (2013.01); *A61B 90/25* (2016.02); *A61B 90/98* (2016.02); *A61F 9/0084* (2013.01); *A61F 2009/00846* (2013.01); *A61F 2009/00851* (2013.01); *A61F 2009/00889* (2013.01); *A61F 9/009* (2013.01)

(58) Field of Classification Search
CPC .............. A61F 9/00821; A61F 9/00823; A61F 9/0084; A61F 9/00834; A61F 9/00754; A61F 2009/00889; A61F 2009/00745; A61F 2009/00821; A61F 2009/00825
See application file for complete search history.

(56) References Cited

U.S. PATENT DOCUMENTS

| | | | | |
|---|---|---|---|---|
| 4,503,854 A | * | 3/1985 | Jako ...................... | A61B 18/20 348/65 |
| 4,729,373 A | | 3/1988 | Peyman | |
| 4,825,865 A | | 5/1989 | Zelman | |
| 4,946,452 A | | 8/1990 | Py | |
| 5,057,098 A | | 10/1991 | Zelman | |
| 5,098,426 A | | 3/1992 | Sklar | |

(Continued)

FOREIGN PATENT DOCUMENTS

| | | |
|---|---|---|
| CN | 2315667 Y | 1/2001 |
| DE | 10 2011 16 368 | 4/2023 |

(Continued)

OTHER PUBLICATIONS

Jul. 7, 2021, WIPO, PCT/US21/12008—Opinin and search report.

(Continued)

*Primary Examiner* — Sana Sahand
(74) *Attorney, Agent, or Firm* — Belvis Law, LLC.; Glen P. Belvis

(57) ABSTRACT

Methods and system for improved laser eye surgery using photodisruptive laser pulses. A system for moving a femtosecond laser delivery head in a horizontal direction from a retracted position to an extended position over a patient.

24 Claims, 65 Drawing Sheets

(56) References Cited

U.S. PATENT DOCUMENTS

| | | |
|---|---|---|
| 5,139,504 A | 8/1992 | Zelman |
| 5,423,801 A | 6/1995 | Marshall |
| 5,548,352 A | 8/1996 | Dewey |
| 5,591,160 A | 1/1997 | Reynard |
| 5,651,783 A | 7/1997 | Reynard |
| 5,695,461 A | 12/1997 | Schaible |
| 5,722,970 A | 3/1998 | Colvard et al. |
| 5,741,244 A | 4/1998 | Klaas |
| 6,045,527 A | 4/2000 | Appelbaum |
| 6,391,020 B1 | 5/2002 | Kurtz |
| 6,544,254 B1 | 4/2003 | Bath |
| 6,607,527 B1 | 8/2003 | Ruiz |
| 6,733,491 B2 | 5/2004 | Kadziauskas |
| 6,736,360 B1 | 5/2004 | Buczek |
| 6,962,583 B2 | 11/2005 | Kadziauskas |
| 7,130,835 B2 | 10/2006 | Cox |
| 7,182,759 B2 | 2/2007 | Kadziauskas |
| 8,986,290 B2 | 3/2015 | Patton |
| 9,050,171 B2 | 6/2015 | Foster |
| 9,095,415 B2 | 8/2015 | Blumenkranz et al. |
| 9,107,732 B2 | 8/2015 | Blumenkranz et al. |
| 9,259,354 B2 | 2/2016 | Horvath |
| 9,492,318 B2 | 11/2016 | Rockley et al. |
| 10,709,610 B2 | 7/2020 | Morley et al. |
| 2001/0035702 A1 | 11/2001 | Murphy |
| 2003/0050629 A1 | 3/2003 | Kadziauskas |
| 2003/0073984 A1 | 4/2003 | Maeda |
| 2004/0034340 A1 | 2/2004 | Biscup |
| 2006/0200068 A1 | 9/2006 | Kadziauskas |
| 2007/0027470 A1 | 2/2007 | Dodick |
| 2007/0161972 A1 | 7/2007 | Felberg |
| 2007/0237620 A1 | 10/2007 | Muhlhoff |
| 2008/0004608 A1 | 1/2008 | Dacquay |
| 2008/0013048 A1 | 1/2008 | Gaida |
| 2008/0071254 A1 | 3/2008 | Lummis |
| 2008/0103367 A1 | 5/2008 | Burba |
| 2009/0049522 A1 | 2/2009 | Claus |
| 2009/0137991 A1 | 5/2009 | Kurtz |
| 2009/0149841 A1* | 6/2009 | Kurtz .................. A61B 18/20 606/4 |
| 2009/0247999 A1 | 10/2009 | Tuan |
| 2009/0271155 A1 | 10/2009 | Dupps |
| 2010/0042081 A1 | 2/2010 | Rathjen |
| 2010/0191100 A1 | 6/2010 | Anderson |
| 2011/0022035 A1 | 1/2011 | Porter |
| 2011/0196350 A1* | 8/2011 | Friedman ................ A61F 9/008 606/6 |
| 2011/0288470 A1 | 11/2011 | Boukhny |
| 2012/0022510 A1 | 1/2012 | Welches |
| 2012/0316544 A1* | 12/2012 | Horvath .............. A61F 9/00825 606/6 |
| 2012/0330290 A1* | 12/2012 | Gray ........................ A61F 9/008 606/4 |
| 2013/0023864 A1 | 1/2013 | Blumenkranz |
| 2013/0072917 A1* | 3/2013 | Kaschke ............. A61F 9/00736 606/6 |
| 2013/0090636 A1 | 4/2013 | Patton |
| 2013/0150836 A1* | 6/2013 | Bor .......................... A61B 3/14 606/4 |
| 2013/0237970 A1* | 9/2013 | Summers ............ A61F 9/00827 606/5 |
| 2014/0046308 A1 | 2/2014 | Bischoff |
| 2014/0052113 A1 | 2/2014 | Kuehnert |
| 2014/0104576 A1 | 4/2014 | Bor et al. |
| 2014/0107634 A1* | 4/2014 | Vogler ................ A61F 9/00825 606/6 |
| 2014/0364870 A1 | 12/2014 | Alvarez et al. |
| 2015/0190281 A1 | 6/2015 | Patton |
| 2015/0255004 A1 | 9/2015 | Manzke |
| 2016/0045367 A1* | 2/2016 | Horvath .............. A61F 9/00825 606/6 |
| 2016/0089269 A1 | 3/2016 | Horvath |
| 2016/0302915 A1 | 10/2016 | Sayegh |
| 2017/0000645 A1 | 1/2017 | Alvarez et al. |
| 2017/0000647 A1 | 1/2017 | Schuele et al. |
| 2017/0056245 A1 | 3/2017 | Rockley et al. |
| 2017/0119249 A1 | 5/2017 | Gunn |
| 2017/0119578 A1 | 5/2017 | Rockley et al. |
| 2017/0290703 A1 | 10/2017 | Teuma et al. |
| 2017/0340483 A1 | 11/2017 | Rill et al. |
| 2018/0028355 A1 | 2/2018 | Raksi |
| 2018/0055581 A1 | 3/2018 | Papac |
| 2018/0085256 A1 | 3/2018 | Gray et al. |
| 2018/0161051 A1 | 6/2018 | Humayun |
| 2018/0168547 A1 | 6/2018 | Kim |
| 2018/0168859 A1 | 6/2018 | Bischoff et al. |
| 2018/0185043 A1 | 7/2018 | Humayun |
| 2018/0206717 A1 | 7/2018 | Ramesh Kumar et al. |
| 2018/0250090 A1 | 9/2018 | Patton |
| 2018/0263813 A1 | 9/2018 | Teuma |
| 2019/0015252 A1 | 1/2019 | Lake |
| 2019/0083304 A1 | 3/2019 | Patton |
| 2019/0083308 A1 | 3/2019 | Rathjen |
| 2019/0096933 A1 | 3/2019 | Kido et al. |
| 2019/0298473 A1 | 10/2019 | Hillas et al. |
| 2019/0365567 A1 | 12/2019 | Balkenbush et al. |
| 2020/0258599 A1 | 8/2020 | Clark |
| 2021/0259880 A1 | 8/2021 | Newton et al. |
| 2021/0259881 A1 | 8/2021 | Gray et al. |
| 2021/0298955 A1 | 9/2021 | McWhirter et al. |
| 2021/0378864 A1 | 12/2021 | Teuma et al. |

FOREIGN PATENT DOCUMENTS

| | | |
|---|---|---|
| EP | 2057973 | 5/2009 |
| EP | 2 459 143 | 4/2018 |
| JP | 2015 029641 | 2/2015 |
| KR | 10-2015-0128049 | 11/2015 |
| WO | WO1992017138 | 10/1992 |
| WO | WO1997022304 | 6/1997 |
| WO | WO1998012973 | 4/1998 |
| WO | WO 1999065405 | 12/1999 |
| WO | WO2006074469 | 7/2006 |
| WO | WO2009039315 | 3/2009 |
| WO | WO2009061758 | 5/2009 |
| WO | WO 2011/147570 | 12/2011 |
| WO | WO2012047492 | 4/2012 |
| WO | WO 2012/135073 | 10/2012 |
| WO | WO 2012/152496 | 11/2012 |
| WO | WO 2013057098 | 4/2013 |
| WO | WO2013126653 | 8/2013 |
| WO | WO2014201165 | 12/2014 |
| WO | WO 2016/058931 | 4/2016 |
| WO | WO 2017/153442 | 9/2017 |
| WO | WO 2018/025169 | 2/2018 |

OTHER PUBLICATIONS

Apr. 6, 2021, WIPO, PCT/US21/12009—Opinin and search report.
May 25, 2021, WIPO, PCT/US21/12010—Opinin and search report.
Jun. 25, 2021, WIPO, PCT/US21/12011—Opinin and search report.

* cited by examiner

FRIG 36

SYSTEMS FOR LASER EYE SURGERY

The present non-provisional application claims the benefit of priority under 35 U.S.C. § 119(e) of U.S. provisional application No. 62/400,629 filed on Sep. 28, 2016, the entire content of which is incorporated herein by reference.

BACKGROUND OF THE INVENTION

The present invention generally relates to systems, apparatus, and methods related to surgery and micromachining. More particularly, the present invention relates to systems, apparatus and methods for eye surgery. Eye surgery and particularly Cataract surgery is one of the most common surgical procedures performed. The primary goal of cataract surgery is the removal of the defective lens and replacement with an artificial lens or intraocular lens (IOL) that restores some of the optical properties of the defective lens.

The major steps in cataract surgery consist of making cornea incisions to allow access to the anterior chamber of the eye and to correct for astigmatism (Limbal relaxing incisions, LRIs), cutting and opening the capsule of the lens to gain access to the lens, fragmenting and removing of the lens and in most cases placing an artificial intraocular lens in the eye.

The cornea incisions are typically performed with surgical knives or more recently with lasers.

Cutting of the capsule is most commonly done through skillful mechanical cutting and tearing a circle shaped opening, using hand tools. This procedure is called capsulorhexis.

Traditional methods for performing a capsulorhexis are based on mechanical cut and peeling techniques. Another method referred to as YAG laser anterior capsulotomy delivers individual laser pulses with high energy to the eye to assist with the opening of the capsule. The precision and quality of these methods is limited.

More recently, photodisruptive (also referred to as plasma mediated ablation) lasers and methods have been introduced that can perform incisions inside the eye with great precision. There is also another class of femtosecond lasers-tissue interaction that work below the optical (photodisruptive) breakdown threshold and destroy or rather decompose the tissue in the focus zone through a so called photochemical induced decomposition and thermoelastic disruption; see "Vogel A, et al. Mechanism of femtosecond laser nanosurgery of cells and tissues. Applied Physics B, 2005; 81:1015-1047". This class of lasers used for that is typically a high powered femto second oscillator, which creates high pulse rates in the order of 10 MHz and relatively small pulse energies in the order of 10 nJ to 800 nJ. These systems are also sometimes referred to as subthreshold femto laser. These laser pulses are focus to a very small spot size typically <2 um diameter. From here on in this disclosure any reference to a femto laser shall include all versions and types of femto second laser systems and pulses as described above and below. The inventor's prior patents and patent applications regarding photo disruptive lasers for use in eye surgery include: US 6/992.765, US 7/371.230, US 61/619, U.S. Ser. No. 12/902,105, and PCT/US11/54506. Photo disruptive laser pulses in the range of <20000 femtoseconds (<20 pico seconds) have been successfully applied to make incisions into various tissues of the eye. The main focus to date has been using a femtosecond laser for various cornea incisions such as LASIK flaps, intrastromal incisions, Limbal Relaxing Incisions, Keratoplasties and cornea entry incisions. In more recent years femtosecond lasers have also been successfully applied to the capsule and inside of the lens of the human eye using femtosecond laser assisted cataract procedures. Furthermore weakening of the lens material through controlled femtosecond laser exposure inside the natural human lens shows promise to treat presbyopia which is mainly a condition of a stiffening lens that loses range of accommodation.

The main benefit of these photodisruptive or subthreshold laser pulses lays in the fact that the eye tissues that are treated transmit the wavelengths of the typically chosen lasers, usually in the near infrared or visible range and therefore allow the laser to be focused through the cornea, aqueous humor, lens capsule and lens without much scattering or absorption. The laser pulses are always focused to a very small spot size in the range of 0.3 to 10 micrometers, so that a laser induced optical breakdown or a subthreshold effect is achieved in any tissue or liquid (e.g. aqueous humor) that falls within the spot size location.

The optical breakdown (photodisruptive breakdown) creates a micro plasma followed by a small cavitation bubble. This photodisruption of tissue can be used to cut and dissect tissue areas of any size and shapes by scanning a sequence of many such laser pulses over a desired volume in the eye.

Subthreshold laser pulses that achieve photochemical induced decomposition and thermoelastic disruption shall from here onto also be included in the term optical breakdown.

Since the tissue layers in the laser path above and below the focus point are below the optical breakdown threshold and since they don't significantly absorb the laser wavelength, they remain unaffected by the laser beam. This principle allows non-invasive photo disruptive eye surgery since no incision from the outside needs to be made.

There is a threshold of a minimum laser fluence (laser peak power divided by focus area) required to achieve the optical breakdown. The laser peak power goes up with higher pulse energy (typically in the µJ range) and shorter pulse duration (typically <600 fs). The laser fluence for any given peak power goes up as the focus area goes down. Achieving a small spot size is therefore critical in achieving a high fluence that exceeds the optical breakdown threshold.

The way of achieving a high enough fluence for breakdown by increasing the laser pulse energy is less desirable since a higher pulse energy comes with a larger cavitation bubble and associated shock wave. The larger the cavitation bubble the less precision is achieved in cutting any features with a sequence of pulses. Furthermore, a large shock wave is considered a undesired side effect since it has the potential to damage surrounding tissues.

Priority is therefore given to minimizing the spot size to achieve an above threshold laser fluence while using laser pulses within a low pulse energy range of typically <50 µJ or even <1 µJ for the subthreshold effect per laser pulse. These principles have been successfully implemented in femtosecond eye laser systems treating the cornea or capsule/lens of an eye. Typical laser beam focusing convergence angles required are numerical apertures of NA >0.15 (full angle $\Theta$>15 deg) and in some optimized cases NA >0.3 or even NA >0.6 to get into the range of a 1 um spot size or smaller using a wavelength around 1 um.

According to:

$$\omega_0 = M^2 \frac{360\lambda}{\pi^2 \Theta} \qquad \text{Formula 1}$$

Θ=full focusing convergence angle in degrees
λ=laser wavelength
$\omega_0$=laser beam focus radius defined by $1/e^2$ cut off
$M^2$=beam quality factor determined by the total aberrations If beam aberrations can be kept to a minimum e.g. $M^2<1.3$ ($M^2=1$ is the theoretical minimum with no aberration at all) then the above focusing angles of NA>0.15 (Θ>15 deg) and NA>0.30 (Θ>30 deg) the resulting spot size diameters (2 $\omega_0$) will be <8 um and <4 um respectively (for a laser wavelength λ=1 um). Higher NA numbers and high peak power self focusing effects near the laser focus result in further reduced laser spot sizes down to 2 um or even smaller The high numerical aperture and minimization of aberrations is critical in achieving such small spot sizes. The laser delivery systems for such laser parameters face several challenges due to the high numerical aperture required for to achieve a very small spot size. These systems get further complicated by using a laser beam that is scanned through the focusing lens assembly. Maintaining low aberration while scanning a laser beam at an incidence angle other than normal (90 degrees of incidence) through a lens that creates a high numerical aperture focused beam, requires a complex system of multiple lenses in a precise arrangement. Additionally, those methods and systems require a patient interface such as an applanation lens to reference and fixate the eye to the laser system. Placement of this patient interface adds significant complexity to the surgical setup and can cause undesired or harmful high intraocular pressures levels for the duration of the laser procedure. The patient interface is typically provided sterile and is used only once therefore adding significant cost to the overall cataract procedure. Additionally, no current patient interface or laser delivery system that can perform the laser cornea incisions and laser capsulotomy is compatible or has been integrated with a standard surgical microscope. Since the cataract surgery requires a surgical operating microscope to be completed, the patient must be moved and repositioned under a surgical microscope after the current laser assisted parts of the procedure have been completed. This causes a significant time delay and logistical effort.

This invention describes various methods and systems to deliver laser pulses to the eye or any material. Its preferred embodiment is the delivery of a sequence of ultra short (<50000 femtosecond from now on referred here as (fs-femtosecond) laser pulses to achieve an optical breakdown inside the eye tissue at a small spot size (typically <10 micrometer in diameter). Other laser systems with longer pulse durations >1 ns and spot sizes >40 um are also described in inventions here. The here disclosed laser delivery system also dramatically reduces the delivery system size, complexity and induced beam aberrations. Furthermore, several novel delivery system integration designs are disclosed that allow a femtosecond laser treatment with or without a patient interface to be integrated with a standard surgical microscope. This application describes, among others, techniques, methods, apparatus and systems for laser based cornea incisions and capsule perforations (capsulotomy) to create an easier capsulorhexis procedure for both the anterior and posterior capsule, LRI cornea incisions as well as iris laser treatments and other laser applications. Implementation of the described techniques, apparatus and systems include: determining a surgical target region in the cornea and anterior capsule of the eye, and applying laser pulses to photo disrupt a portion of the determined target region to create an opening cut on a cornea or capsule of the lens.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 20 shows a laser delivery system out and in.

FIG. 43 shows a pig eye under the laser delivery system with the visible targeting laser beam on.

SUMMARY

Figure 23:
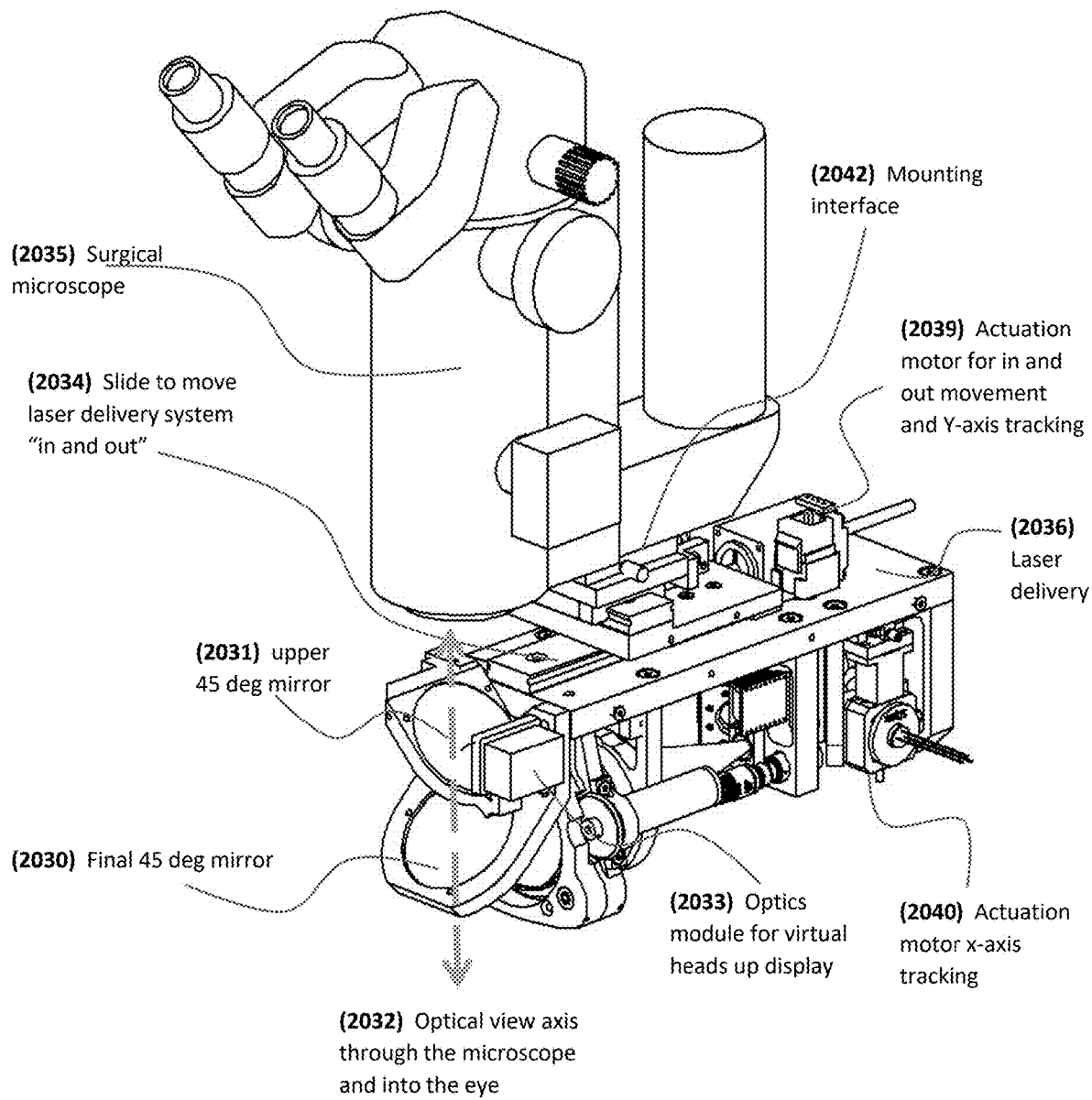
FIG. 23 shows a laser delivery system mounted under the microscope without skins.
Figure 52:
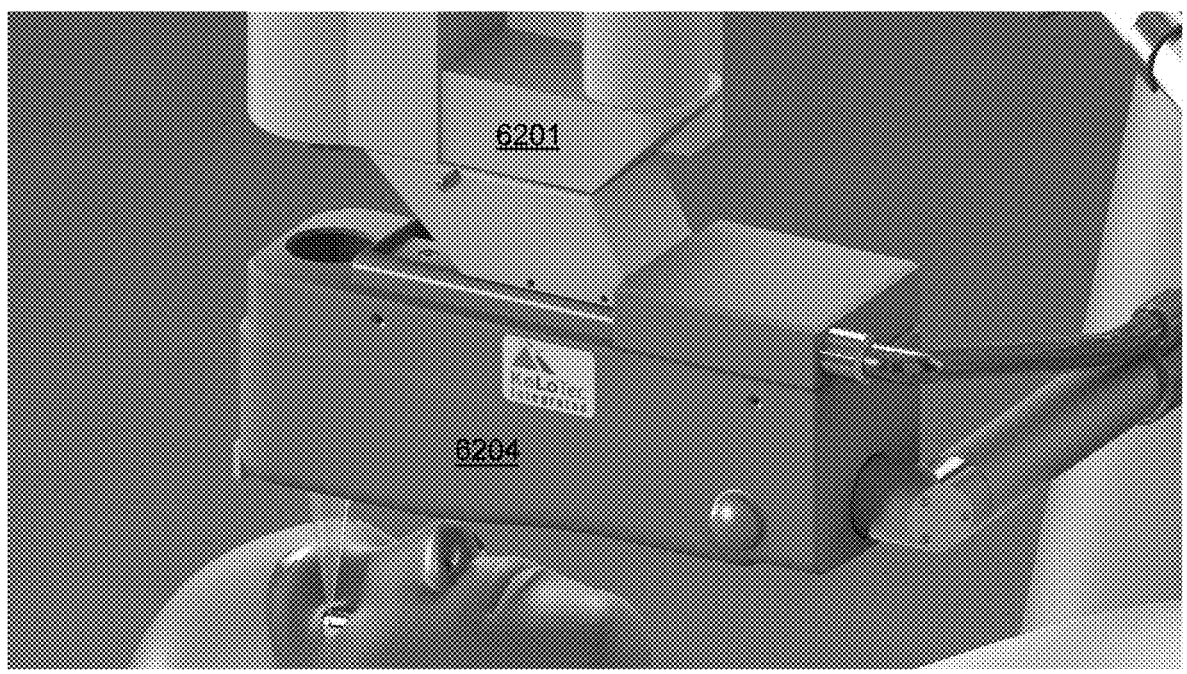
FIG. 52 shows a laser delivery system in the "in" position under the microscope.

The inventions here describe several delivery system configurations. One key invention is a delivery system that contains all scanning and focusing optics in its beam path before a final 45 deg routing mirror FIG. 23 (2030) that reflects the treatment laser beam by about a 90 degree angle towards the eye and in the same time allows a surgical microscope or slitlamp microscope to observe the eye tissue through a straight optical path (2032) from the eye through the 45 deg mirror and into the microscope (2035). Because there is no optics after the final 45 deg mirror (2030), this arrangement allows for effective integration of such a laser delivery system (2036) under a surgical microscope (2035) or integrated with a slitlamp microscope. FIG. 23 shows this final 45 deg mirror on the bottom left side of the picture (2030). In that FIG. 23 there is another optional 90 deg rotated 45 degree mirror (2031) above the final 45 deg mirror. This upper mirror (2031) is used to provide routing from a heads up display optics module (2032) that sits right next (front) of this upper mirror (2031). The surgical microscope view (2032) still goes now all the way vertical down through both mirrors (2031)+ (2030) (the upper mirror also has large vertical visible transmittance >40%) so that a life surgical view is still present through both 45 deg mirrors. The optics module (2033) (to the front right of the upper mirror) transmits an image upwards into the surgical microscope view through the upper 45 deg mirror. This upwards transmitted image adds to the optical view of the eye (2032) as an augmented reality overlap. The user can now see any visual signal, pattern, text, picture or graphics created by the optics module (2033) and visually overlapped to the surgical microscope view. FIG. 52 shows the same system as FIG. 23 except for in FIG. 23 the skins are removed and the 45 deg mirrors are now visible. The image in the optics module can be a single image (e.g. small display) or can be spatially separated double images (e.g. 2 small displays) that get routed separately through the dual channel microscope to create a 3D 3 dimensional virtual image for the observer (surgeon). Instead of a spatial separation of 2 image sources a single image source can be used that switches polarization in time (e.g 10-100 times per second) from one polarization state to an orthogonal polarization state. With the appropriate orthogonal polarizers build into the individual eye channels of a 3 D microscope the microscope now shows the observer a 3D virtual image from the heads up display overlaid to the already 3D optical straight through image. Alternatively, a heads up display optics module and 45 deg mirror can also be incorporated into the surgical microscope directly. Such a virtual image heads up display is here used to display a virtual capsule image showing to surgeon who looks into the microscope the exact position, tilt and orientation of the capsule and therefore the lens of the ye as well. The virtual image is overlaid over the real eye structure. The virtual image also contains information such as status and parameter updates of the laser system (e.g. colored laser ready indication, colored acceptability ranges for capsule tilt and eye targeting misalignment ranges). Numerical and textual information are also optionally displayed in the virtual heads up image. In another method and device, the virtual heads up image includes steering and alignment information such as e.g. colored arrows of different lengths indicating towards which direction the ye needs to be moved for optimal alignment and capsule tilt reduction. The surgeon gets informed and is guided by such virtual image visual guidance information to manually move the eye as described in other parts of this disclosure. Optionally the laser system is in a ready fire state while the surgeon follows the virtual image guidance and moves the eye manually towards the indicated desired position. When the system determines that the eye positioning is within the acceptable alignment range it will fire autonomously as long as the surgeon keeps the laser system in an enabled mode.

DESCRIPTION OF THE PREFERRED EMBODIMENTS

Figure 32:
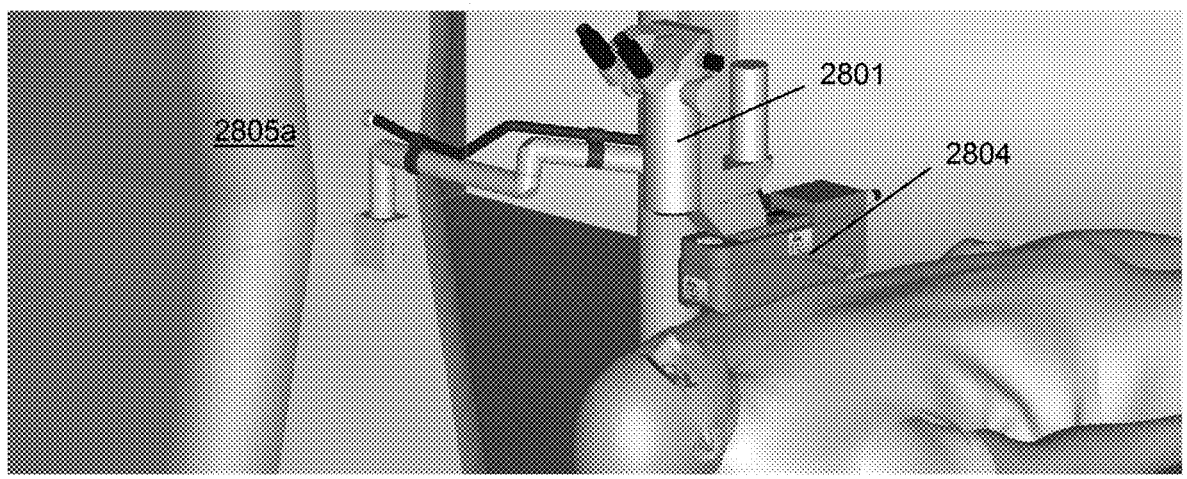
FIG. 32 shows same system as in FIG. 31 with the laser delivery system in the "out" position.
Figure 33:
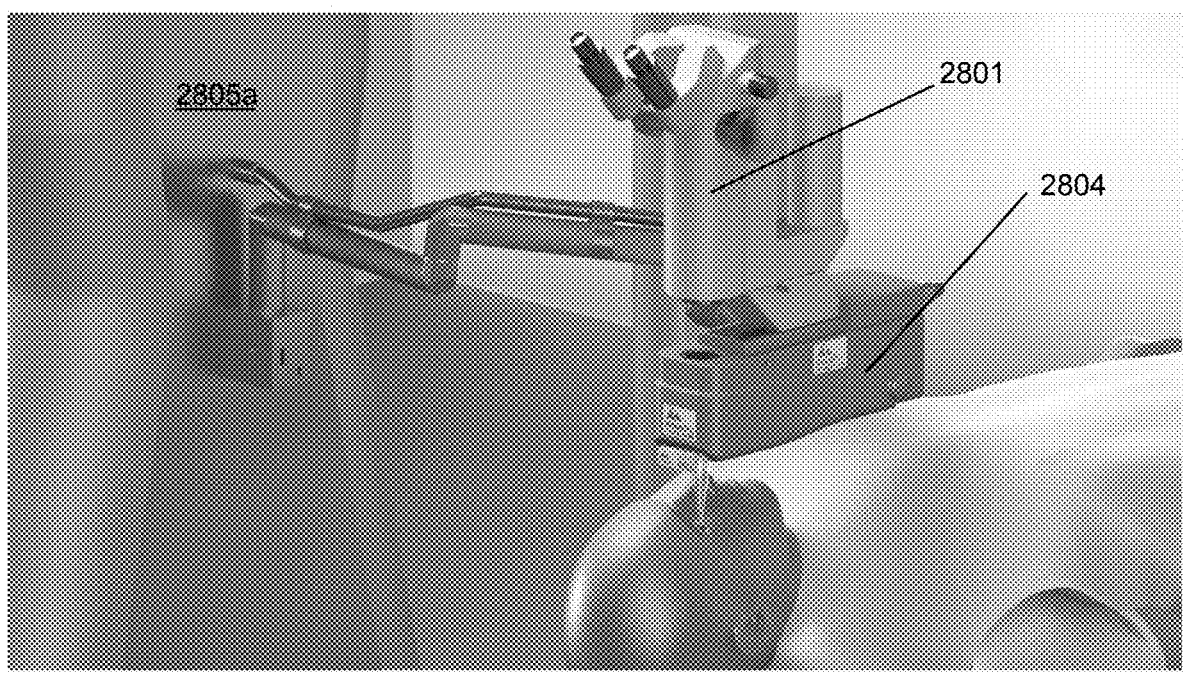
FIG. 33 shows a close up of FIG. 31.
Figure 53:
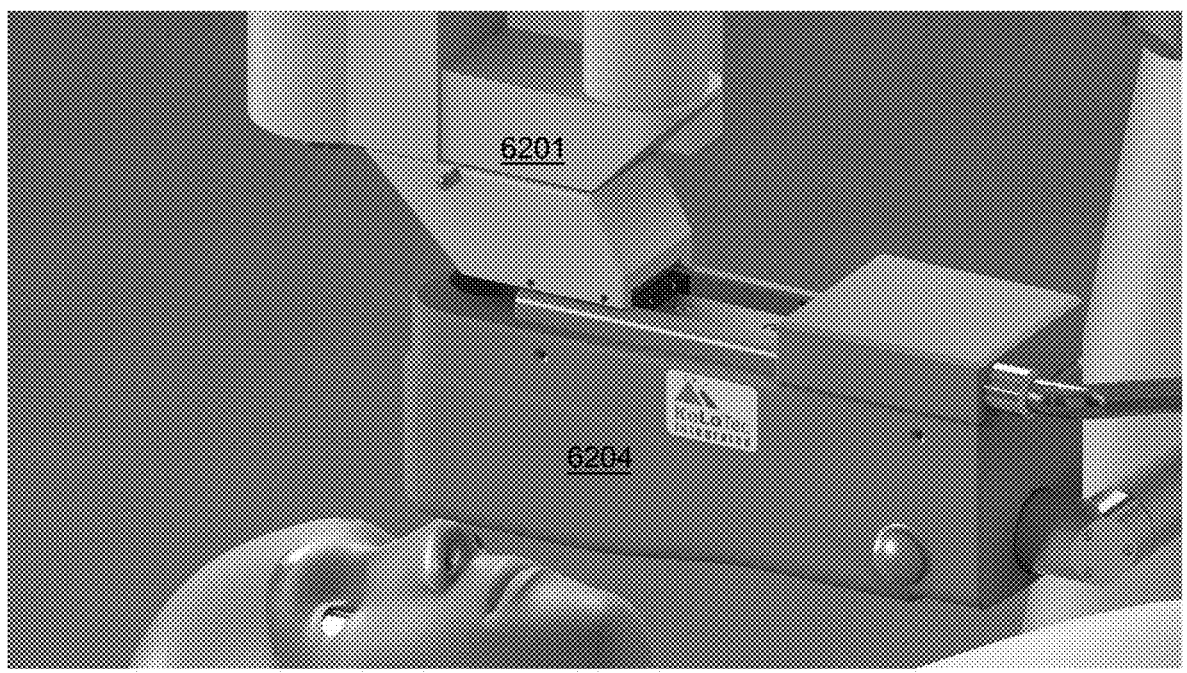
FIG. 53 shows a laser delivery system in the "out" position under the microscope.

Another system and method invention described here is a femtosecond laser delivery system that is mounted underneath a surgical microscope in a way that it can be moved in (engaged) and out (disengaged) of a laser firing position. The preferred in and out motion consist of a linear straight line. The engaged (in) position is shown in FIG. 52 and FIG. 33. The laser delivery system hangs here (is mounted) under the microscope in a position where the laser beam can be delivered into the eye and in the same time a opening on top of the laser delivery system allows the surgical microscope view going through the laser delivery system 45 deg mirror (inside the housing in these FIGURES) and into the eye. This position allows the laser being delivered to the eye while the surgeon still has full microscope view of the eye. The 45 deg mirror is has a optical coating that reflects a large amount (>90%) of the laser beam coming from the right here downwards to the eye while in the same time letting a large amount (>40%) of the visible spectrum light pass through the 45 deg mirror vertical up into the microscope and down into the eye. During the laser treatment the delivery system is ion this in (engaged) position. Before and after the laser treatment the system is in the out (disengaged) position as shown in FIG. 53 and FIG. 32. The system moves between the in and out position using a motorized translation stage as shown in FIG. 23 (here in the "in" position). FIG. 23 shows a actuation motor (2039) and a slide (2034) to move the delivery system in and out under the microscope (2035), and actuation motor (2040) x-axis tracking and a mounting interface (2042). When the delivery system is in the "out" (disengaged) position FIG. 53, the surgeon has full access to the patient's eye as if no laser delivery system were installed at all. This feature allows the surgeon to have full access to the eye to use his normal instrumentations such as a phaco hand piece, manual instruments, etc., When the laser delivery system is out the surgeon can continue or start any typical eye surgery. There is no space access impact. At any time during the eye surgery the surgeon can bring the laser delivery system to the "in" position FIG. 52, (preferably motorized as shown in FIG. 23 by the push of a button or by voice command) and perform any laser treatment procedure that the system supports. The baseline focusing plane of the laser delivery system is within +−2 mm adjusted such that it overlaps with the surgical microscope imaging focus. Therefore, when the laser delivery system is engaged (in position) the starting laser focusing point is close to the visual imaging (sharp) focusing plane. The laser delivery system may then scan the focusing depth (z-axis) from there up or downwards as required for the laser treatment or diagnostic procedure. This configuration and calibration allows the surgeon to move the laser delivery system in and out without much time or readjustment efforts. The motorized in and out motion takes between 1 second and 30 sec based on the motor speed. Alternatively, a manual in and out movement is possible as well. The vertical thickness (size) of the laser delivery system is designed such that it still clears the major facial features of the patients (nose, cheeks, . . . ) without any readjustment of the microscope during the in and out movement.

Another invention relates to methods and systems for removing a anterior and posterior capsule of an eye. The above microscope integrated laser system is used as follows:
  a) Bring the laser system in the "in" position complete alignment and perform a laser capsulotomy (capshulerexis) procedure of the posterior (distal to laser delivery system) capsule. Then target the anterior capsule (proximal to laser delivery system) and perform a second laser capsulotomy there. Then move the laser delivery system into the "out" position (disengaged). Then open the eye, proceed with all standard cataract removal steps. In particular, remove the anterior capsule, then remove the lens and finally remove the posterior capsule. Optionally place a IOL such as e.g. an accommodating IOL with haptics and mounting features that lock the intra ocular lens (IOL) into bothe capsule openings (posterior and anterior).
  b) Bring the laser system in the "in" position complete alignment and perform a laser capsulotomy procedure of the anterior capsule (proximal to laser delivery system). Then move the laser delivery system into the "out" position (disengaged). Then open the eye, proceed with all standard cataract removal steps. In particular, remove the anterior capsule and. then remove the lens. Then move the laser delivery system into the "in" position (disengaged) again. Then target the posterior (distal to laser delivery system) capsule and perform a second laser capsulotomy there. Then move the laser delivery system into the "out" position (disengaged) again. Then remove the posterior capsule. Optionally place a IOL such as e.g. an accommodating IOL with haptics and mounting features that lock the intra ocular lens (IOL) into bothe capsule openings (posterior and anterior).

Another invention relates to methods and systems for combining a laser capsulotomy, cataract removal, IOL placement, diagnostic eye measurement and LRI (Limbal relaxing incisions) cuts. The above microscope integrated laser system used in a version without patient eye to laser delivery system docking and which also includes an optical eye diagnostic module to measure refractive errors of the eye during eye surgery, is used as follows:
  a) Bring the laser system in the "in" position, complete alignment and perform a cataract procedure including laser capsulotomy on the anterior capsule or on both the anterior and posterior capsule. Move the laser/diagnostic delivery system to the "out" position. After placement of the IOL, move the laser/diagnostic delivery system back into the "in" position. Perform an eye diagnostic measurement, particularly determining the total remaining cylindrical (cylinder) aberration (error) of the eye with the IOL in place. Based on the measured cylinder error of the eye, program the laser system to perform LRI laser treatment procedure in the cornea to compensate the cylinder error. Perform this LRI laser treatment. Move the laser/diagnostic delivery system into the "out" position again. Finish the cataract procedure with the typical final steps.

This novel surgical sequence cannot be performed by any currently available system on the market since all current laser systems require full patient interface placement on the eye as well as a docking part that connects the eye to the laser delivery system for any laser cutting inside the eye.

This patent interface placement and docking can only be done on a closed eye to avoid eye injury from loss of liquids out of the eye during patent interface placement and docking. The method and system here describes the solution of how to do an LRI cut (or a second capsulotomy cut) after the eye has been opened already. It is here possible, because docking of the patient eye is here avoided.

Figure 26:
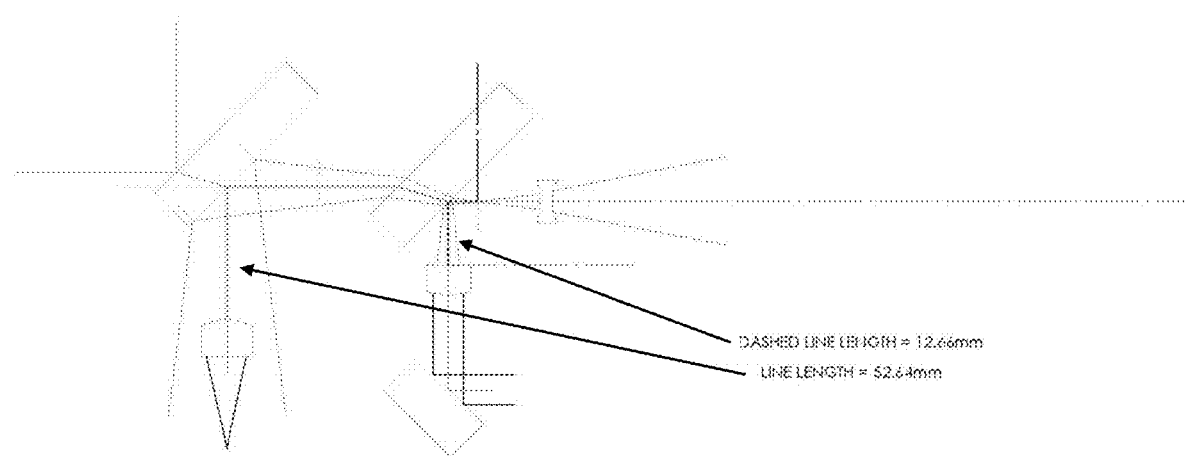
FIG. 26 shows an optical setup.
Figure 27:
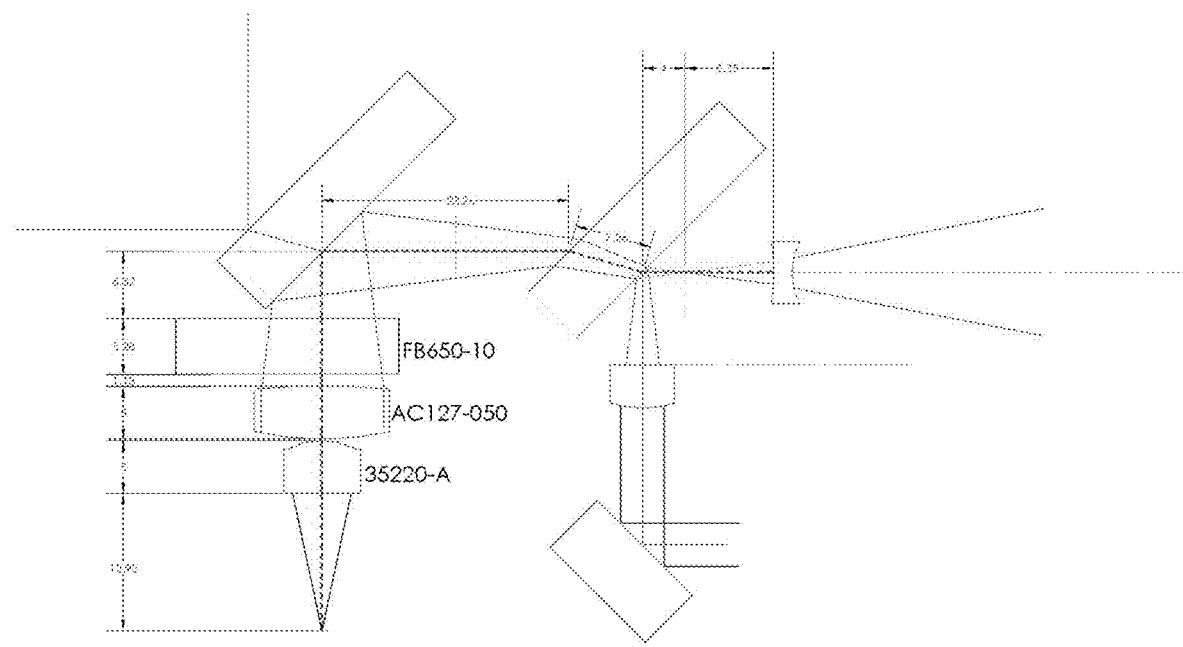
FIG. 27 shows an optical setup for the confocal scanning feedback signal.
Figure 27B:
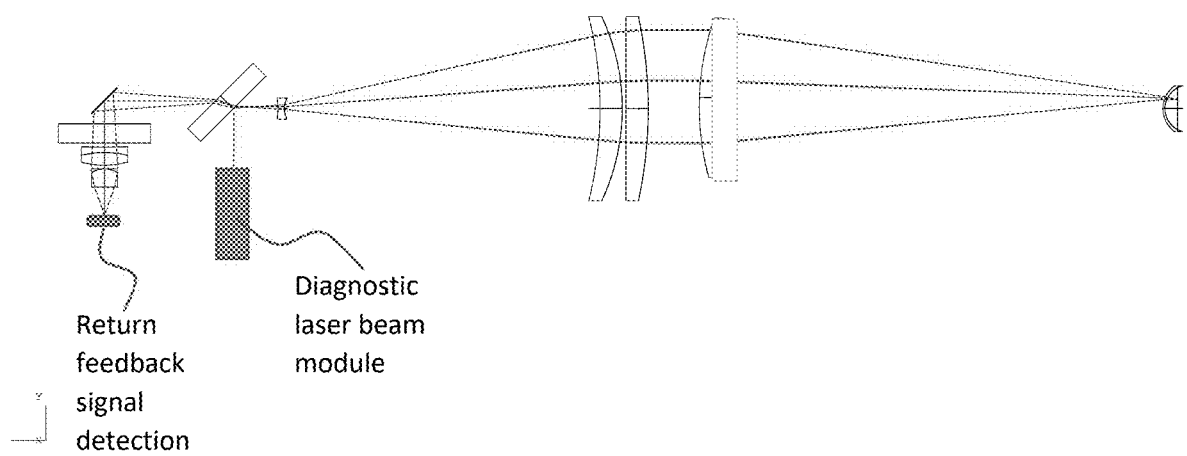
FIG. 27B shows an optical setup for the confocal scanning feedback signal.

Another invention relates to detecting the location and tilt of the anterior or posterior lens capsule before, during and after the treatment laser beam is firing. A diagnostic laser beam is scanned inside the eye with a pattern that allows it to scan a desired volume in the eye. This diagnostic beam is preferably overlapped to the treatment laser beam at some place inside the laser delivery system (see FIG. 27B) or it is targeted into the desired place in the eye through a separate delivery system. Its wavelength can be in the same range as the treatment beam (preferably around 1 um+−0.6 um or it can be shifted more into the infrared or towards blue spectrum. When overlapped within the treatment laser delivery systems, the optics at and after the overlap are preferably coated to optimize all coatings for minimal losses in treatment laser power as well as diagnostic laser power. The diagnostic laser beam is focused using preferably the same focusing lens or lenses as the treatment beam to achieve a preferable spot size of 1 um to 20 um inside the eye. As the diagnostic laser spot is scanned through the eye a small return feedback signal is monitored in the delivery system as shown in FIGS. 26, 27 and 27B. This feedback signal consists of back scattered and back reflected laser light. The most intense back scattering or back reflection will come from the area around the laser focus in the eye hereon called the stimulating focus, since it exposes the eye tissue to the highest laser intensity. The return imaging optics is set up that the returning light path images the stimulating focus to a detection focus on a light sensor, preferably a photodiode. The purpose of this diagnostic laser beam is to detect and map any interfaces, surfaces and changes in eye tissue density or texture. The stimulating focus will create the strongest light signal when the stimulating focus is scanned across an interface inside the eye that has a quickly changing index of refraction. The most pronounced such interface in the anterior chamber of the eye is the transitions from aqueous humor into the lens capsule. Other strong signal interfaces are anterior capsule layer to lens tissue or posterior lens capsule to vitreous body. As the stimulating focus is scanned through one of these interfaces there is a strong feedback light signal (scattering and reflection) that can be detected at the light sensor in the delivery system. Different tissue densities and textures will also provide varying strengths of the feedback light signals arriving at the light sensor. For example, the iris tissue will create a very strong feedback signal due to its pigmented and reflective nature. Also, a later stage cataract lens (white cataract) will create more feedback signal than an earlier (clearer) cataract lens. Aqueous humor in the anterior chamber will create the least feedback signal strength unless there a floating particles such as blood cells or other substances, which will create a stronger localized feedback signal. The cornea and vitreous layers will create a stronger feedback signal than the clear aqueous humor. The goal of this diagnostic laser beam is to scan the stimulating spot through the desired area of the eye which can be any or all regions of the eye and by monitoring the feedback strength of every location within the scan volume, creating a 3 dimensional map of various tissue layers, anatomical features and artifacts within the eye. This 3D map becomes an image of the entire scan region ion the eye that allows diagnostic interpretation as well as tracking and guidance information for a treatment laser beam. This diagnostic capability can be used to guide a treatment laser in the following case. The stimulating spot is scanned in a cylindrical area in the eye consisting either of stacked scanned circles that start posterior to the phacic lens and successively move more anterior in the eye until the circle has entirely cleared the lens or the entire eye through the cornea or the scanning cylinder can be created with a continuously rising spiral that starts in an anterior part of the eye and ends in a posterior part of the eye or exits the eye entirely through the cornea. The scanning direction for both cases can also be reversed starting with anterior (up) position and scanning towards a posterior (down) position. Or the scanning can continuously sweep through the eye up and down with a used or system defined range and cylinder diameter. Such a cylinder scan is used to image the entire eye features within the scanning area and volume. A preferred scanning cylinder will be placed through the entire phacic lens or through any or all parts of the eye including cornea, anterior chamber, lens and vitreous body and retina. The imaging data from such a cylinder sweep will show the position and any tilt amount and tilt orientation of the phacic lens and the anterior and posterior capsule. A partial lens scan is also possible e.g. imaging only the anterior capsule and part of the lens. This precision location data of the capsules and lens is used to guide the scanning delivery system of a treatment laser to perform a capsulotomy (anterior and/or posterior) as well as a possible lens fragmentation where exact lens location is essential for targeting the right tissue sections and avoiding the wrong once. Such an imaging scan can be performed once or multiple times before the treatment laser is activated or it can be continuously scanned, before, while and even after the treatment laser is active. Imaging while the treatment laser is active allows for constant targeting updates and corrections in case there is movement of the eye or movement of features within the eye during the laser treatment time.

The following additional inventions are disclosed to enhance the feedback signal resolution and strength:

Adding a pinhole in the plane of the feedback return focus (preferred size 10 um to 50 um) to achieve a confocal microscope effect with a much enlarge special resolution and signal to noise ratio. Optionally this pinhole can be adjustable in the longitudinal beam dimension and thereby providing a z-scan for the measurement.

Optimizing the wavelength and the coatings on all optics to maximize the return signal strength.

Using a very narrow band or interference filter with a preferred bandwidth of <100 A (Angstrom) to separate the diagnostic beam signal from all other light sources including the treatment laser wavelength and any illumination scattering.

Frequency and/or amplitude modulating the diagnostic laser beam and then using a "lock-in" amplifier on the signal detection side to significantly increase the signal to noise ratio.

Figure 9:
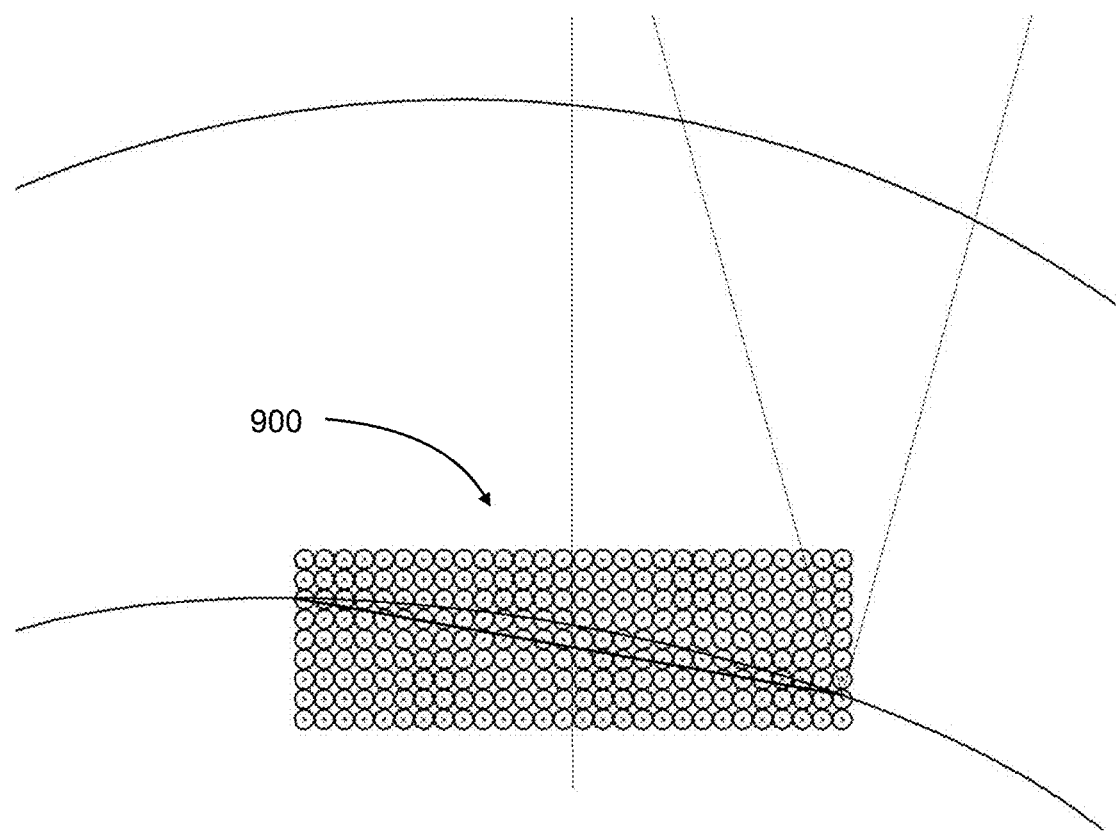
FIG. 9 shows a full cylindrical laser scanning pattern cutting a tilted capsule of an eye.
Figure 10:
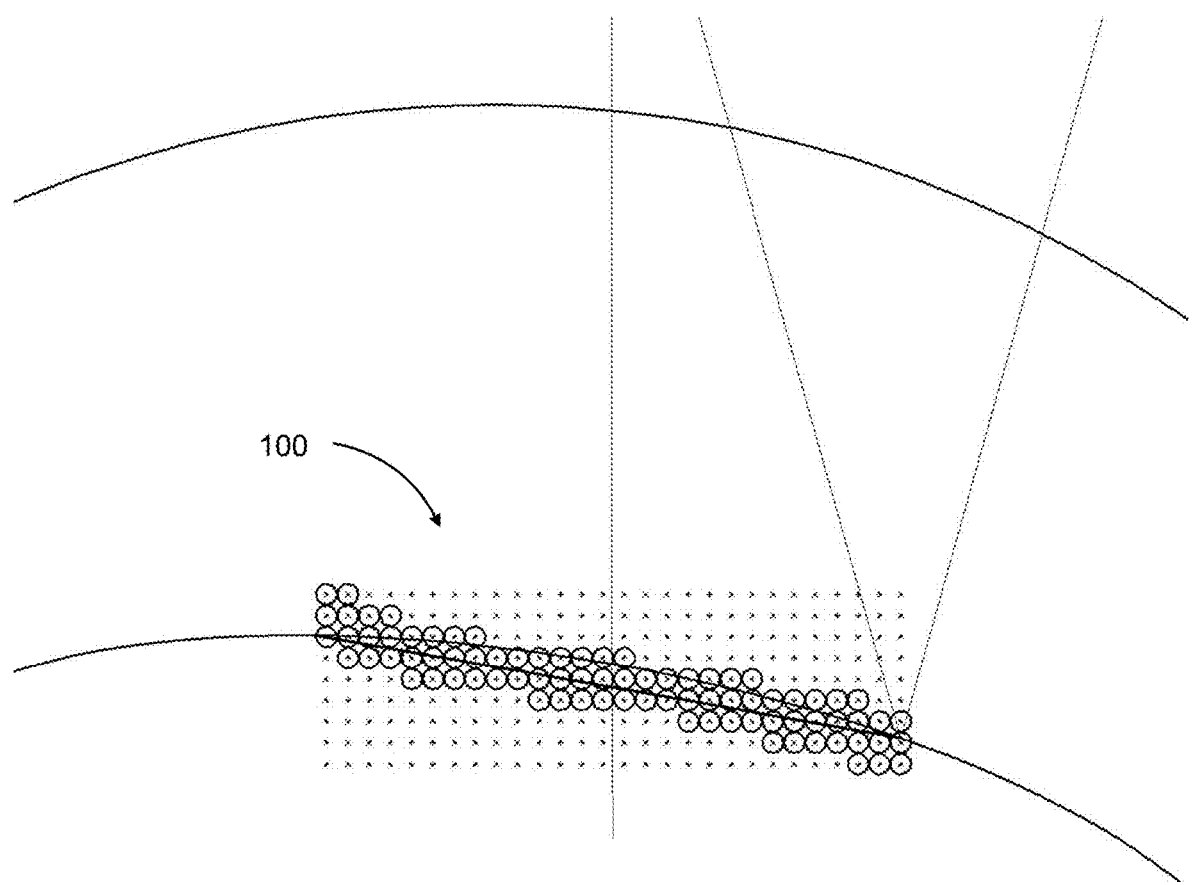
FIG. 10 shows a "on" and "off" modulated laser scanning pattern cutting a tilted capsule of an eye with far less laser pulses compared to FIG. 9.
Figure 11:
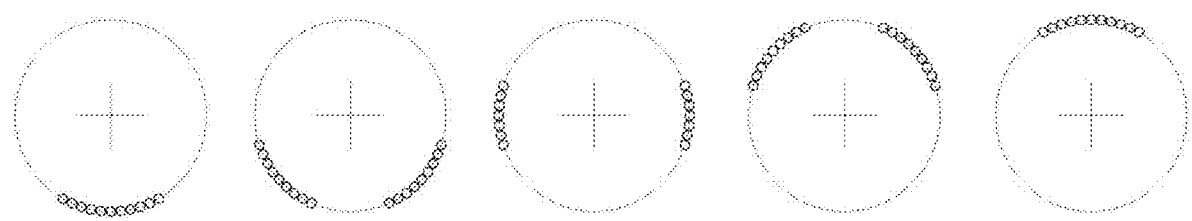
FIG. 11 shows a time sequence top view of the pattern cut in FIG. 10.

Use pulsed laser pulses for the diagnostic laser beam to increase peak intensity to increase feedback signal strength while keeping average power low. With or without a lock in amplifier configuration Another invention relates to new femto laser scanning and laser on-off modulation methods. When firing laser pulses into the eye for any laser treatment, it is always preferred to minimize the amount of necessary laser pulses as much as possible. Reducing the amount of required laser pulses reduces the risk and total energy load onto the eye. Reducing the amount of required femtosecond laser pulses in particular also reduces the amount of cavitation bubbles produced. Every pulse typically produces a bubble that often can accumulate or that obstruct the path for future laser pulses that are targeted through some existing bubbles. The accumulation of such bubbles can lead to local pressure build up that can damage or start moving certain features in the eye. For example, a cylinder scan that cuts through the capsule of the eye from the bottom to the top often results in a bubble accumulation right under the capsule membrane This accumulation leads to a pushing upwards motion of the capsule that can then lead to a sudden "burb" bubble release at the place of first capsule cut section. Such a "burb" then causes a rapid capsule membrane collapse which in turn can cause a non-optimal laser cutting completeness resulting in capsule sections that have not been cut at all or not been optimally cut. The here described invention relates to a method to minimize the amount of laser cavitation bubbles by modulating the laser pulses on and off while the laser beam is scanned over a lens capsule interface. FIG. 9 shows the typical arrangement of lase pulses in a cylinder cut through the capsule (independent if the cutting direction is down to up or reverse). FIG. 10 shows the same tilted capsule cut but now with far less laser pulses (bubbles) used. This reduction in bubbles is achieved without changing the scanning pattern. This pattern still consists of full scanning circles the lay on top of each other. What's different now is that the laser itself is modulated on and off during each circle such that it is only in the on state when the circle segment gets close to the capsule and then passes through it. After pass through the laser is modulated off again. FIG. 11 shows this modulation in a sequence of top view drawings from left to right. In these top views the capsule is tilted such that its highest (proximal) point is at the 12 o'clock position and the lowest (distal) point is at the 6 o'clock position. The laser scans in circles here from left to right in a distal to proximal direction (the laser source is here proximal to the paper). The first laser circle that cuts a section of the capsule (left image) cuts only around the 6 o'clock position and the laser firing is turned off again from about 7 o'clock to 5 o'clock. As the laser circles move higher (proximal) the laser on region splits into two symmetric areas and merges again at the highest circles at 12 o'clock. This here invented method minimizes the amount of laser pulses dramatically without sacrificing the desired cutting effect of the capsule. A top to bottom (proximal to distal) cutting sequence works analogously.

Figure 2:
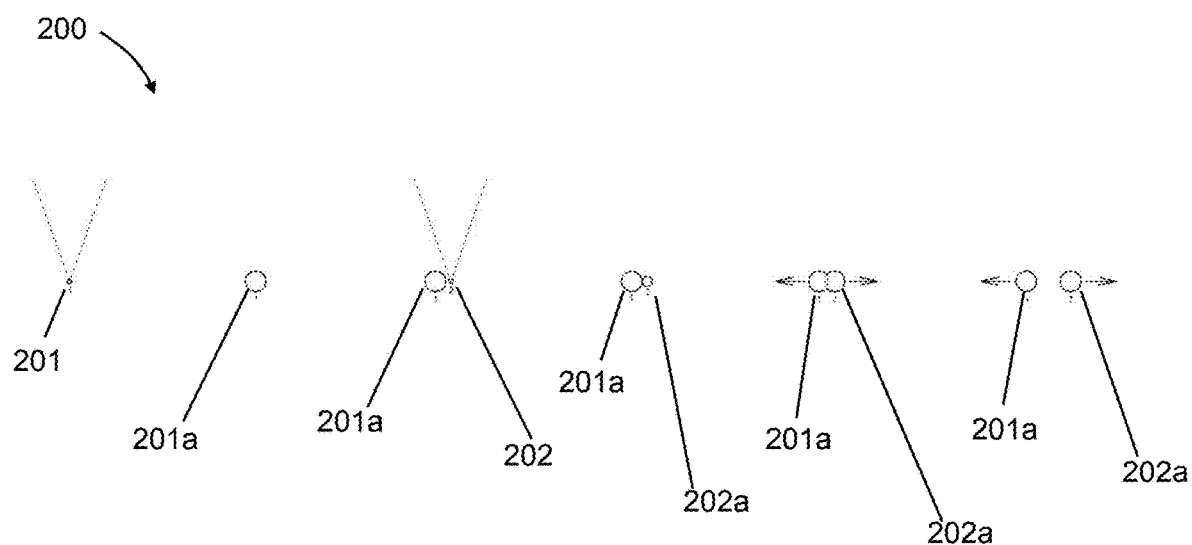
FIG. 2 shows a sequence of 2 laser pulses being delivered with a controlled spacing that results in bubble separation
Figure 3:
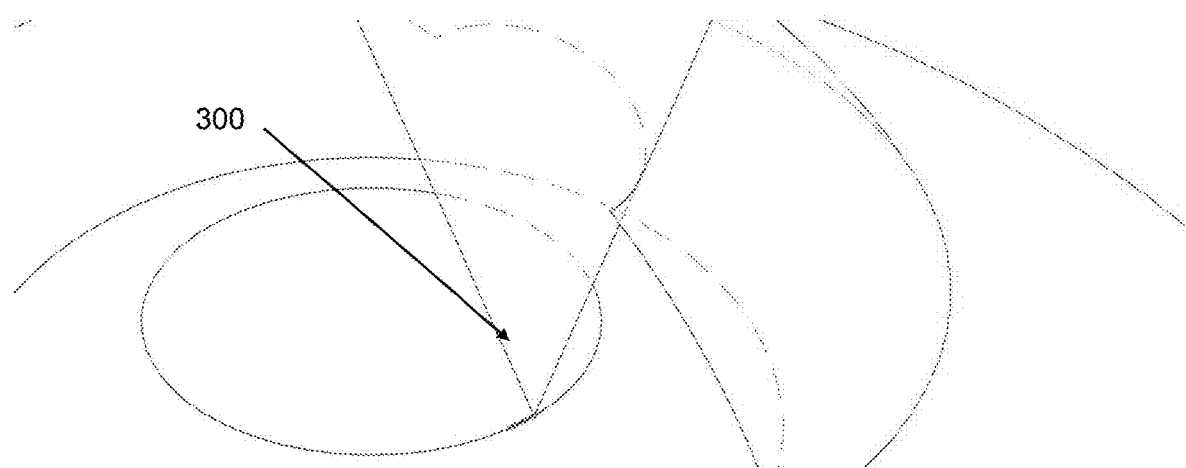
FIG. 3 shows a circular laser pulse sequence scan.
Figure 5:
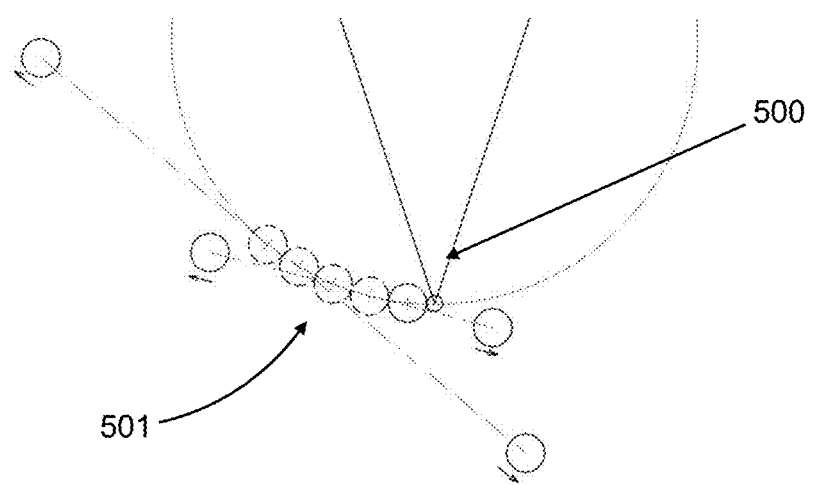
FIG. 5 shows a top view of the bubble dynamic for a spatially controlled laser pulse sequence.
Figure 6:
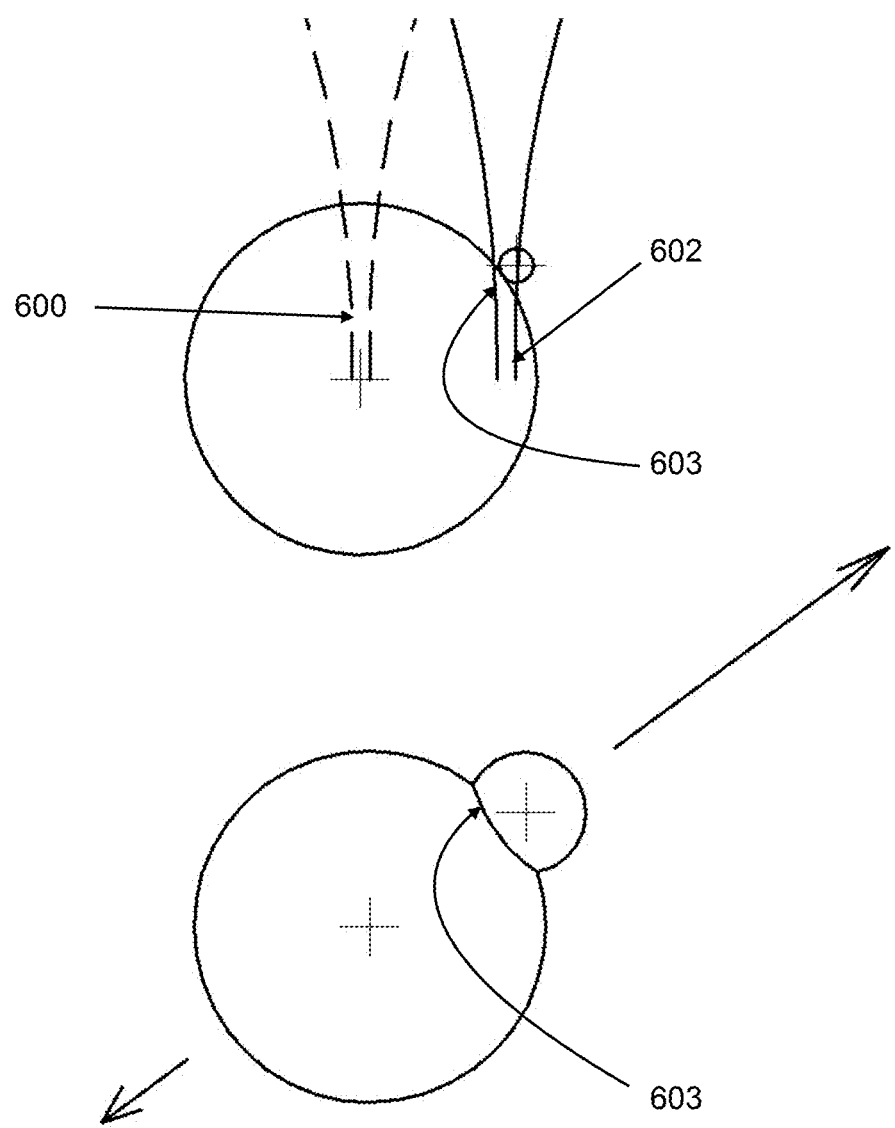
FIG. 6 shows a detailed view 2 laser pulses sequenced in time and controlled in spacing and resulting in bubble interference that leads to a dynamic bubble movement.
Figure 7:
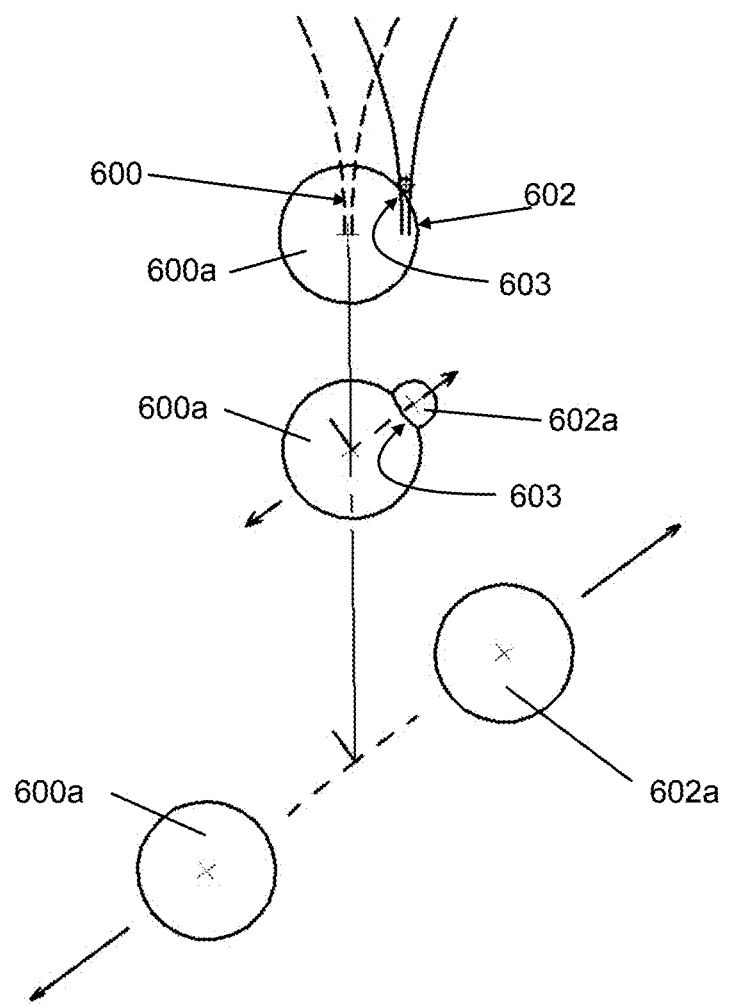
FIG. 7 same as FIG. 6 but with another later stage on the bottom.

Another invention relates to the depth scanning sequence. All currently used and disclosed femtosecond scanning laser systems perform cuts in a strict bottom to up direction within one cutting sequence (distal to proximal). This is due to the fact that in a typical system the laser pulses create micro cavitation bubbles that create an optical barrier that the laser beam cannot effectively penetrate. By starting at the bottom and working the way up (towards the laser source) this interference is avoided or at least minimized. In particular, a capsulorhexis cut is currently always performed as a cylindrical cut starting in the lens material and then circle by circle working its way up (towards the laser source) and through the capsule bag and into the liquid (Aqueous Humor) of the anterior chamber. This approach does avoid bubble-laser interferences, but it comes with the downside of accumulation of many bubbles under the capsule membrane. This accumulation of bubble leads to a buildup in pressure underneath the capsule membrane that starts lifting the capsule as the laser approaches its plane from below. In a way the laser is pushing the capsule bag ahead of its scanning direction. When the laser pulses ultimately cut the capsule than a sudden pressure release "brub" can appear at the first cut section. That sudden pressure release results in a fast drop of the capsule membrane which in turn can result in a non-optimal or non-complete laser cutting of the capsulerhexis since the fast down movement of the capsule membrane may miss the now higher circling laser pulses and therefore some significant sections of the capsule may not be completely cut or not cut at all. The here described invention introduces a novel scanning approach that allows the femto or pico second laser pulses being scanned from top to bottom (anterior to posterior) or in other words proximal to distal while still avoiding the laser bubble interference. This top to down scanning method avoids the disadvantage of the pressure build up and burping as described above and creates a better cutting quality. Femto and pico second laser pulses create microcavitation bubbles that expand from the optical breakdown focal zone within around 100 ns to 5 us to a diameter of about 1 to 100 um based on the amount of pulse energy, pulse duration, spot size and target material. By carefully adjusting all these parameters one can achieve a dynamic bubble ejection effect when multiple bubbles are created next to each other. For any given set of parameters above, the spot separation becomes the critical adjustment for controlling the strength and the direction of this cavitation bubble effect. This effect is used to remove bubbles out of the way of before the next vertical layer of laser pulses is applied to the target area. This then allows the laser patterns to scan layers from up to down without interfering with previous bubbles created by the higher layer. As has been shown in research publications, in the femto second laser pulse domain, the bubble diameter is between 5 um and 30 um and it reaches its maximum expansion between 0.5 us to 3 us after the laser shot was fired in water. Therefore, for laser firing repetition rates of 330 kHz and below a fully expanded bubble is already present when the next laser pulse is fired next to it. FIG. 2 to FIG. 8 show this bubble interference effect in action that results in a desired bubble ejection from the cutting line. As shown in FIG. 2 from left to right, the first laser shot creates a bubble that is almost fully expanded by the time the next laser spot is placed to the right side just slightly outside the first bubble. As the second bubble now expands it will push against the first bubble and both bubbles will as a result accelerate away from each other. FIG. 3 shows a typical circular cutting/scanning pattern. FIG. 5 shows a sequence of several such semi-overlapping laser shots on a scanning circle. In another invention the laser spots can be separated less than the half bubble diameter away from each other. As FIG. 6 illustrates, in this case the next laser focus (here on the right) lays to the right side within the previous now fully expanded laser shot bubble. Since the optical laser breakdown is more likely to happen on an interface between liquid and gas even when the laser fluence is somewhat lower there, the right laser shot will start a new cavitation bubble at its left bubble surface intersecting point as shown in the upper drawing of FIG. 6. The lower drawing of FIG. 6 shows the growing right bubble that is now starting to push against the large left bubble. FIG. 7 on the bottom shows the now resulting ejection of both bubbles from their creation site. Because of the vertical overlap location shift there is now also a vertical separation speed. The right bubble moves up and to the right, while the left bubble moves down and to the left. This particular spacing method has additional advantages since it removes all bubble from the momentary cutting plane (horizontal plane). Taking advantage of such a bubble ejection method now allows the overall scan direction to become top to bottom since this method effectively removes most if not all bubbles in the way of the down scanning laser sequence. The bubble ejection works best when the bubbles are created in a liquid versus a solid or gelatinous material. This up to down scanning method can be used best for any cutting of an interface/surface that has a layer of liquid on top. Such as a downward cutting spiral from the anterior chamber (liquid) down into the eye lens (more solid) and through the capsule of the lens in the process without any buildup or accumulation of bubbles above the capsule that could result in any sudden "burb" and capsule movement. This method therefore results in a more precise and better cutting quality of the capsule of the eye. Another method to achieve such desired bubble interference that leads to an ejection of the bubbles from the creation site can be achieved by shooting 2 or more laser pulses simultaneously into the target region with the predetermined spatial separation such that the bubble interference and ejection happens in the desired way (as detailed above). There are many different available techniques to split a single pulsed laser beam into two or more separate pulsed laser beams with controllable amounts of separation and energy distribution (e.g. various beam splitters, prism configurations and other methods can be used).

Figure 22:
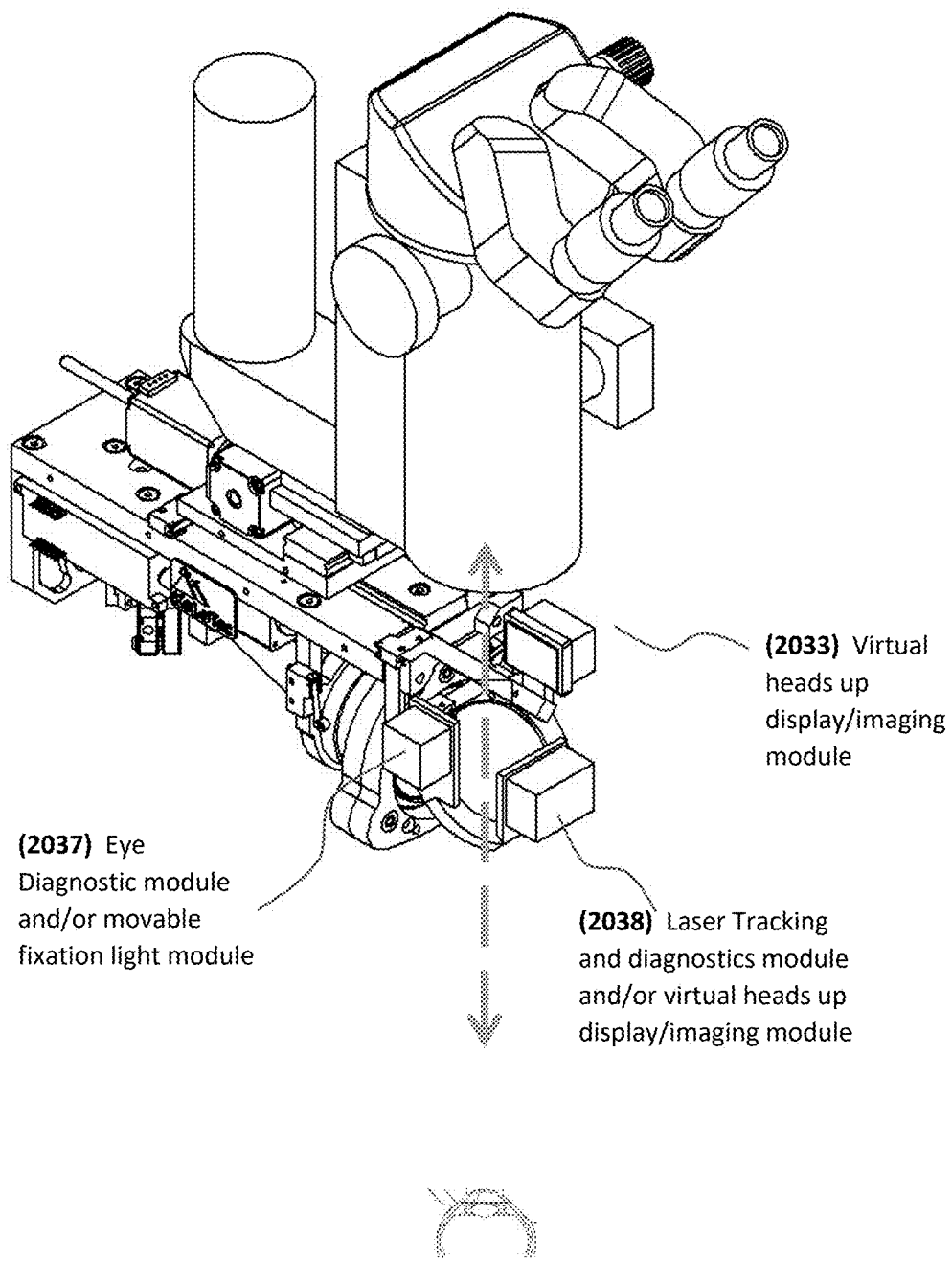
FIG. 22 shows a laser delivery system mounted under the microscope without skins.
Figure 24:
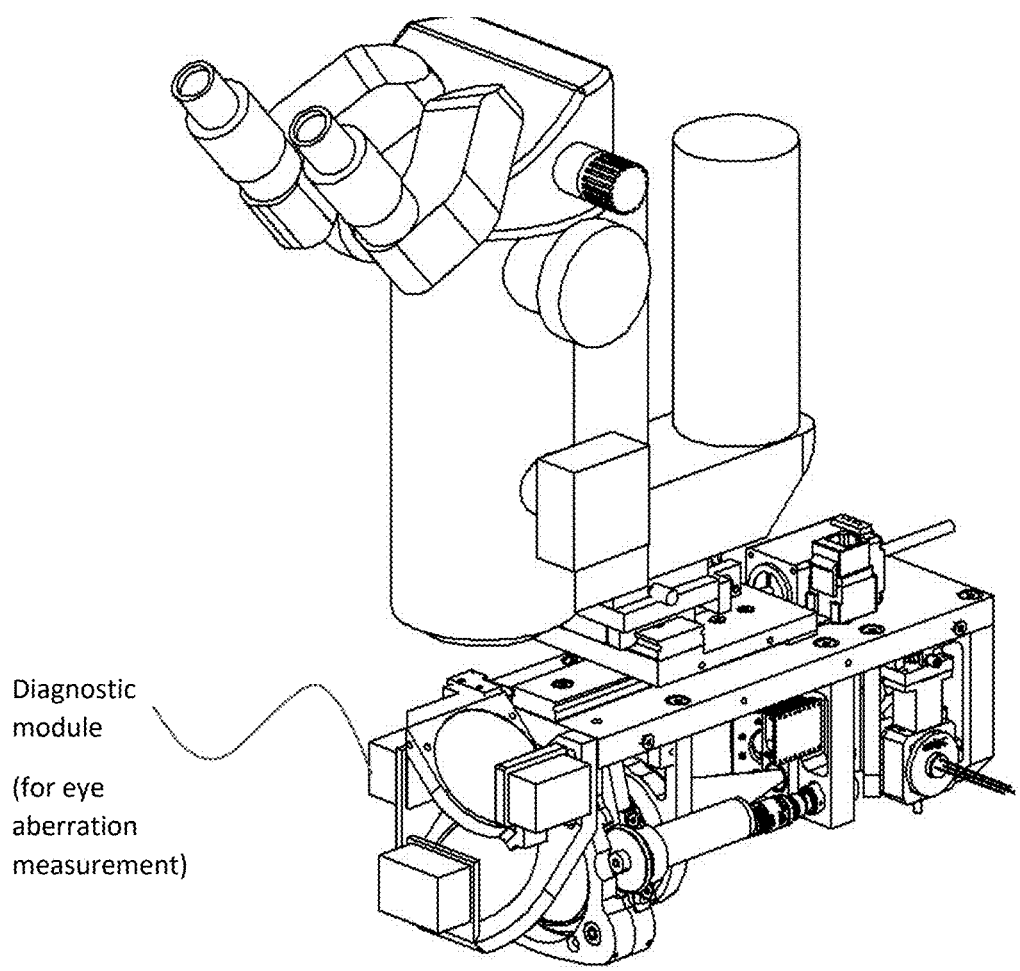
FIG. 24 shows a laser delivery system mounted under the microscope without skins.

Another invention relates to a system that integrates a diagnostics module to scan and measure the eye. This diagnostic module can be either placed into the surgical microscope via a beam splitter that lets the visible light path through to the microscope observer or it can be integrated and optically guided into the eye via a 45 deg mirror above the laser routing 45 deg mirror (final 45 deg mirror in FIG. 23) of the microscope attached laser delivery system. FIG. 22 and FIG. 24 show a configuration of placing such a eye diagnostic module as can be seen at the little rectangular box that includes a optical diagnostics module and that uses a 45 deg mirrors (upper mirror) to rout their signals in and out of the eye. Optionally a Laser tracking and laser diagnostic module can also be included facing the laser delivery system through the lower (final) 45 deg mirror. This module can also operate as a virtual heads up display module transmitting an image upwards into the microscope via the final 45 deg mirror.

Another invention relates an active stabilization system for the surgical microscope. When integrating or mounting a laser delivery system to a microscope, vibrations of the microscope head can affect the laser pointing stability of a laser beam that is exiting such a system and is entering an eye. Such vibrations can be triggered and stimulated by a surgeon moving the microscope head or by touching the eye pieces of the microscope with the facial features around the surgeon's eyes or by any other vibration causes. Another source of location instability of a laser target of such a integrated system is any possible patient eye movement. There are larger scale eye movements in the order of around >0.2 mm that can be caused by physical movements of the patients head (a shaped head pillow can minimize head movements) and eye or by some involuntary eye drifts or tremors. There are also micro movements often described as Microsaccades. Their amplitude in eye rotation is typically less than 1 Deg which results in a translational shift of the eye at the cornea of less than 0.2 mm. this movement happens typically in two dimension. If looked at a patients eye while the patient is standing upright, then these dimensions are up down and left right. This microsaccades and other micro movements are triggered by the heartbeat, bloodflow within the eye or other nerve stimulated small muscle movements. Without using any patient eye fixation, the larger movements can often be avoided or reduced by instructing the patient to fixate his view a small fixation light. To reduce or eliminate the smaller micro movements a patient fixation interface that stabilizes the eye can be used. The resulting effective combined movements is the addition of the larger scale movement and the micro movement in every moment. This combined movement is constantly misaligning the intended laser targeting position. Active motion detection of the combined movements between the laser-delivery/microscope-system and the eye can be done by various means such as a video iris detection system or others. Based on this motion detection data an active tracking system can be implemented to compensate movements by redirecting the laser delivery system to so that the laser beam effectively follows the movements. See invention g) below for more details. Such an active tracking system works particularly good on the larger scale movements that are typically also slower than the smaller micro movements. There are several invention aspects described here that relate to methods and devices to perform laser eye surgery with a laser delivery system integrated with a surgical microscope head in the presence of such larger scale movements and micro movements:

a) A method for performing a laser eye treatment procedure where there is no patient eye fixation device nor any eye to laser delivery system docking device. No active tracking is present. The only reduction of the larger scale movements comes from the optional use of a patient fixation light that the patient centers in his/her visual field. A procedure that has a positioning precision requirement (allowed targeting misalignment distance) that is > larger than the amount (amplitude-distance) of the micro movements, can be performed when the time of the procedure is short enough to were the larger scale movement has not exceeded an acceptable targeting misalignment distance. E.g. the micro movements have an misalignment amplitude of +−0.1 mm in all directions. The acceptable targeting precision for the treatment laser is +−0.4 mm in all directions. The larger scale movements have an amplitude of 2 mm in all directions and occur at moving speed of 1 mm per second. In this scenario any laser procedure that can be completed in less <0.3 s and that is started with optimal targeting precision will stay within its positioning requirement all the way through the procedure time, because in the worst case the 0.1 mm micro movement will be in the exact same direction as the 1 mm/second larger movement which will reach 0.3 mm offset in 0.3 s and the total misalignment will therefore be 0.1 mm+0.3 mm=0.4 mm wich is the acceptable total precision limit. Again, the invented surgical method here is: No patient eye fixation device used, no docking device used. Determine the amount of micro movements and determine the speed of larger scale movements. For any given positioning precision requirement, determine the maximum allowed laser treatment time to perform a laser procedure in the eye that still fulfills the targeting precision requirement.

b) A method as described in a) where a patient eye fixation devices such as in FIGS. 54, 55, 56 and 57 is used to reduce both the larger scale movements as well as the micro movements. The overall method stays the same, but with reduced movements, now the procedure time can be increased for the same positioning requirement or the positioning requirement can be made smaller (better) or a combination of both.

c) A method as described in b) where now also a docking interface device is used such as in FIG. 12, 13, 14, 15, or 16. Such a docking between the eye and the laser delivery system will further reduce mostly the larger scale movements and as a result will allow a larger treatment time or a positioning requirement that's even smaller (better) or a combination of both.

d) A method where a live video imaging system is added to the microscope-laser delivery system, providing real time information data on the momentary targeting misalignment distances (e.g. through iris/pupil position detection) and were such data is used to enable the laser treatment as long as the video data shows the misalignment distance to be within the acceptable laser targeting precision requirement and to trigger an immediate laser shutdown when the targeting precision requirement is exceeded (overrun). This will also function as a laser safety feature. The imaging system enables the laser firing (gives him a green light, e.g. through a heads-up display through the microscope view) but the surgeon still initiates the laser firing with the press of a button (by hand or foot) or by voice control or otherwise. The surgeon's laser firing initiation command will only be executed by the system if the position detection system found the misalignment to be within the acceptable range and has therefore enabled the laser system. Otherwise the surgeon's laser firing ionitiation command will just be ignored and not result in the laser actually firing. In another version the surgeon will be able to initiate the laser firing even if the position requirements have not been met and the system has not enabled the laser firing. The system will now record the surgeon's initiation request and will continue to monitor the positioning misalignment measurement from the imaging system. If within a predetermined time duration (e.g. 2 seconds) the alignment of the target area in the eye falls within the required range, then the system will automatically start the laser firing. If the alignment condition is not met within the predetermined time duration, then the system will fall back to a standby status and the surgeon has to initiate the laser firing again. This method allows for improved alignment since it leaves the ultimate laser firing decision moment to the computer and imaging system which is more precise and can react faster than the human eye-brain of the surgeon. This is particularly helpful when there is some drifting patient eye motion back and forward present. After he surgeon has initiated the laser firing the system can now analyze any momentary patient eye motion and can predict and wait until the eye comes into optimal alignment and then fire the laser without further surgeon input. The surgeon would in one version provide his/her initiation command through a push and hold button. That way the surgeon can at any time withdraw the laser firing authorization (before the system started the laser firing) or stop the laser firing at any moment (if the system has already started the laser friring) by simply letting go of the push and hold button. The surgeon is therefore constantly giving his/her laser firing approval through the push and hold action. In another version of this invention the surgeon can move the eye e.g. by hand through the use of some forcepts or by holding and moving of a patient interface that is connected to the eye (through suction or otherwise). This way the surgeon can also actively improve alignment precision.

e) A method as described in d) where the positioning data is acquired by a means other than a video imaging system. E.g. an OCT or other imaging system will provide the positioning data.

f) An active vibration dampening system integrated in the microscope head or the laser delivery system head. Three different system versions are invented here:
   1. A system were the momentary effective combined movement is detected through the positioning data of a video imaging system detecting a feature of the patients eye (as described in d)) or another system detecting a feature of the patients eye (as described in e)). This data is then used to move a dampening body with a mass on a linear line such that the movement of the mass counteracts the combined misalignment movement and cancels it out or at least reduces it. This can be done for 1, 2 or all 3 dimensions by using 1-3 independent dampening bodies with independent masses and with 3 orthogonal linear motion lines. The movement of the individual dampening bodies is preferably done with a voice coil activated actuator with the mass sliding on a linear slide (stage) or an electric motor, or linear magnetic slide can be used or any other means of motion actuation. The required mass, moving speed and moving distance range depends on the amount and speed of the combined movement range that is being compensated as well as the mass and existing dampening factors of the combined microscope-head and laser delivery system.
   2. A system as in f) 1. Were instead of an imaging system an accelerometer sensor embedded in the microscope head or laser delivery system is used for each dimensional axis to determine the momentary movement and therefore misalignment of the microscope-delivery system and provide the required data to control the compensating movements of the dampening bodies.
   3. A system as in f) 1. Were instead of the imaging system or other system, detecting a feature of the patient's eye and therefore detecting the effective combined movement between system and eye only the movement of the microscope head and integrated laser delivery system is detected and compensated. The detection of any microscope head movement is achieved through an optical system inside the microscope head or laser delivery system. This optical system measures the position fluctuations relative to a static non moving reference point outside the microscope head/laser delivery system, such as e.g. a point or area on the ceiling of the operating room that is tracked/observed by video camera. The optical system is either a video based system locking in on such an outside reference point/area or it could be one or multiple fixed laser that in combination with feedback sensors detect the motion of the entire system relative to a fixed target grid/lines. The video camera can be mounted on the moving microscope head/delivery system looking at a fixed reference target in the room around the system or it could be the other way around. Mounted outside the microscope system in a fixed way and looking at a reference target on the moving microscope head/delivery system.

Any one of the above described active vibration dampening systems can be used for any kind of eye surgery with or without an eye fixation device and with or without any patient eye docking.

g) A method as described in a) or b) or c) where a live video imaging system or another imaging system (e.g. OCT, . . . ) is added to the microscope-laser delivery system, providing real time information data on the momentary targeting misalignment distances (e.g. through iris/pupil position or other eye feature detection) and were such data is used to correct the treatment laser beam by active counter steering within the laser delivery system and therefore reducing both the larger scale movements as well as the micro movements. If the reduction of the combined movement is such that the maximum misalignment is within the positioning requirement, then the possible laser treatment time becomes as long as necessary (infinite). Otherwise, the overall method described in a) b) and c) stays the same, but with reduced movements, now the procedure time can be increased for the same positioning requirement or the positioning requirement can be made smaller (better) or a combination of both.

h) A system as in FIG. 23 where a laser delivery system is mounted underneath a surgical microscope and where the x-y and optionally also z alignment of the laser delivery system relative to the eye that is to be treated is performed with individual motors for each axis that are integrated into the laser delivery system. These motor are actuated by manual control from the surgeon e.g. through a joystick or they are automatically controlled and actuated through a control system that performs active tracking of certain features of the eye e.g. iris tracking based on video data analysis of the eye iris. Or the motors can be actuated as a combination of manual and automatic activation. By using delivery system integrated motors as shown in FIG. 23 the vibrations that are caused by the system movements are minimized versus moving the entire microscope either manually or through typically integrated microscope adjustment motors and actuators.

Figure 15:
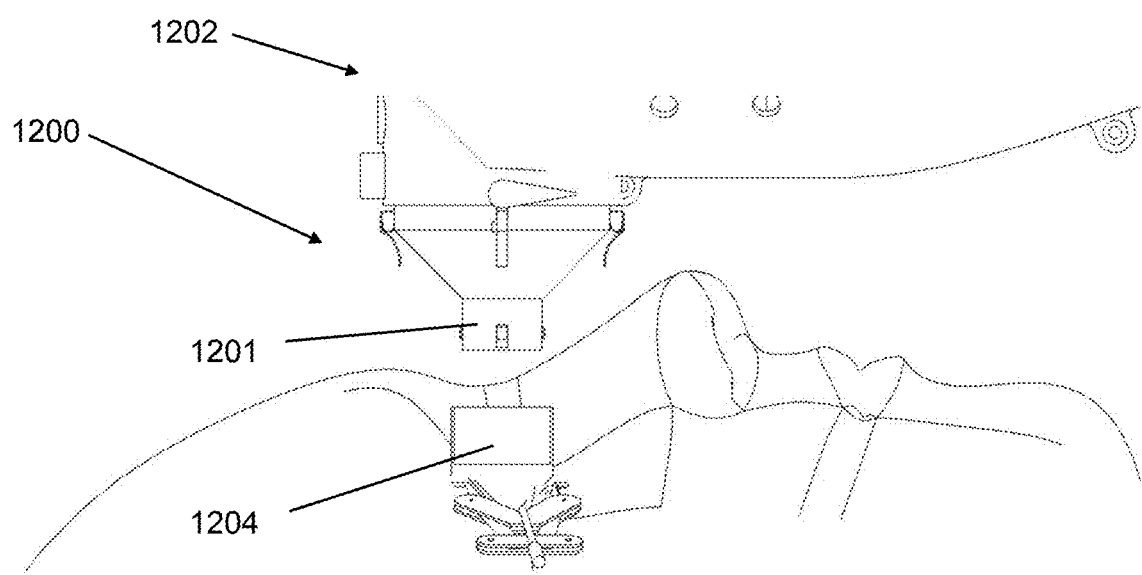
FIG. 15 shows a side/cross-sectional view of FIG. 12.
Figure 16:
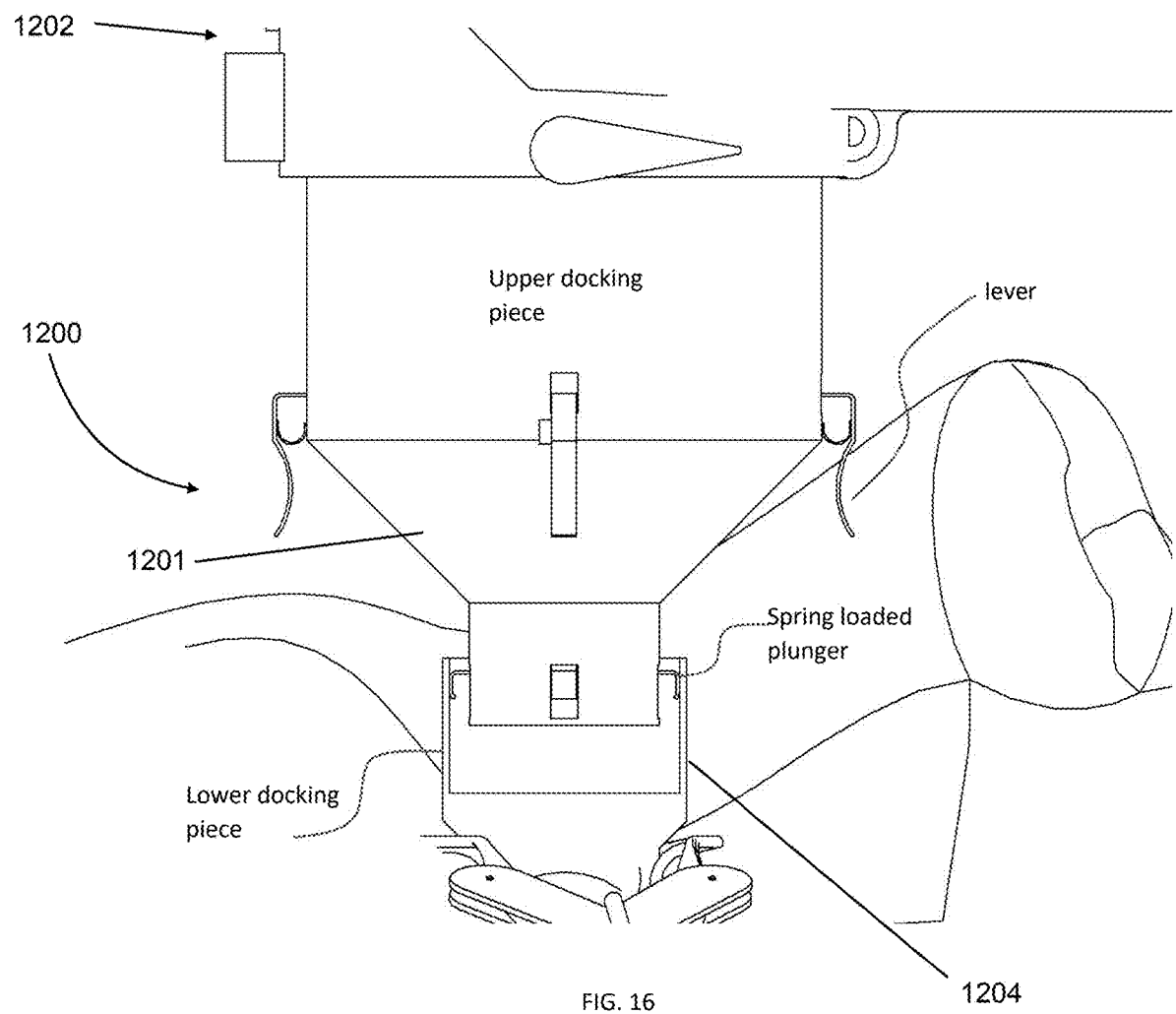
FIG. 16 shows close up of FIG. 14.

Another invention describes a device and method to achieve docking between the laser delivery system (as described above) and the eye. FIGS. 12, 13, 14, 15 and 16 show various aspects and views of the here invented patient eye docking system. Docking a patient eye to a laser delivery system improves the stability and alignment precision of the eye relative to the laser delivery system. FIG. 15 shows the system prior to finalizing the docking procedure. There is an upper docking piece part that is connected to the laser delivery system and there is a lower patient interface part that is here connected to the eye already (e.g. though a suction ring). FIG. 16 shows how the upper piece mates into the lower piece to complete docking. This system has a large margin in the way that the lowest cylinder of the upper docking part has a significantly smaller diameter (here 3 mm smaller) than the inner cylinder diameter of the lower part (patient interface part). This diameter difference adds a lot of play during the docking and makes the docking easy. As the surgeon brings the upper docking part down into the lower part he pushes one of the available little levers on the upper part (3 levers shown in FIG. 16). Pushing any of these levers keeps multiple spring loaded distance plunger inside the cylinder housing. When the final docking position is reached as shown in FIG. 16 the lever is release and the multiple spring-loaded plungers push outwards from the lower cylinder of the upper part and into the walls of the inner cylinder of the lower part. This causes the system to self center and lock itself into place through friction. The docking system and procedure is then complete and the laser treatment can commence. Optionally the upper docking piece is up and down movable (slide able) inside a feature in the upper laser delivery system.

Figure 9B:
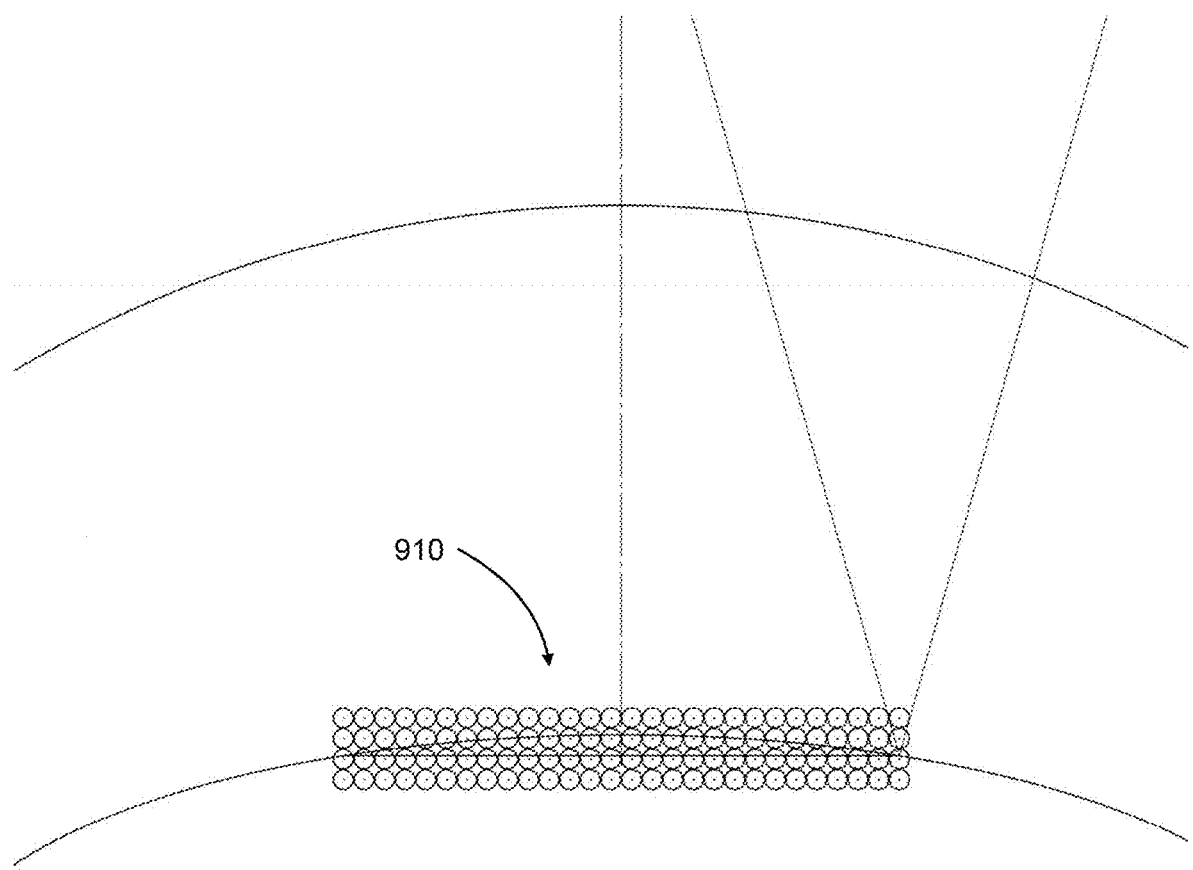
FIG. 9B shows a full cylindrical laser scanning pattern cutting a non tilted capsule of an eye.

Another invention relates to minimizing the laser firing time for cutting a capsule of an eye. As described in other places here, in order to cut a capsule of an eye, the best approach is to scan the individual laser spots in a "cutting" cylinder shape that fully includes the entire capsule that is intended to be cut. In the most common version the cutting cylinder consists of a vertical stack of cutting cylinders or is a continuous upwards circling spiral cut. The overall laser firing time to complete such a cylinder is linearly proportional to the vertical length of the cutting cylinder. As can be seen in FIG. 9 the vertical length of the cutting cylinder allows for some overlap above the highest point of the capsule and below the lowest point of the capsule. The size of this overlap depends on the accuracy of the targeting system and amount of any potential movements in the up- and down direction that is allowed or expected during the laser firing that cuts the cylinder. For any given overlap amount the cylinder length also depends on the amount of capsule (lens) tilt which is the angle between the central patient eye lens plane and the horizontal (constant z-axis) plane of the laser delivery system. In FIG. 9 the effective lens plane is parallel to the straight line that is drawn from the left end of the capsule cut (higher point here) to the right end of the capsule cut (lower point here). The horizontal plane of the laser delivery system (constant z-axis) is here any horizontally shown row of the laser bubbles (the horizontal lines at which the text appears on this page also). The capsule tilt is the angle between those two lines. It can be seen in FIG. 9 that because of the capsule tilt 9 laser circles (bubble) rows needed to be cut in the overall cylinder to cover the entire capsule tilt plus the overlap on top and bottom versus a capsule that had no tilt as shown in FIG. 9b were only 4 laser circle rows (less than half of the tilted case) are needed to cut the capsule. FIG. 9 and FIG. 9b shows a simplified illustration and are not to scale. In more real eye scenarios the effect is often even more significant. E.g. A capsule could be tilted by around 10 deg. Over a 5 mm capsule diameter cut, this tilt will result in a vertical high to low cutting point vertical distance of almost 1 mm. If a 0.1 mm vertical overlap is sufficient to be added above the capsule and below the capsule, then the tilted capsule will require a total vertical cutting cylinder length of 1 mm+2× 0.1 mm=1.2 mm versus a only 0.2 mm length cutting cylinder for an eye without any capsule tilt. The corresponding capsule cutting time increased therefore by 600% from the non tilted to the tilted capsule. In order to reduce the laser firing (cutting) time it is therefore very important to minimize the capsule tilt. The following inventions describe several methods and systems to minimize the capsule tilt in a patient eye prior and during laser eye surgery a) A method and system using an imaging system that constantly scans the capsule of the patients eye and provides full location, tilt amount and tilt direction data to a computer system that analyses and processes the data. No patient fixation device is in contact with the eye. No docking between the eye and the laser delivery system is in place. A laser delivery system that includes a movable fixation light that the patient looks at is present. As the patient keeps the fixation light in his/her central view the imaging system determines the capsule tilt and direction and calculates a correctional shift that needs to be applied to the position of the fixation light so that the tilt of the capsule is fully removed. The control system then moves the fixation light to that new position and as the patients eye follows this fixation light movement, the system verifies the new resulting tilt of the capsule. This will be performed as a constant feedback loop that continuously measures and corrects the capsule tilt and thereby minimizing any possible capsule tilt. As the patient follows the fixation light movements he/she is rotating the eye in its socket which also effectively cause various amounts of translations based on the depth of the feature in the eye. These translations can result in a misalignment of the intended target position. Optionally the surgeon either manually or system automatically corrects the resulting targeting misalignment by manual or automatic tracking (e.g. by moving the microscope head or the delivery system accordingly). An automatic tracking is preferred since the system will then autonomously keep the targeting position aligned while the capsule is being un-tilted. The moving fixation light can be realized by physically moving or steering a light with some motors or by moving some bright pixels on an otherwise dark display screen that is in cooperated into the visual axis line of the patients view (possible routing through some beam splitters). System in FIG. 22 shows a movable fixation light module mounted left of an upper 45 deg mirror through which the fixation light is routed/imaged into the eye below. The control system can then also enable the laser firing when the tilt amount is reduced below an acceptable level (e.g. 2 deg).

b) A method using an imaging system that constantly scans the capsule of the patient's eye and provides full location, tilt amount and tilt direction data to a computer system that analyses and processes the data. No docking between the eye and the laser delivery system is in place. The surgeon is informed of the momentary tilt amount and direction either through a display (possible a heads up display within his microscope view) or through some other optical indications. The surgeon uses this information to manually rotate the eye using some simple forceps to grab and move the eye (e.g. at the limbus) or he grabs a patient fixation device that is connected to the eye already (e.g. a suction ring) and moves and rotates such a patient fixation device. The rotation of the patients eye is intended to un-tilt the capsule. The surgeon will receive instantaneous and constant feedback about the capsule tilt and direction so that he/she will be able to minimize any tilt with these manual eye movements/rotations. The control system can furthermore provide directional indications to which direction the surgeon needs to rotate the eye to reduce the tilt. The control system can then also enable the laser firing when the tilt amount is reduced below an acceptable level (e.g. 2 deg). Rotating the patient's eye in its socket also effectively causes various amounts of translations based on the depth of the feature in the eye. These translations can result in a misalignment of the intended target position. Optionally the surgeon either manually or system automatically corrects the resulting targeting misalignment by manual or automatic tracking (e.g. by moving the motorized microscope head or the delivery system accordingly). An automatic tracking is preferred since the system will then autonomously keep the targeting position aligned while the capsule is being un-tilted.

Figure 57:
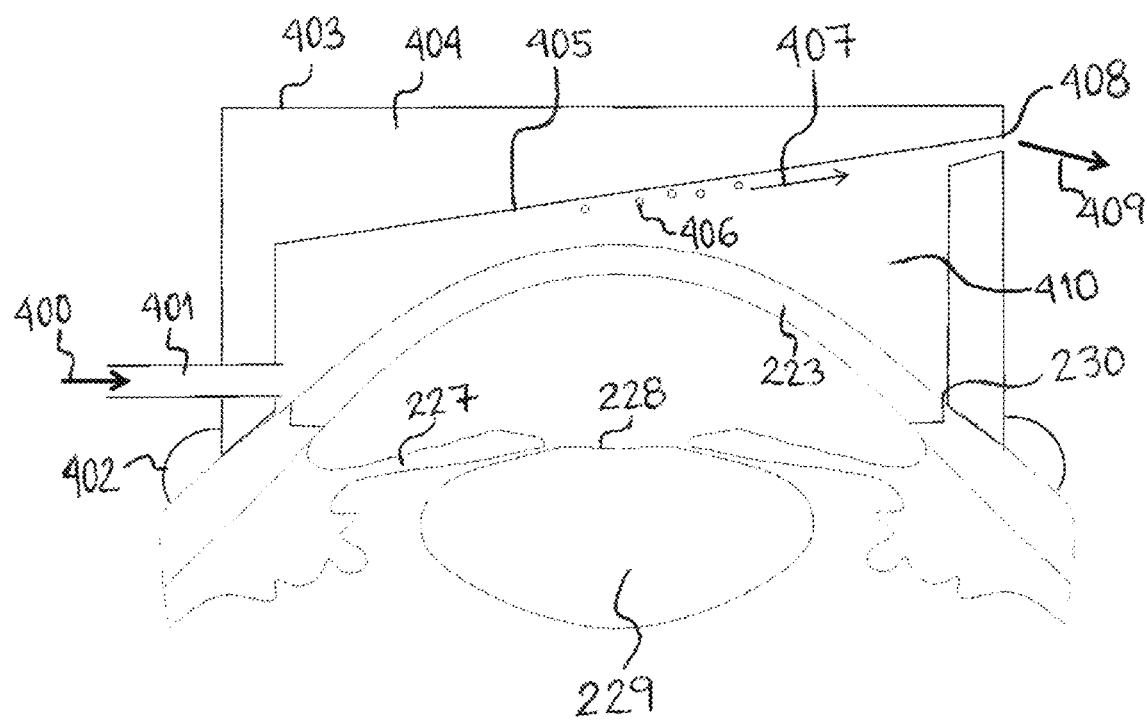
FIG. 57 shows an eye with a patient interface attached to it.

FIG. 57 shows a custom contact lens that reduces aberrations and increases eye fixation while still being non-docking in regard to the delivery system. It is designed to be used in a position where the patient lays on his back and the central eye axis is parallel to gravity. The aberrations are minimized by using a high quality transparent material 404 with a flat top surface 403. The lens is placed along the limbus 230 of the eye. An optional suction ring 402 can be incorporated to increase the connection stability of the contact lens to the eye. This design causes no cornea applanation (which can lead to cornea wrinkeling) or significant intra ocular pressure rise due to the liquid inner cell 410.

After the lens has been placed on the eye the inner cell 410 is filled 400 with water or similar liquid through an opening 401 on the lower end of the contact lens. Due to the slope 405 of the inner top surface any remaining air bubbles will be pushed out 409 through an exit hole 408 on the upper end of the contact lens. The water is injected until all air has left the space 410.

Due to this liquid interface a very good refractive index matching is achieved between the material on the top of the contact interface, the liquid in space 410 and the cornea 223. This creates a low aberration entry path of a highly focused laser beam into the eye.

By using this contact lens the rotating focusing lens in the delivery system can be simplified to a standard plane-convex single lens and the laser beam can be scanned with very low aberrations throughout the entire eye.

Figure 54:
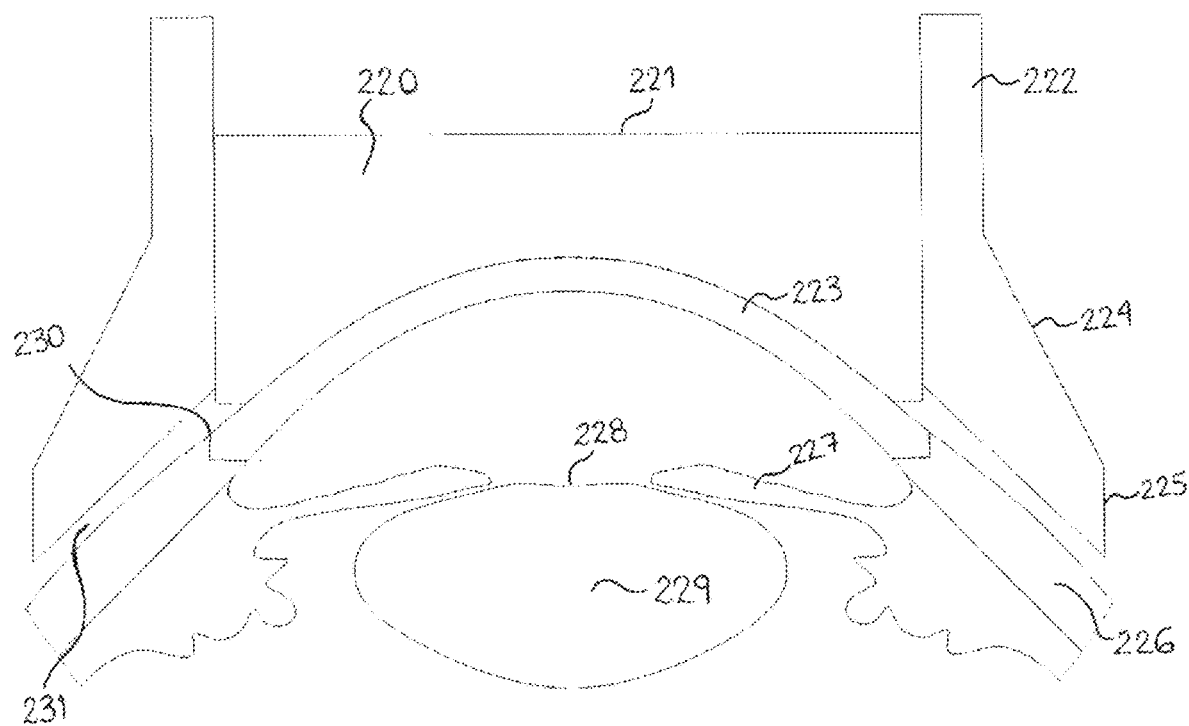
FIG. 54 shows an eye with a patient interface attached to it.

FIG. 54 describes another device invention being a custom contact lens that reduces aberrations and increases eye fixation while still being contactless in regard to the delivery system. This design is comprised of a clear material 220 that is either solid and curved to match the radius of curvature of the cornea 223 or is filled with a clear liquid and then stabilized with a flat glass plate 221. In either case the top surface 221 is flat and therefore minimizes aberrations. The lens includes an outer flange 225 that extends over the sclera 226 while maintaining a small gap 231. This gap assures that a good cornea connection of a solid version material 220 is achieved. When a liquid material 220 is used, the gap is then automatically closed and seals the liquid in.

Figure 55:
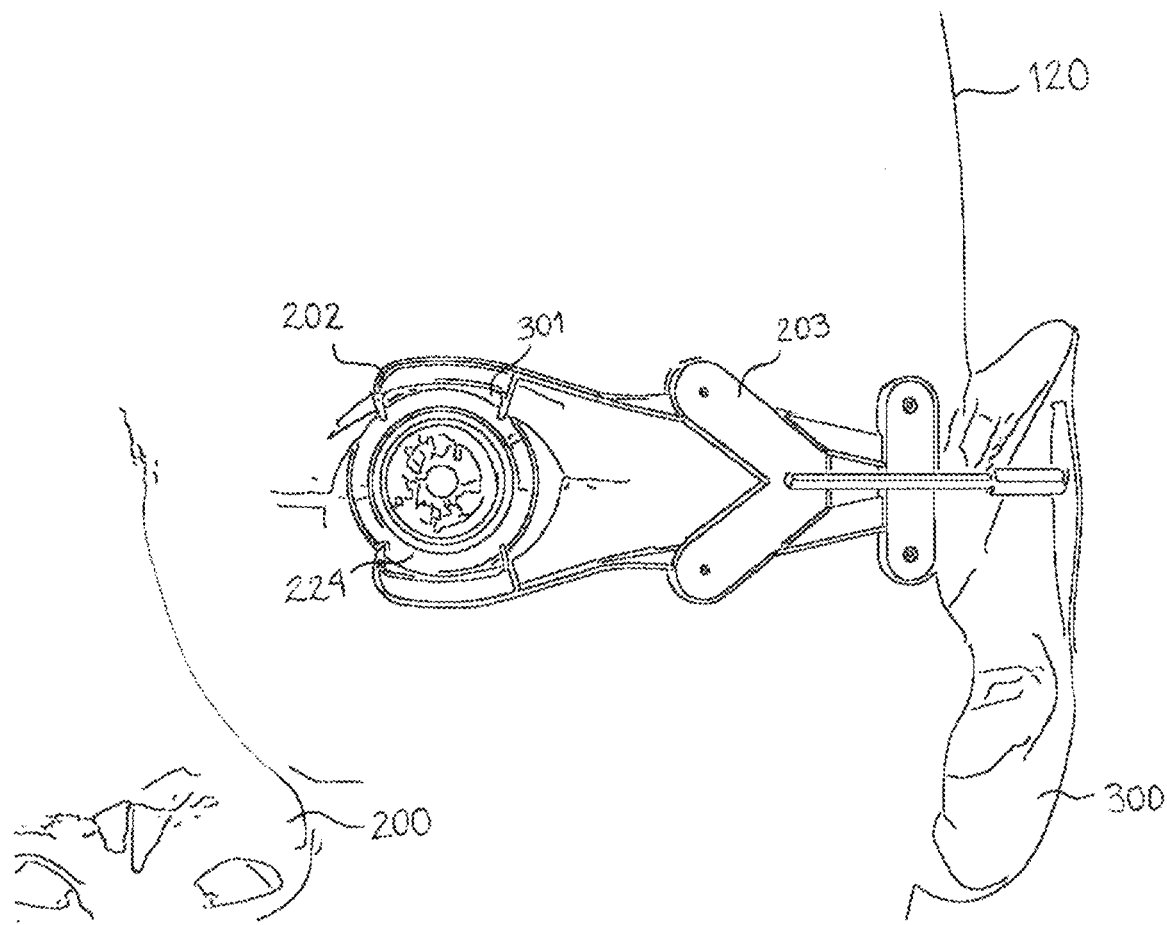
FIG. 55 shows an eye with a patient interface attached to it.
Figure 56:
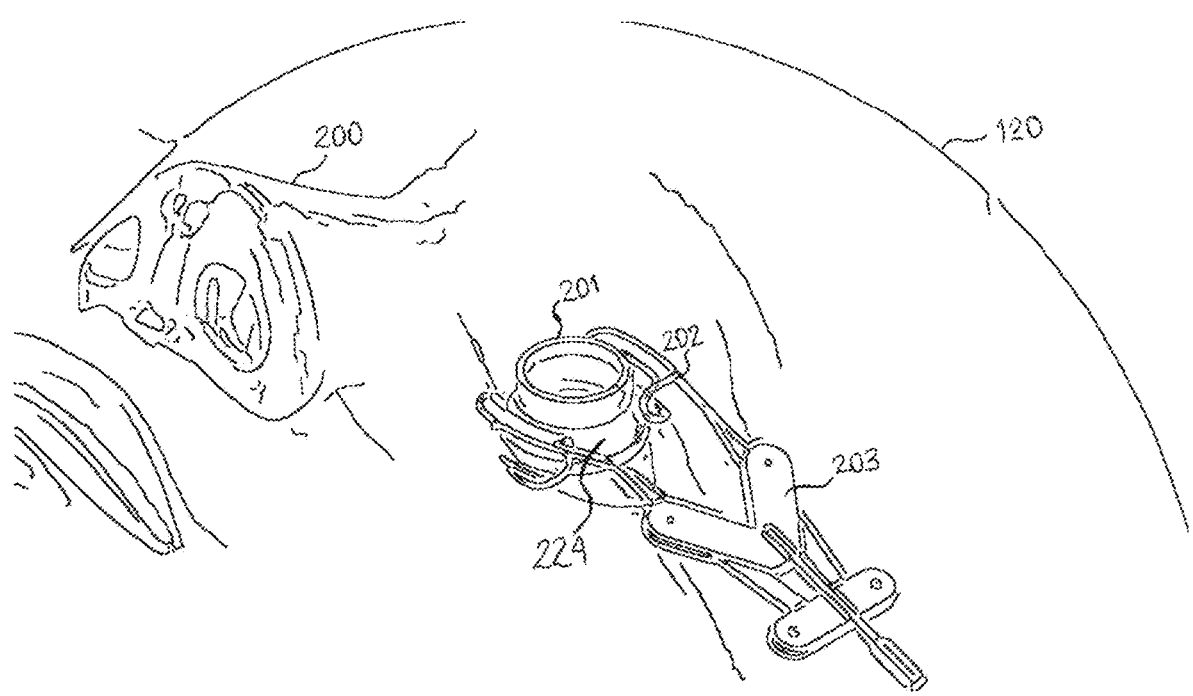
FIG. 56 shows an eye with a patient interface attached to it.

The flange 225 includes an angled slope surface 224 that is designed to interface with a speculum such that the contact lens is slightly pushed downwards towards the eye. This is illustrated in FIG. 55 and FIG. 56.

The speculum 203 is holding the eye open and in the same time pushes the contact lens towards the eye through a contact of the speculum wire 202 or blade with the sloped surface 224. The amount of down force can be adjusted by the amount of speculum opening and by the design angle of the slope 224. This contact lens creates stable eye fixation and minimizes laser beam aberrations for laser access of the entire eye.

Figure 58:
FIG. 58 shows a patient eye under a delivery system prior to docking.

FIG. 58 shows a system of prior art where the patients eye 121 is positioned under a patient interface 240 that is hard connected to the optical delivery system 104b. The picture illustrates the setup procedure just prior to docking the patient interface 240 with the eye 121.

Figure 21:
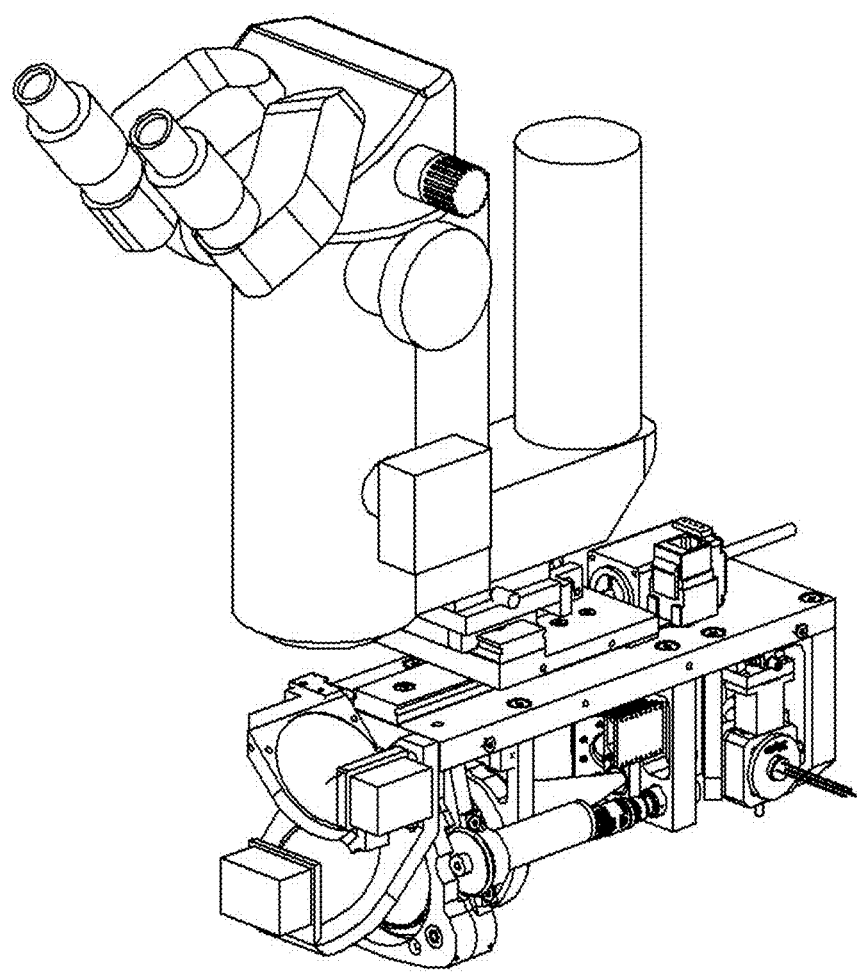
FIG. 21 shows a laser delivery system mounted under the microscope without skins.
Figure 59:
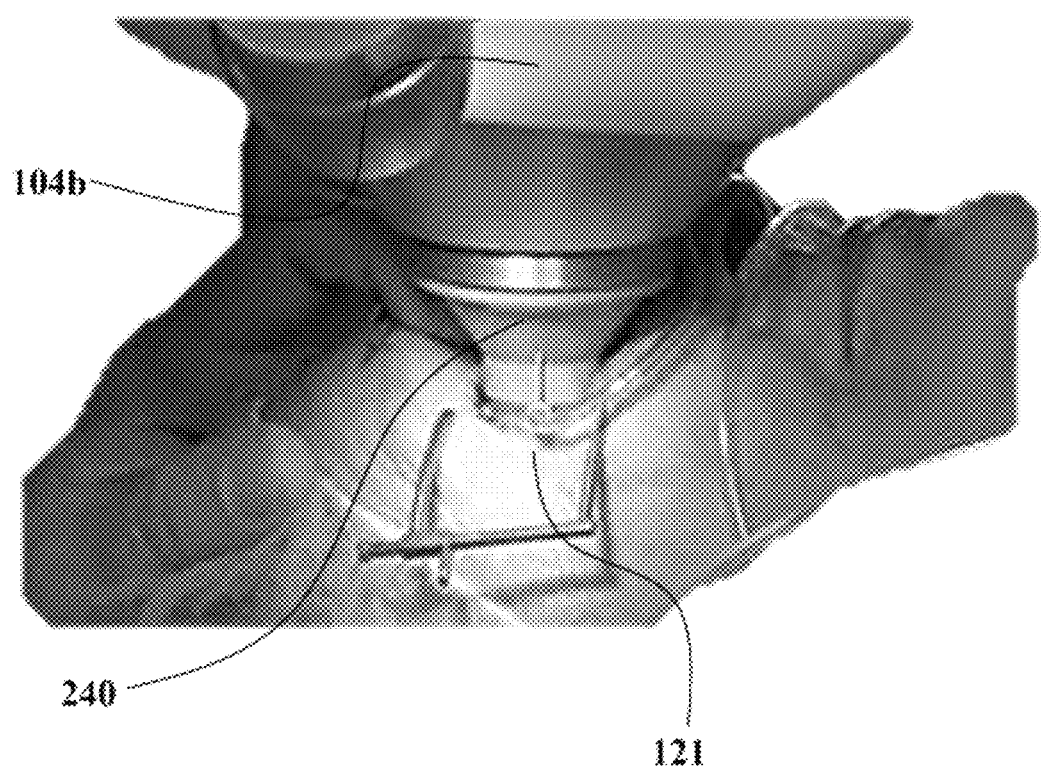
FIG. 59 shows a patient eye under a delivery system after docking.

FIG. 59 shows the illustration from FIG. 21 right after docking is complete. The patients eye 121 is now fixated under the patient interface 240 which in turn is hard connected to the delivery system 104b.

Figure 60:
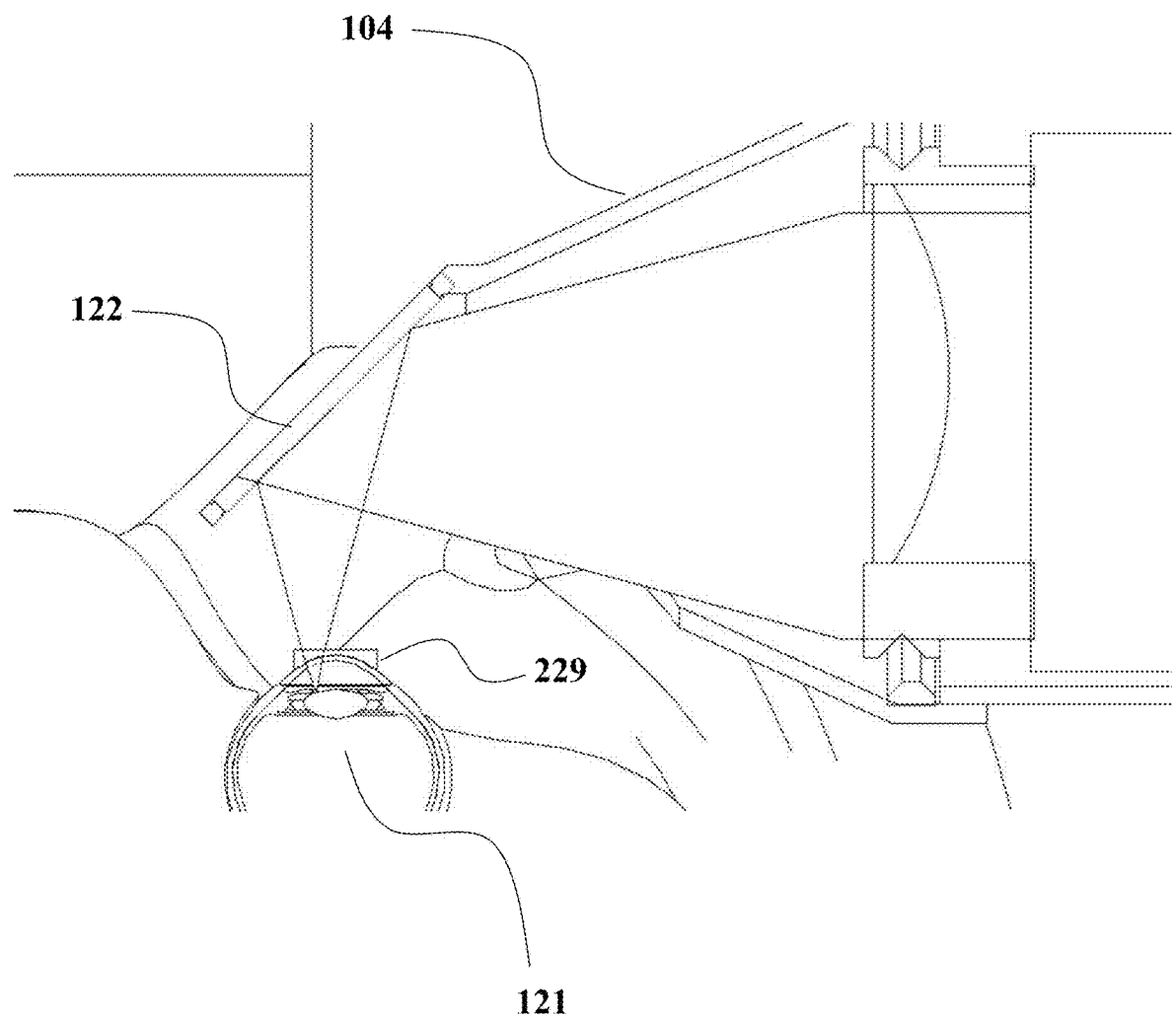
FIG. 60 Optical cross section of a laser delivery system.

FIG. 60 shows a cross sectional view of the laser beam path as it propagates through the delivery system unit 104 and onto the 45 deg mirror 122 and into the eye 121. Illustrated on the eye 121 here is a patient interface 229 that is in contact with the eye, but does not make any connection with the delivery system unit 104. This figure therefore illustrates a non-docking surgical setup.

Another invention relates to treating the iris combined with cataract surgery using a surgical microscope integrated laser delivery system. A pulsed laser system with a pulse duration in the nano second range or longer (>1 ns) such as a q-switched Nd: YAG laser can be used to treat the iris of an eye by applying laser pulses onto the iris tissue. The here described method relates to a laser treatment that is sufficiently low in laser power so that the iris tissue is not disrupted or destroyed (as done with laser iridotomy) but rather using a laser power density (fluence) that is just high enough to dis-launch, release or decompose the pigments in the iris. The laser focus is hereby scanned over parts or the entire surface of the iris (optionally also using a goniolens to reach the outer iris regions). Eye tracking can be used to compensate for any eye movements during the laser procedure. The laser can be scanned multiple times over the same area of the iris with a lower power to achieve a accumulative pigment removing effect or it can be optimized in power and fluence that a single scanning pattern covering the iris in a single sweep is sufficient to achieve the desired pigment removing effect. A eye fixation device (such as a suction ring) can be used to stabilize the eye movements during the laser procedure. This pigment removal effect can lead to a flooding of the anterior chamber with pigmentary particles that if not removed from the eye can pose a risk of pigmentary glaucoma since pigment particles can plug up the aqueous humor outflow channels and then lead to a rise in intraocular pressure (IOP). A patient with pigmentary glaucoma can be treated with such a laser by scanning the laser spot over parts or the entire iris and therefore dis-launching and removing all or parts of the iris pigment. If this laser procedure is then immediately followed by opening the eye and washing out the anterior chamber and therefore removing the floating pigment particles, than the risk of a aqueous humor outflow clog up is removed. Removing some or all pigments of an iris using such a pulsed laser system can also be used to changing the color (bleaching) of the iris. Again if followed by a washout of the anterior chamber, the risk for aqueous humor clogging build up is removed. Therefore, both applications a) treating a patient with pigmentary glaucoma or b) treating a patient to change (bleach) his/her iris color can be done using the same pulsed laser system and can be effectively combined with cataract surgery since the eye needs to be opened and washed out during cataract surgery anyway. A combined laser-iris and cataract surgery is therefore particularly beneficial. Additionally, if a pulse laser system is used that is integrated in the surgical microscope e.g. see FIGS. 49, 50, 51, 52 and 53 then the combination of both surgeries (laser-iris and cataract) can be done in a very efficient way without moving the patient in between and only extending the cataract surgery time by a few minutes or less. The invented method here includes:

Treatment for pigmentary glaucoma or for changing the iris color (lightening it), by using a pulsed laser system, scanning the laser pulses on parts or the entire iris of an eye to treat the iris by removing parts or all of the iris pigmentation. Optionally using a tracking system to compensate for eye movements during the laser treatment. Optionally using a patent eye fixation device to reduce eye movements during the laser treatment. Washing out the anterior chamber after the laser treatment has been completed. Optionally combining the laser treatment with a cataract procedure done in the same surgical session. Optionally using a laser system that is integrated within or mounted underneath a surgical microscope (see FIG. 39, 48 or 50).

The inventions herein may be applied to any eye tissue. Typically, in the case of performing a capsulorexis or capsulotomy the eye tissue comprises a lens capsule. However, in other uses the eye tissue may include but is not limited to the lens, cornea, vitrious, retina, and anterior chamber.

Figure 61:
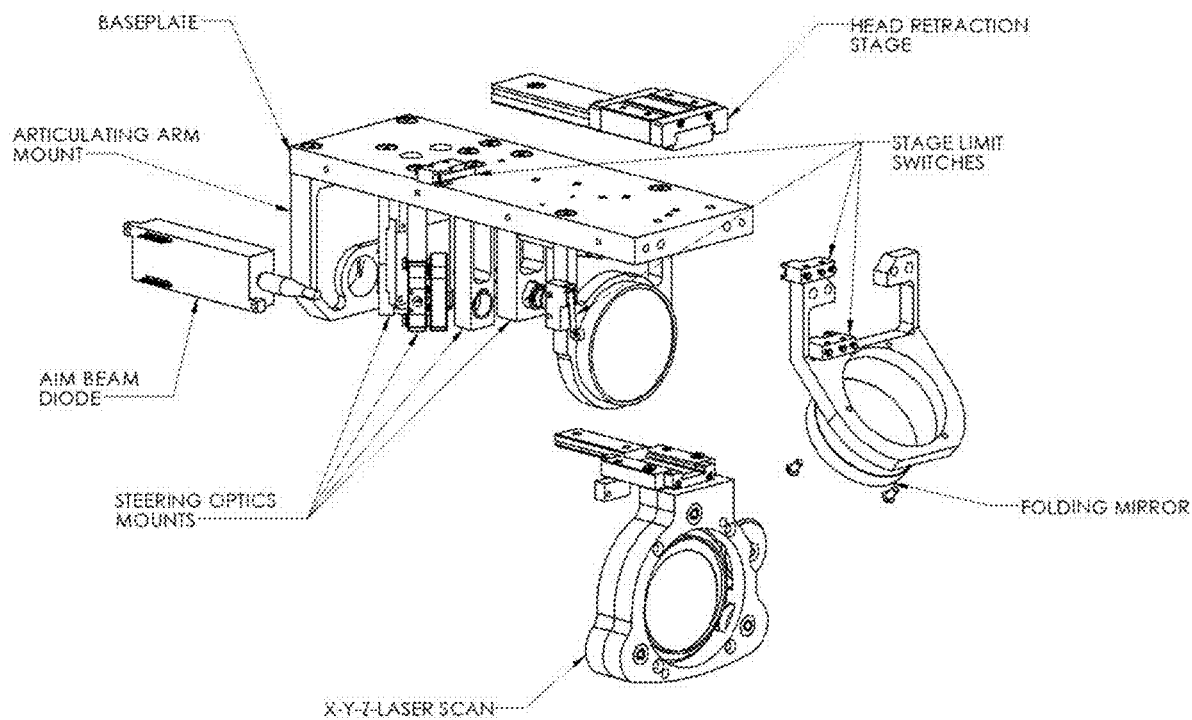
FIG. 61 Exploded component view of a laser delivery system.
Figure 62:
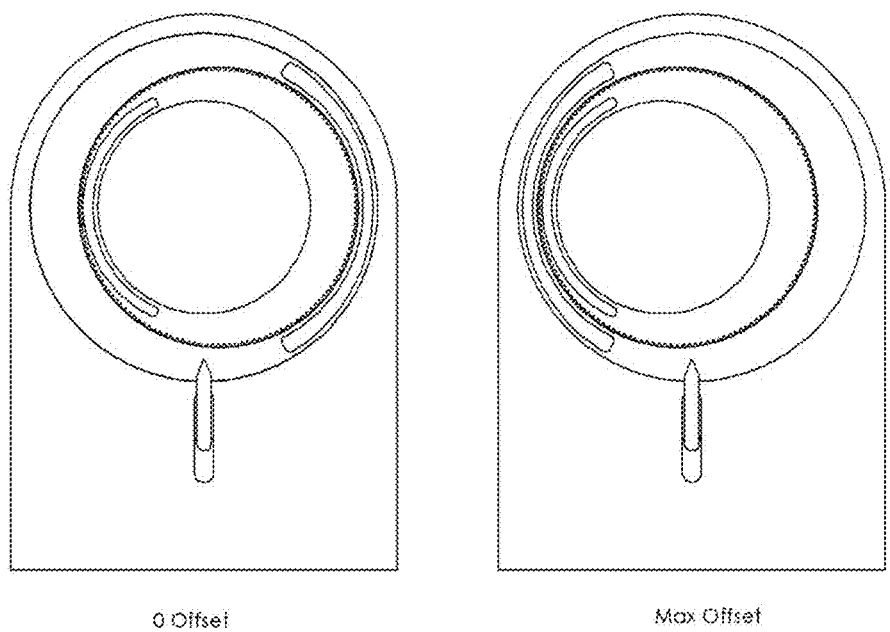
FIG. 62 Shows an adjustable diameter offset rotatable lens mount in its 0 offset and maximum offset position.
Figure 63:
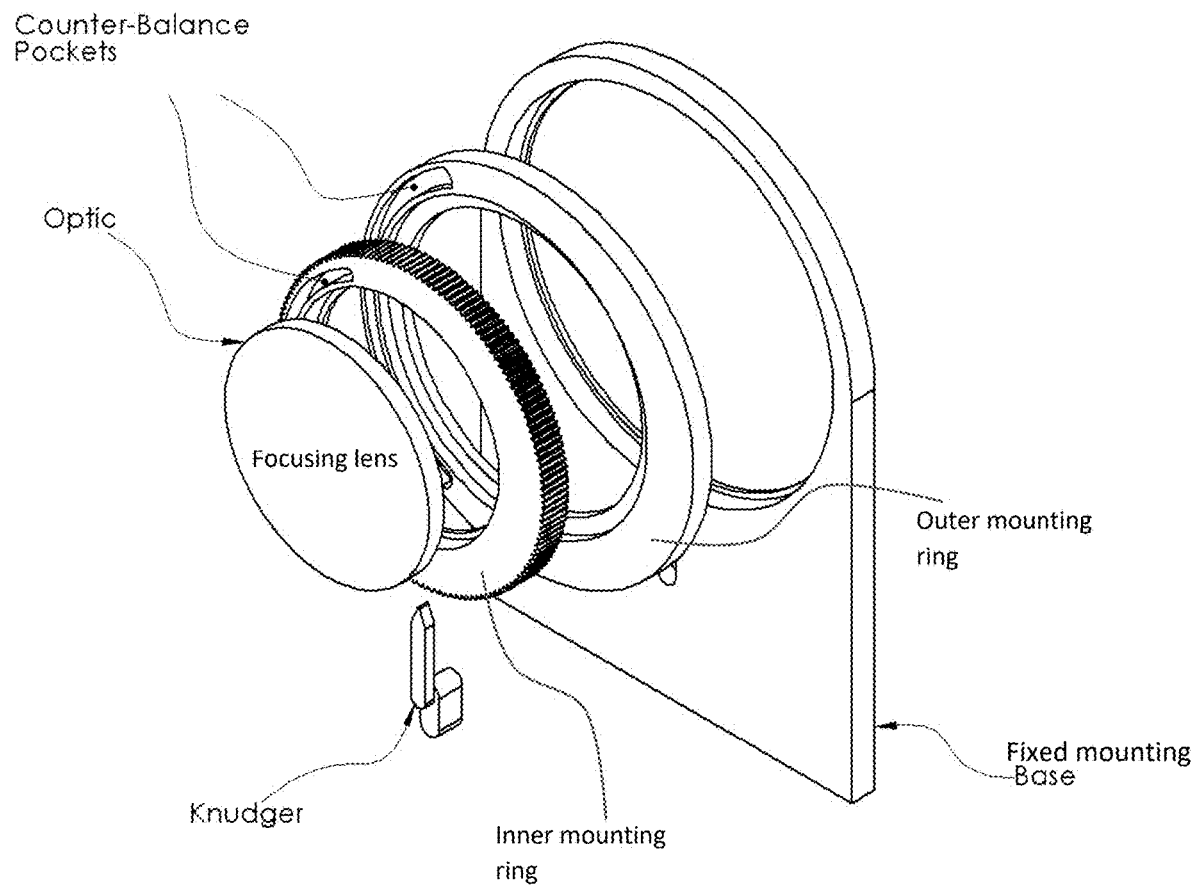
FIG. 63 Shows an exploded view of an adjustable diameter offset rotatable lens mount.

In some embodiments some of the scanning of the laser beam in the laser delivery system that is mounted underneath a surgical microscope is performed through the movements of a focusing optics via a X_Y_Z Laser Scan module as shown in FIG. 61. The folding mirror here corresponds to the final 45 deg mirror in FIG. 23. In one embodiment this laser scan module contains a mechanism to spin a focusing lens in a circular motion therefore allowing a circular scanning pattern in the X and Y dimension. The Z-dimension is scanned via a motorized linear stage that moves the entire movable optics mount back and forward. The spinning lens here is mounted on a fixed offset from the central system axis and therefore performs a laser scan circle with a fixed diameter in the target area of an eye. In another embodiment see FIG. 63, this spinning focusing lens (Laser Scan Module) consist of an inner mounting ring where the focusing lens is mounted into with a predetermined offset from the central axis (here 7 mm offset). This lens-inner mounting subassembly is fully counterweight balance meaning that the localized mounting ring masses and the lens together have a combined center of mass position that falls exactly in the center of the overall subassembly (in this case the circle-center of the outer diameter circumference circle of the inner mounting ring. This inner mounting ring-focusing lens subassembly is now mounted inside a outer mounting ring that has a fitting hole cut out for the inner mounting ring. The circular center of that hole cut out is also offset (here again by 7 mm) compared to the circular center of the outer circumference circle of the outer mounting ring. The combined assembly between focusing lens, inner mounting ring and outer mounting ring is also fully counterbalanced such that the combined center of gravity fall at the exact center of the outer circumference circle of the outer mounting ring. Due to this counterbalancing the entire assembly is being rotated within a fixed outer base (typically interfaced with a rotational ball bearing) without causing any wobble (out of balance) or dynamic de-centricity effect. While the complete assembly rotates inside the fixed base mount, the invented system here allows the focusing lens to be adjusted in the total rotation offset (distance between the center of the lens from the center of the mounting base hole) by rotating the inner mounting ring within the outer mounting ring. The adjustment range is from a minimum: offset amount of the inner mounting ring minus offset amount of outer mounting ring (here 7 mm-7 mm=0 mm) to a maximum: offset amount of the inner mounting ring plus offset amount of outer mounting ring (here 7 mm+7 mm=14 mm) adjustable. FIG. 63 shows some gear teeth feature on the outside of the inner mounting ring that together with the shown Knudger provides a mechanism to rotate the inner mounting ring within the outer mounting ring in a controlled way. Optical encoders on the outside of this assembly are optionally detecting the exact momentary offset adjustment position. Through this varying offset adjustment of the rotating (spinning) focusing lens the laser delivery system achieves the ability to scan the laser focus in the eye in circular patterns with adjustable circular diameters. FIG. 62 shows another view of this mechanism and system with a 0 Offset setting on the left and the max offset setting on the right.

Figure 1:
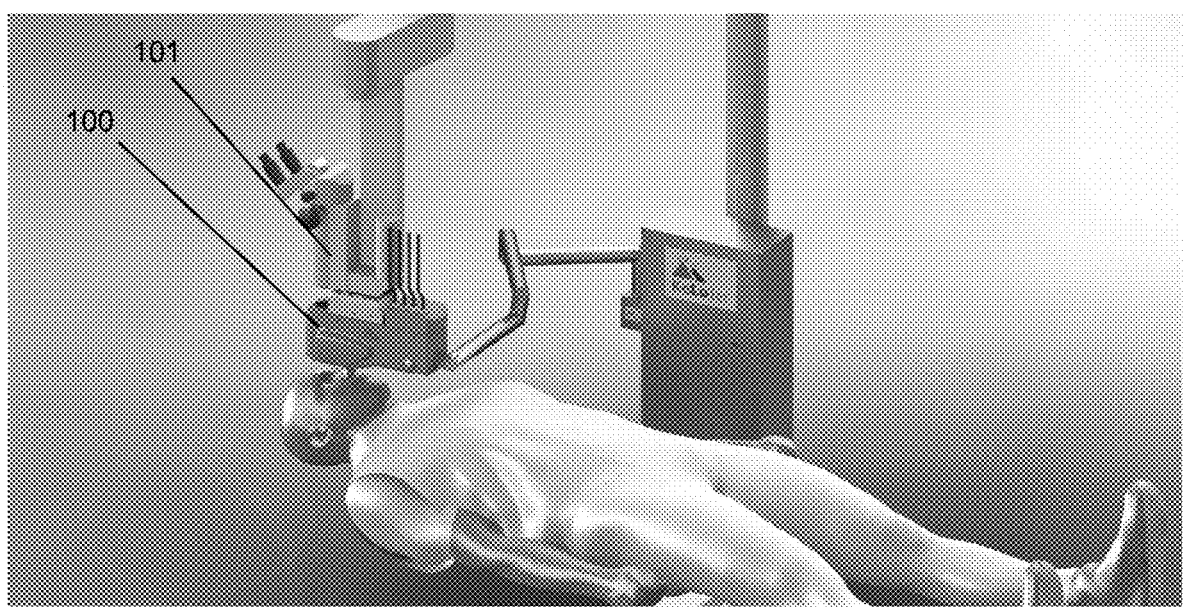
FIG. 1 shows an overview of the laser delivery system in blue mounted under a surgical microscope.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 shows an overview of the laser delivery system 100 mounted under a surgical microscope 101.

FIG. 2 shows a sequence 200 of 2 laser pulses 201, 202 being delivered with a controlled spacing that results in bubble 201a, 202a, separation.

FIG. 3 shows a circular laser 300 pulse sequence scan.

Figure 4:
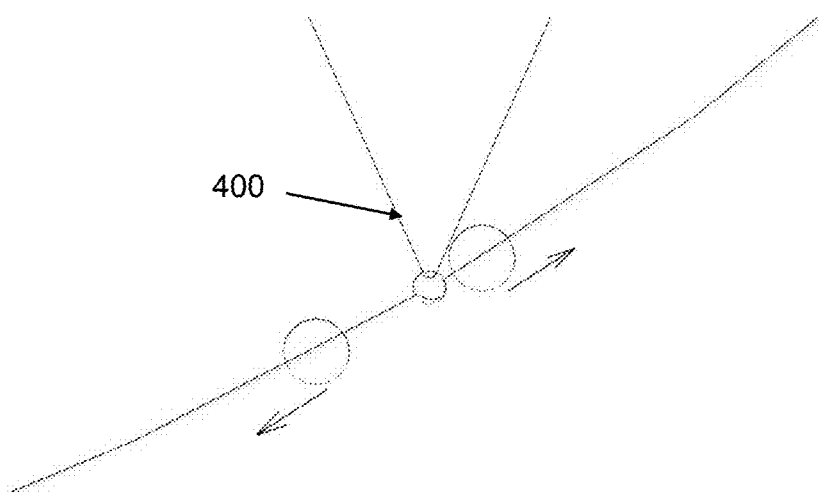
FIG. 4 shows a closeup of laser pulses delivered in a time sequence and with controlled spacing.

FIG. 4 shows a closeup of laser 400 pulses delivered in a time sequence and with controlled spacing.

FIG. 5 shows a top view of the bubble dynamic for a spatially controlled laser 500 pulse sequence 501.

FIG. 6 shows a detailed view 2 laser pulses 600, 602 sequenced in time and controlled in spacing and resulting in bubble 600a, 602a interference 603 that leads to a dynamic bubble movement.

FIG. 7 same as FIG. 6 but with another later stage on the bottom.

Figure 8:
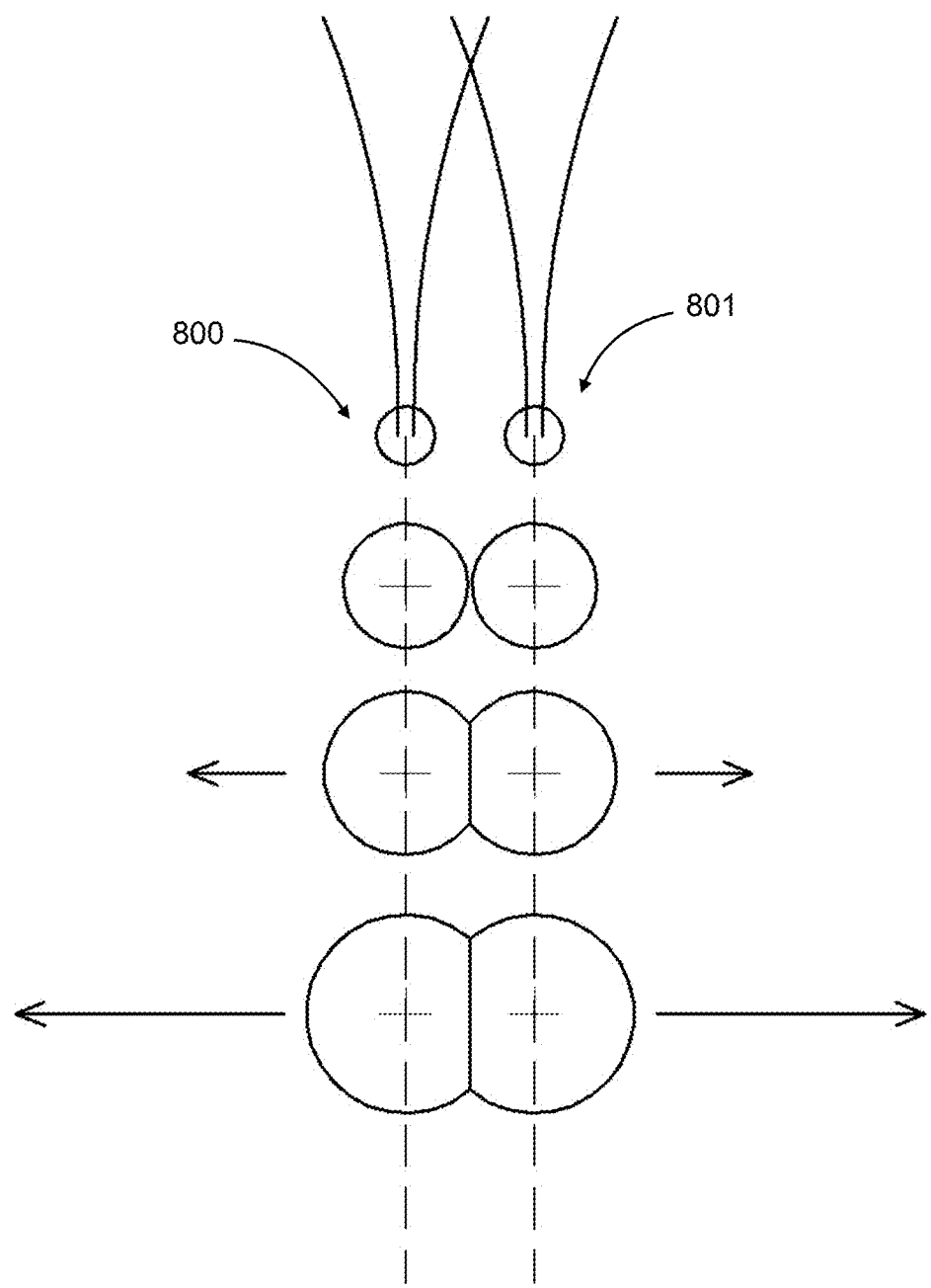
FIG. 8 shows the interaction of 2 simultaneously created laser focus cavitation bubbles, that are spaced to create a dynamic interference.

FIG. 8 shows the interaction of 2 simultaneously created laser focus cavitation bubbles 800, 801, that are spaced to create a dynamic interference.

FIG. 9 shows a full cylindrical laser scanning pattern 900 cutting a tilted capsule of an eye.

FIG. 9B shows a full cylindrical laser scanning pattern 910 cutting a non tilted capsule of an eye.

FIG. 10 shows a "on" and "off" modulated laser scanning pattern 1001 cutting a tilted capsule of an eye with far less laser pulses compared to FIG. 9.

FIG. 11 shows a time sequence top view of the pattern cut in FIG. 10.

Figure 12:
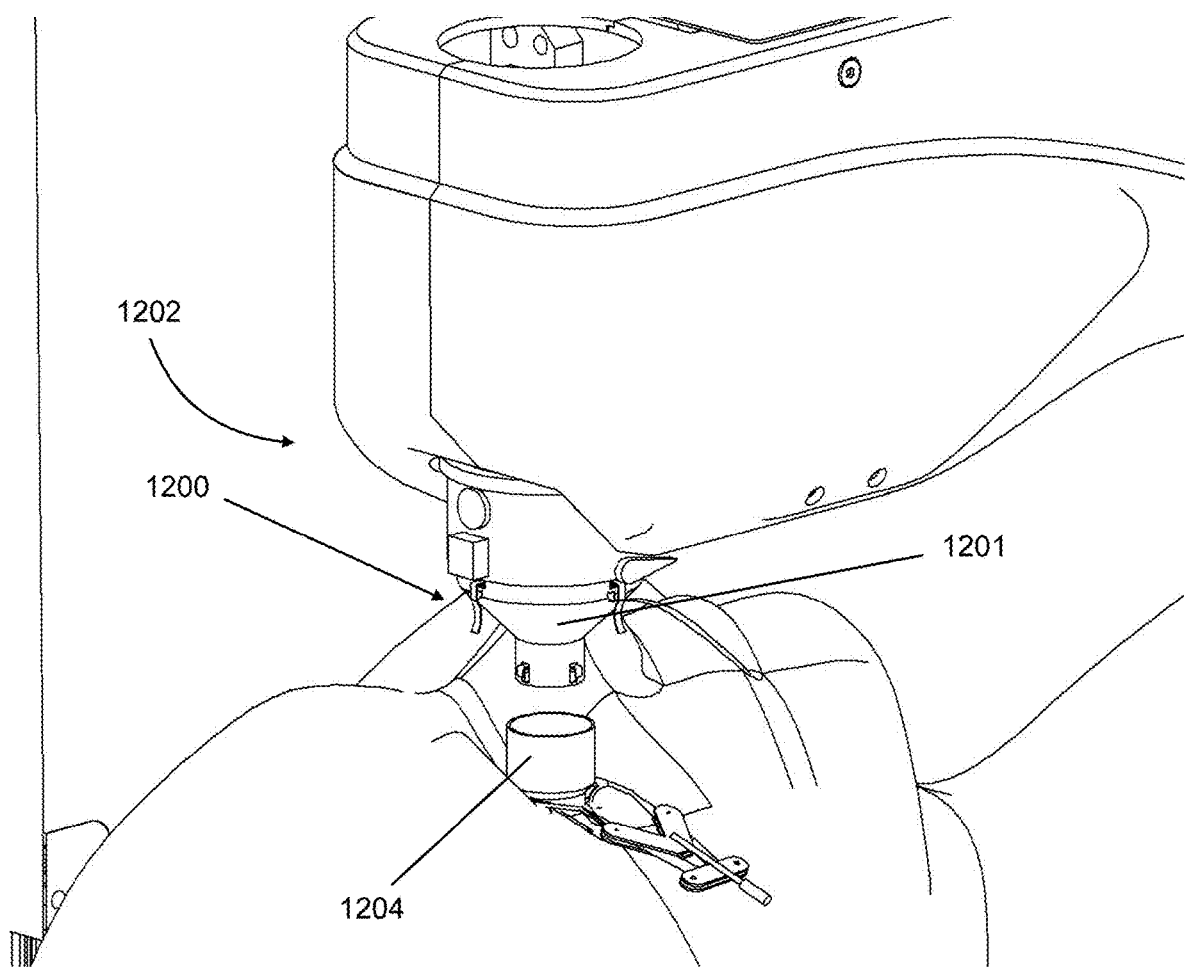
FIG. 12 Shows a docking system consisting of a cone piece attached to the laser delivery system and a cylindrical receptive piece attached to the patient eye.

FIG. 12 Shows a docking system 1200 consisting of a cone piece 1201 attached to the laser delivery system 1202 and a cylindrical receptive piece 1204 attached to the patient eye.

Figure 13:
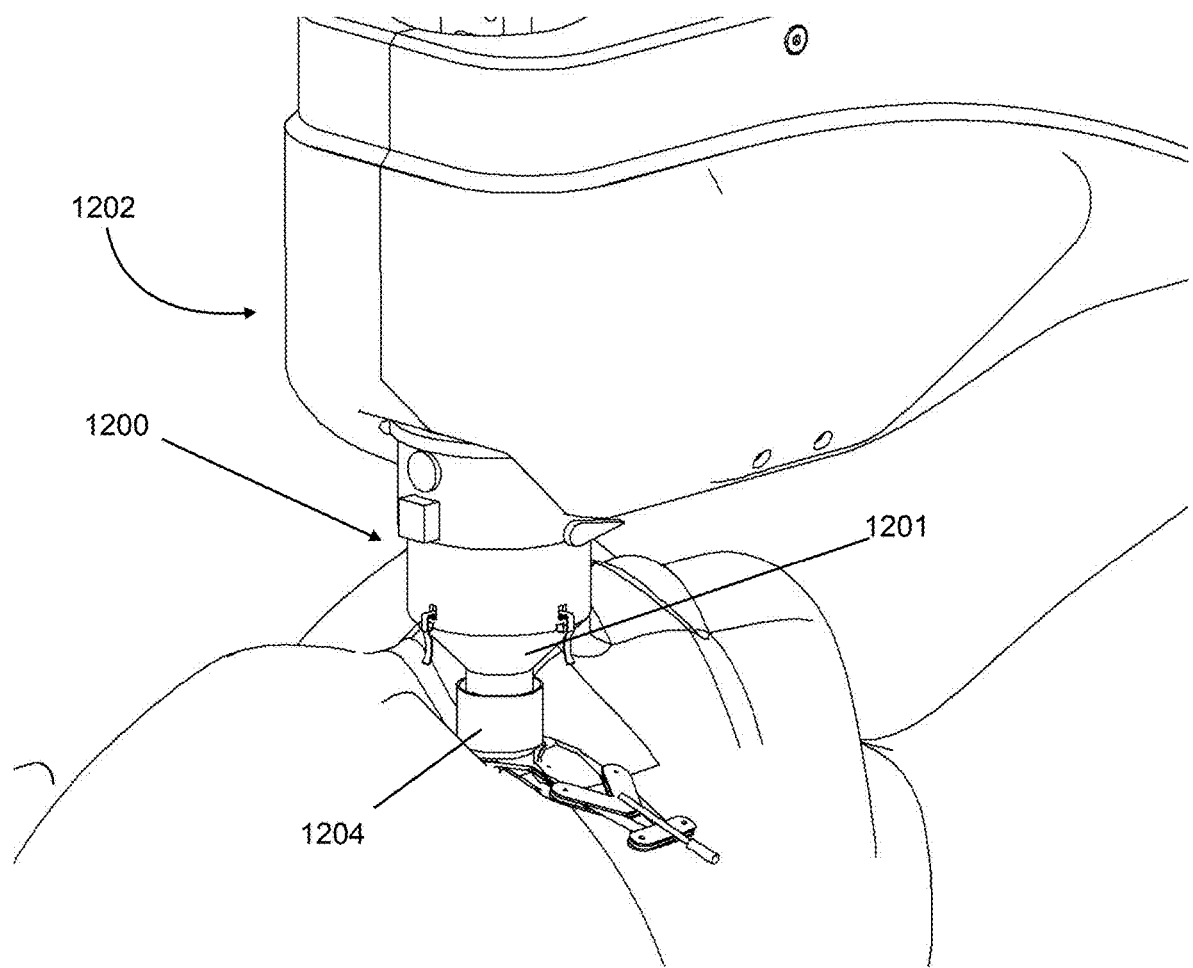
FIG. 13 Shows the docking systems pieces from FIG. 12 engaged in a docking configuration.

FIG. 13 Shows the docking systems pieces from FIG. 12 engaged in a docking configuration.

Figure 14:
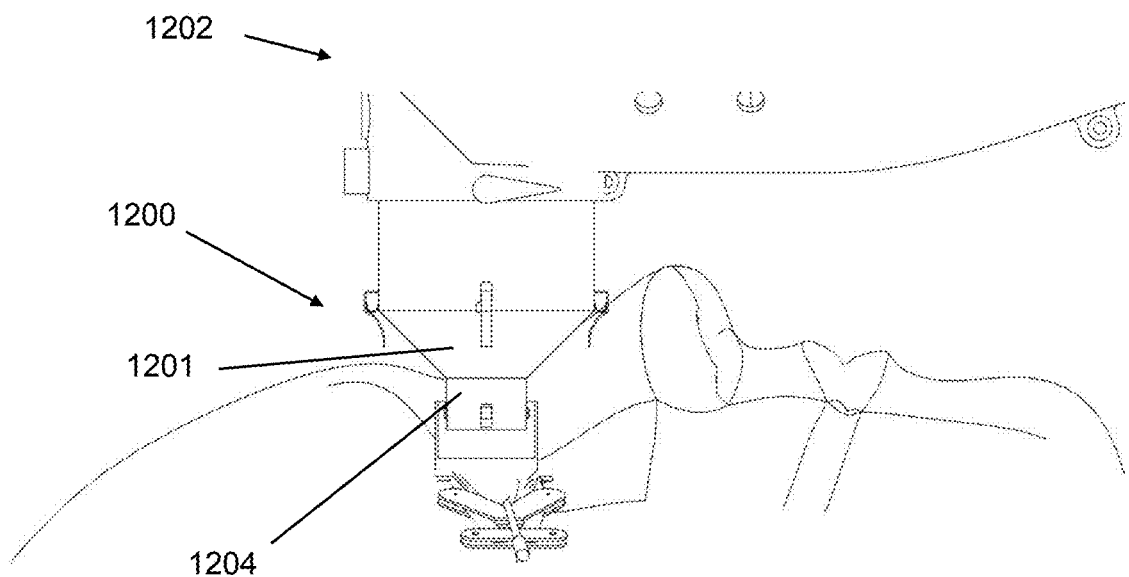
FIG. 14 shows a side/cross-sectional view of FIG. 13.

FIG. 14 shows a side/cross-sectional view of FIG. 13.

FIG. 15 shows a side/cross-sectional view of FIG. 12.

FIG. 16 shows close up of FIG. 14.

Figure 17:
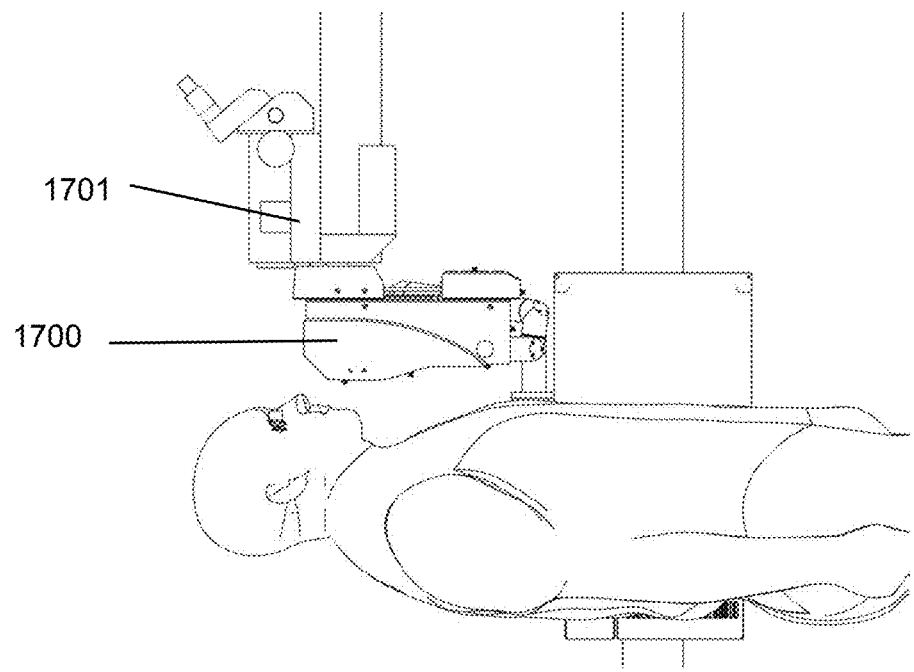
FIG. 17 shows a laser delivery system attached under a microscope in the "out" position.

FIG. 17 shows a laser delivery system 1700 attached under a microscope 1701 in the "out" position.

Figure 18:
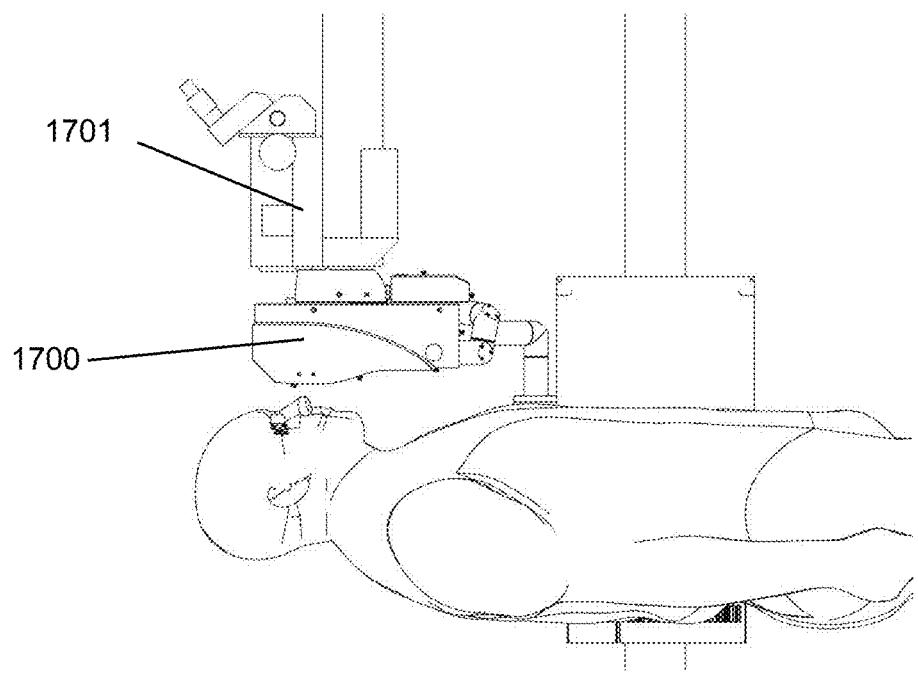
FIG. 18 shows a laser delivery system attached under a microscope in the "in" position.

FIG. 18 shows a laser delivery system 1700 attached under a microscope 1701 in the "in" position.

Figure 19:
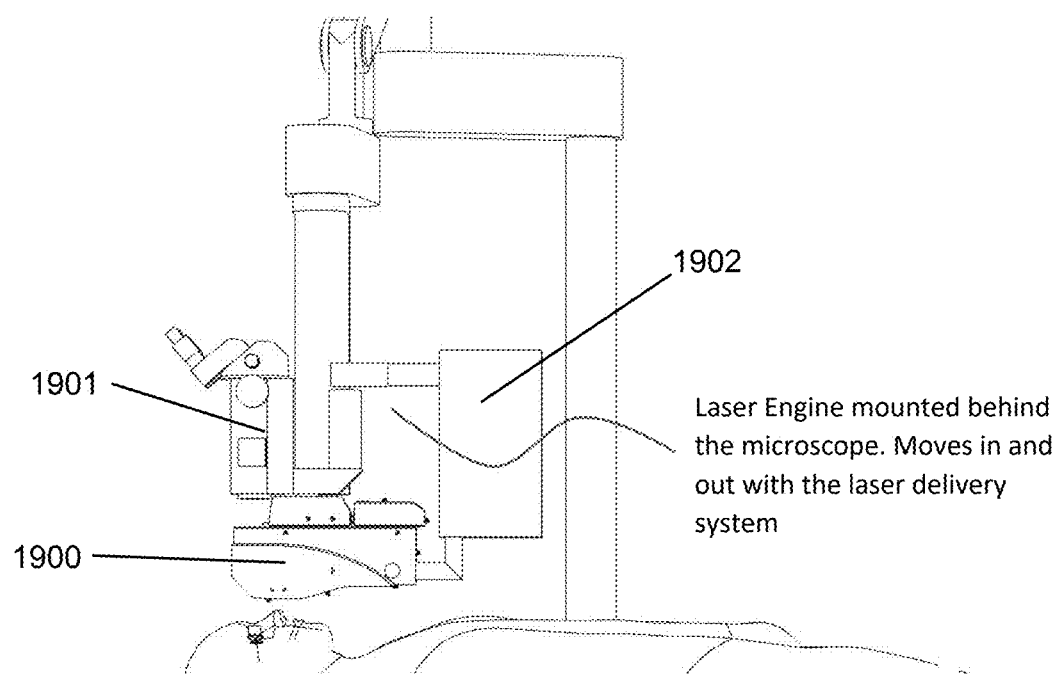
FIG. 19 shows a laser delivery system attached under a microscope in the "in" position with the laser engine mounted behind the microscope.

FIG. 19 shows a laser delivery system 1900 attached under a microscope 1901 in the "in" position with the laser engine 1902 mounted behind the microscope.

Figure 20:
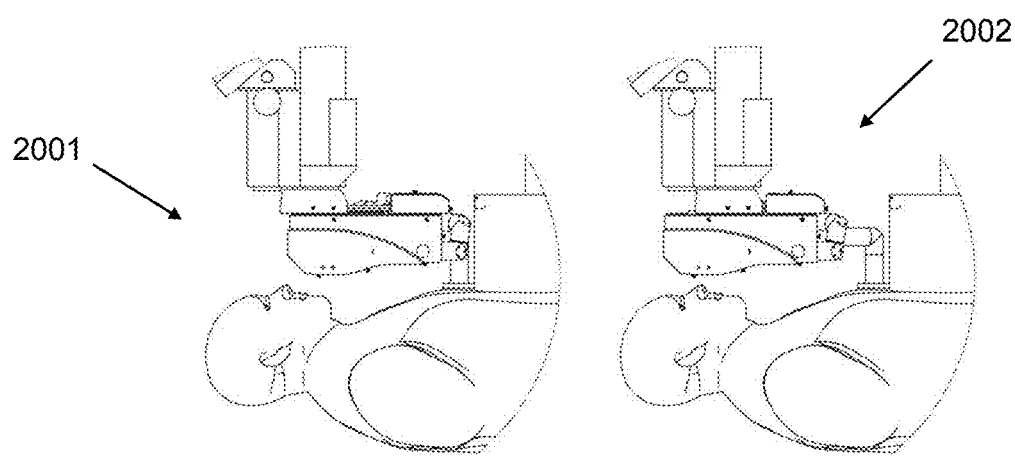

FIG. 20 shows a laser delivery system out 2001 and in 2002.

FIG. 21 shows a laser delivery system mounted under the microscope without skins.

FIG. 22 shows a laser delivery system mounted under the microscope without skins.

FIG. 23 shows a laser delivery system mounted under the microscope without skins.

FIG. 24 shows a laser delivery system mounted under the microscope without skins.

Figure 25:
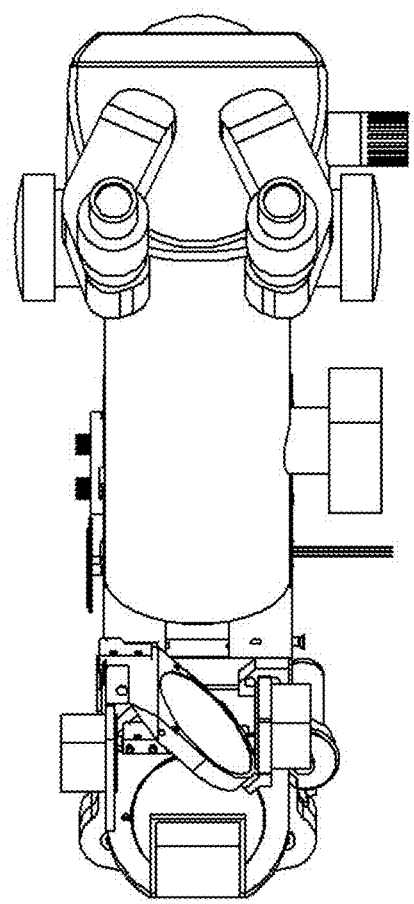
FIG. 25 shows a laser delivery system mounted under the microscope in top view.

FIG. 25 shows a laser delivery system mounted under the microscope in top view.

FIG. 26 shows an optical setup.

FIG. 27 shows an optical setup for the confocal scanning feedback signal.

FIG. 27B shows an optical setup for the confocal scanning feedback signal.

Figure 28:
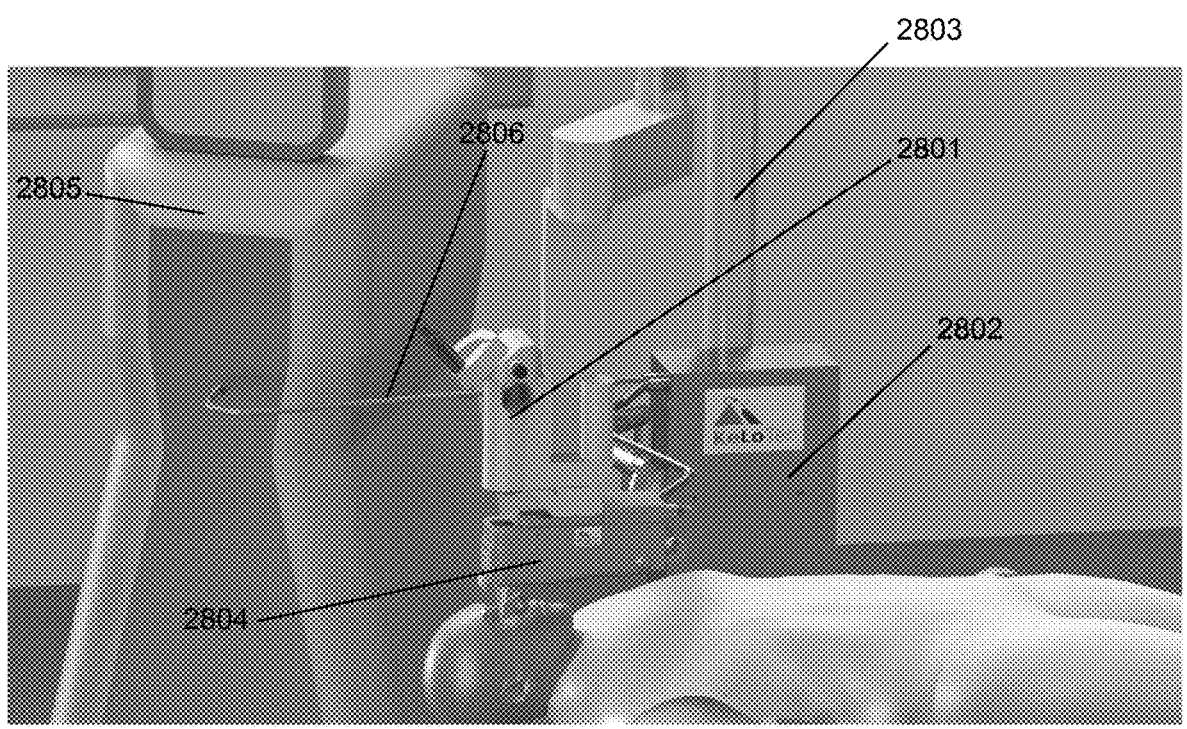
FIG. 28 shows an OR setup with microscope, laser engine mounted on microscope pole, laser delivery system mounted under the microscope and a phaco system on the left side that also has a cable connection to the laser engine control box and thereby controls the laser system.

FIG. 28 shows an OR setup with microscope 2801, laser engine 2802 mounted on microscope pole 2803, laser delivery system 2804 mounted under the microscope and a phaco system 2805 on the left side that also has a cable connection 2806 to the laser engine control box and thereby controls the laser system.

Figure 29:
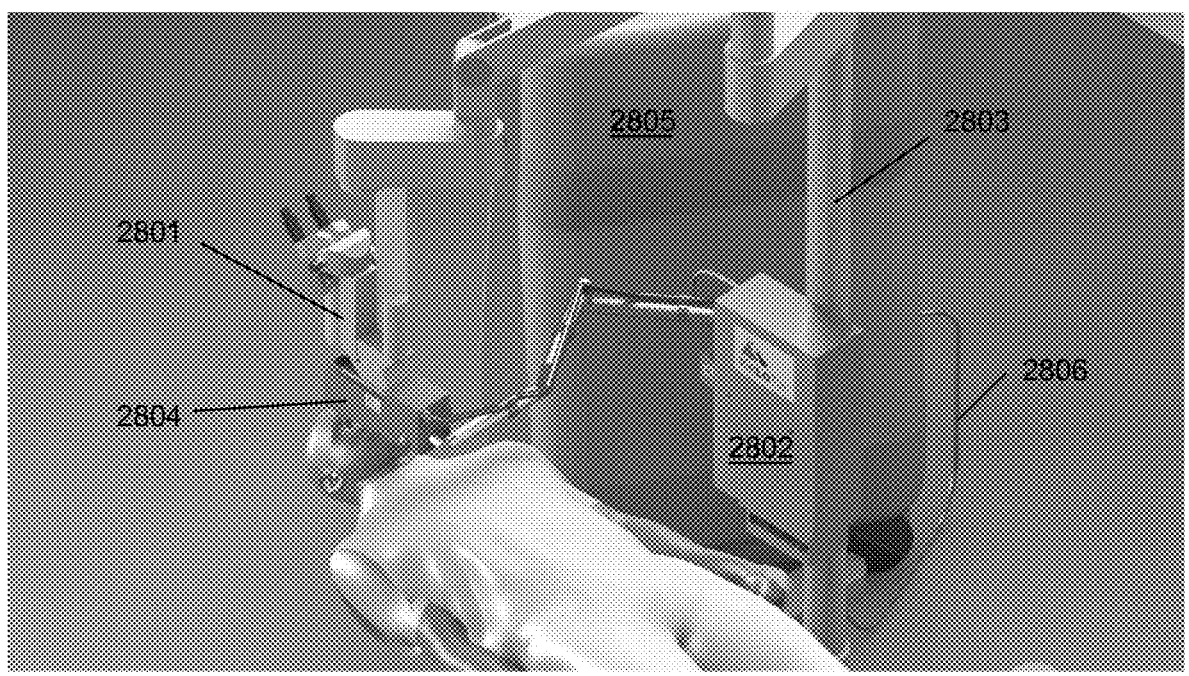
FIG. 29 same setup as FIG. 28 with different view angle

FIG. 29 same setup as FIG. 28 with different view angle.

Figure 30:
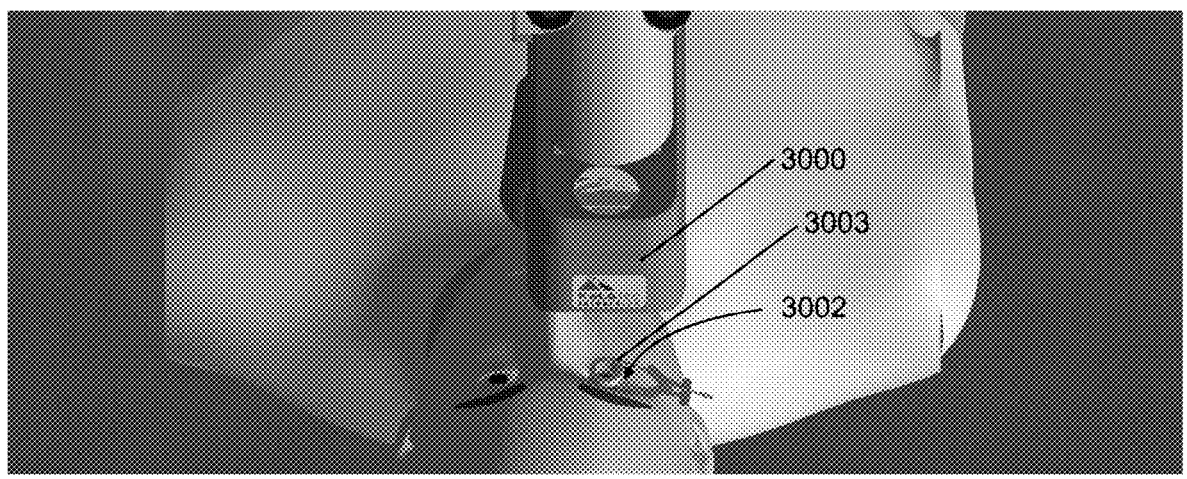
FIG. 30 shows the laser delivery system and the patient eye with a patient interface fixated to the eye.

FIG. 30 shows the laser delivery system 3000 and the patient eye 3002 with a patient interface 3003 fixated to the eye.

Figure 31:
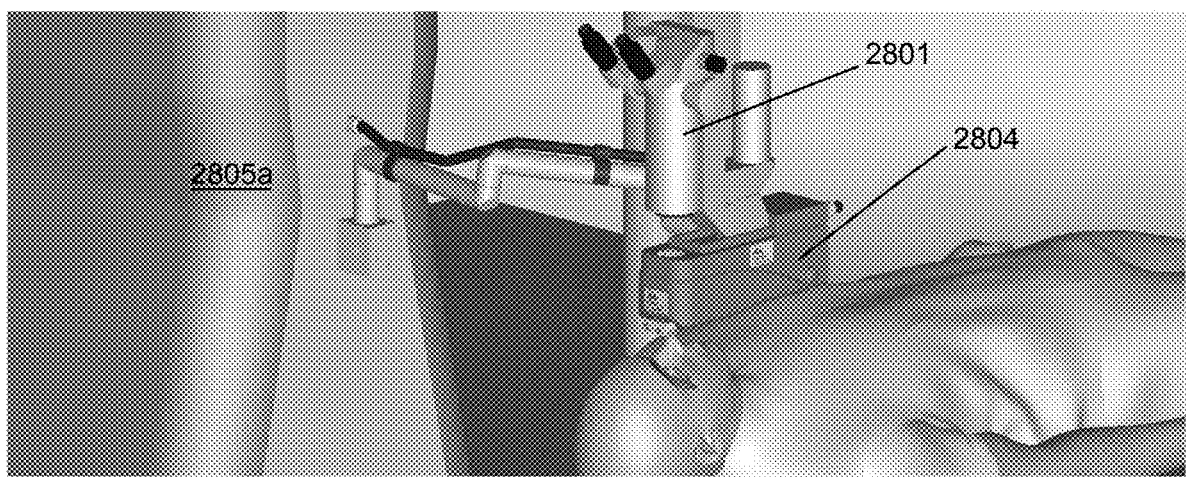
FIG. 31 shows a setup as in FIG. 28 were the laser engine is fully integrated and mounted inside the phaco emulsification unit.

FIG. 31 shows a setup as in FIG. 28 were the laser engine is fully integrated and mounted inside the phaco emulsification unit 2805a.

FIG. 32 shows same system as in FIG. 31 with the laser delivery system in the "out" position.

FIG. 33 shows a close up of FIG. 31.

Figure 34:
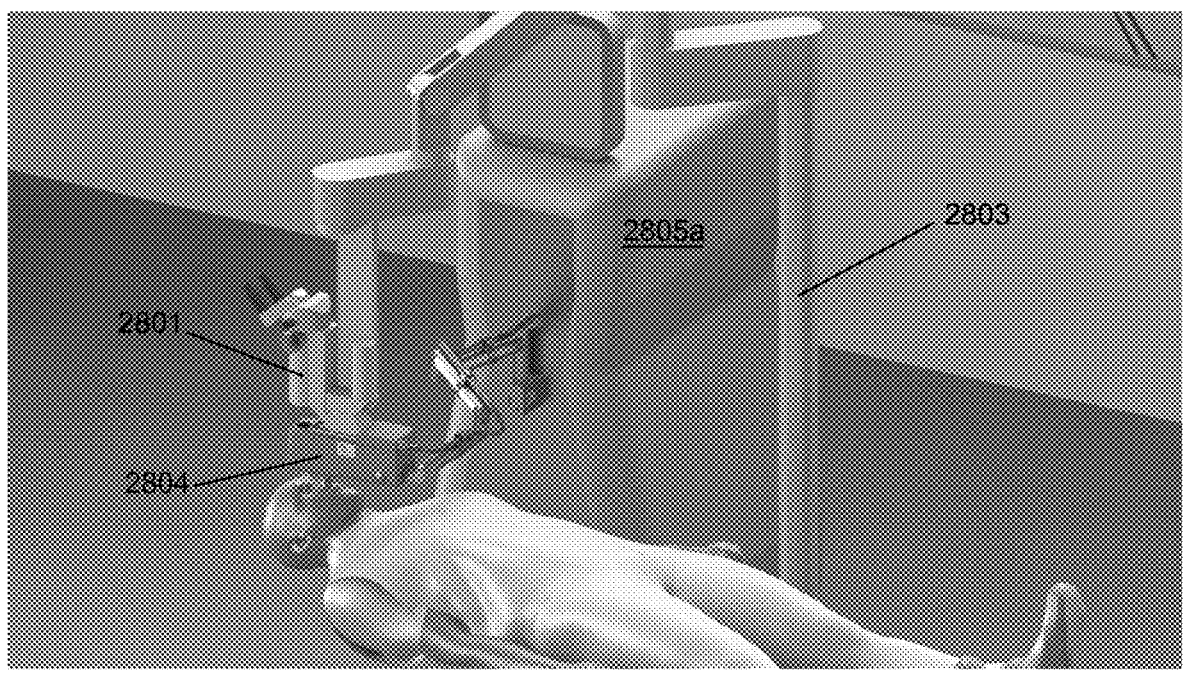
FIG. 34 shows a different view angle of FIG. 33.

FIG. 34 shows a different view angle of FIG. 33.

Figure 35:
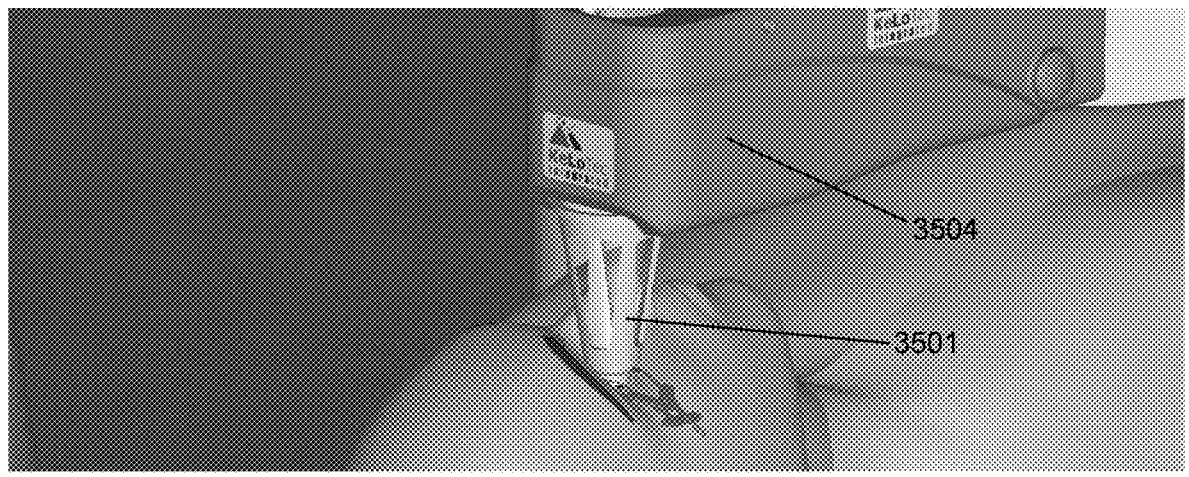
FIG. 35 shows a docking piece between the eye and the laser delivery system

FIG. 35 shows a docking piece 3501 between the eye and the laser delivery system 3504

Figure 36:
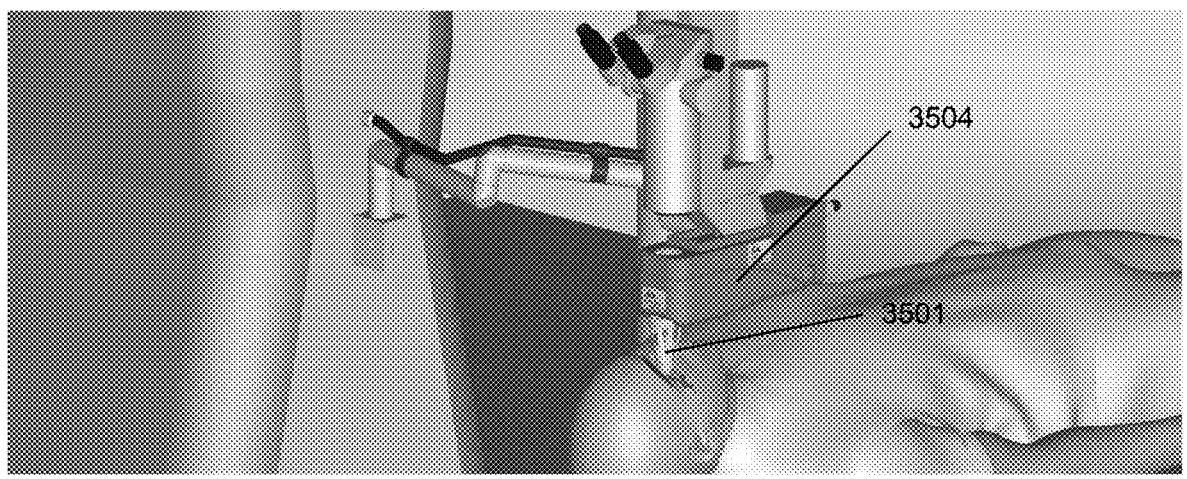
FIG. 36 shows same as FIG. 35 with a different view angle.

FIG. 36 shows same as FIG. 35 with a different view angle.

Figure 37:
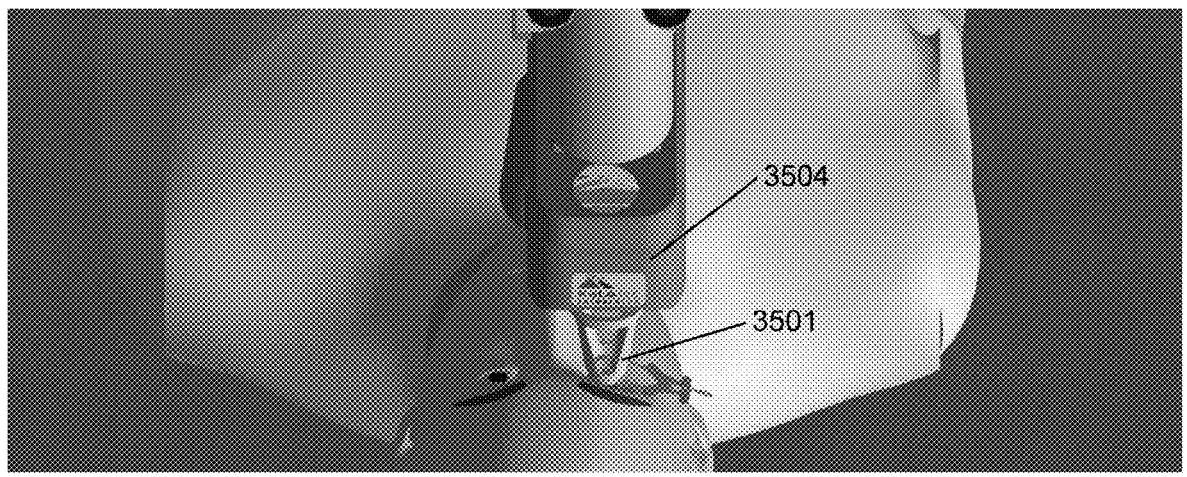
FIG. 37 shows same as FIG. 35 with a different view angle.

FIG. 37 shows same as FIG. 35 with a different view angle.

Figure 38:
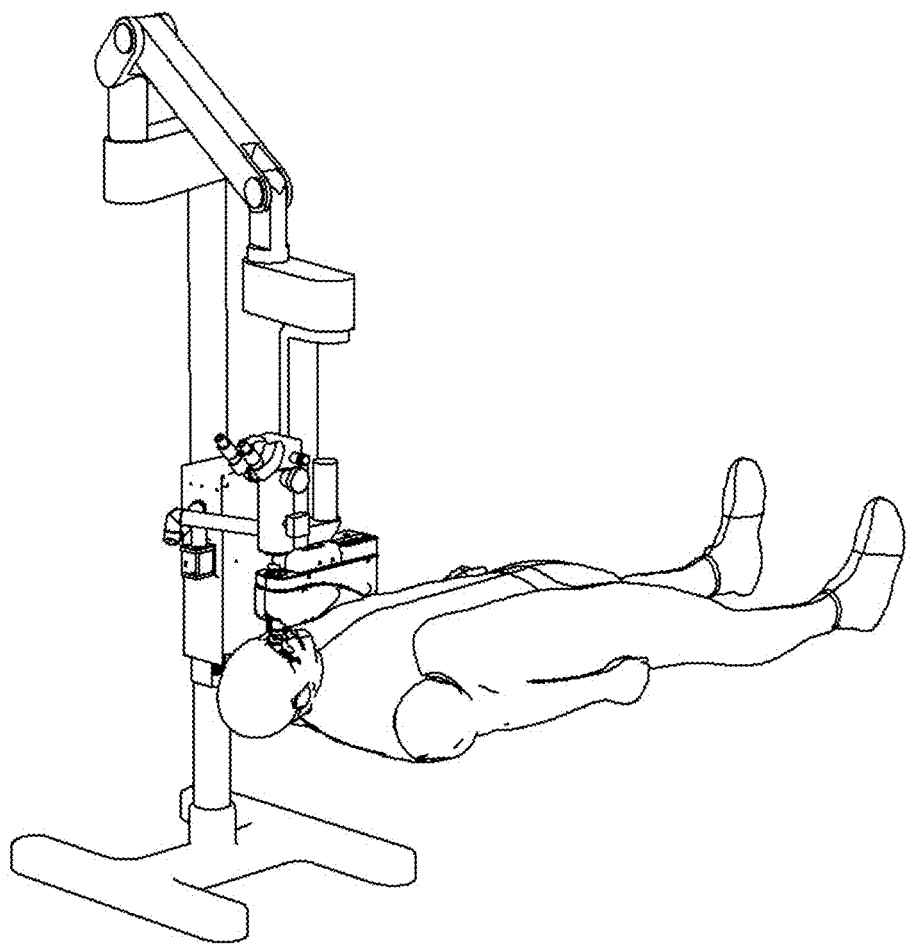
FIG. 38 shows a system overview.

FIG. 38 shows a system overview.

Figure 39:
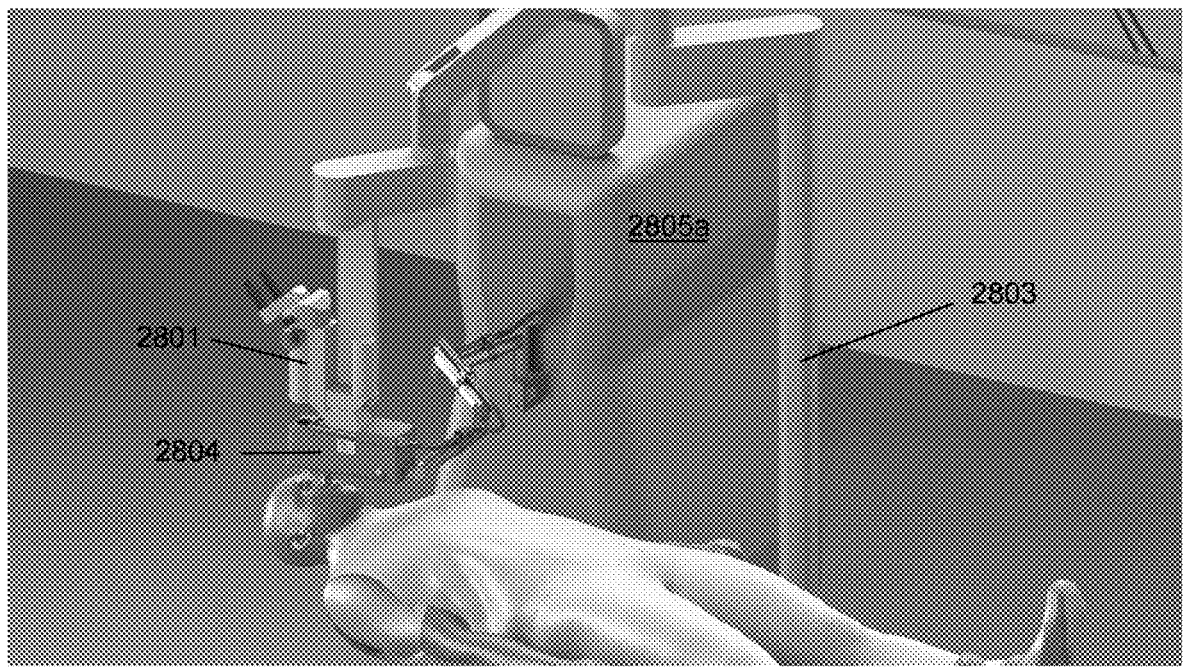
FIG. 39 shows the same as FIG. 34.

FIG. 39 shows the same as FIG. 34.

Figure 40:
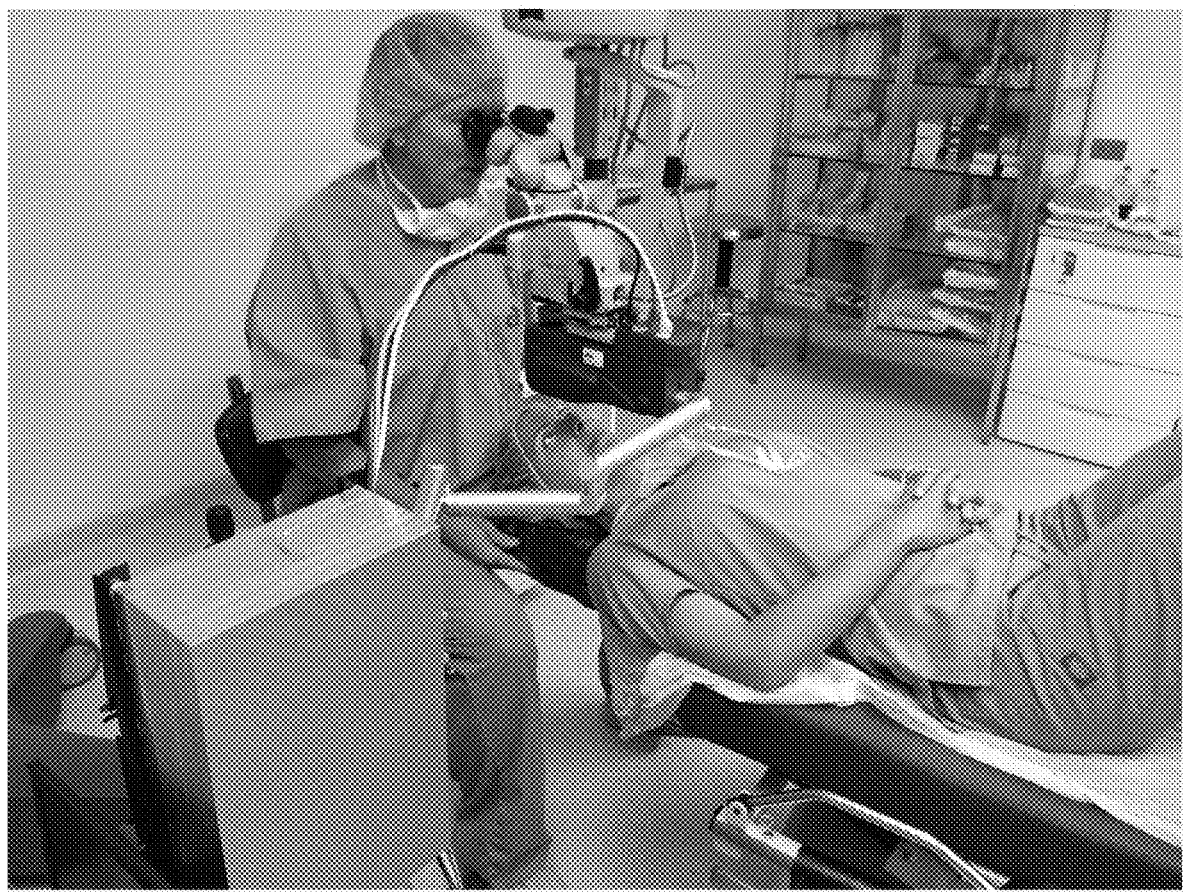
FIG. 40 shows an actual OR setup

FIG. 40 shows an actual OR setup

Figure 41:
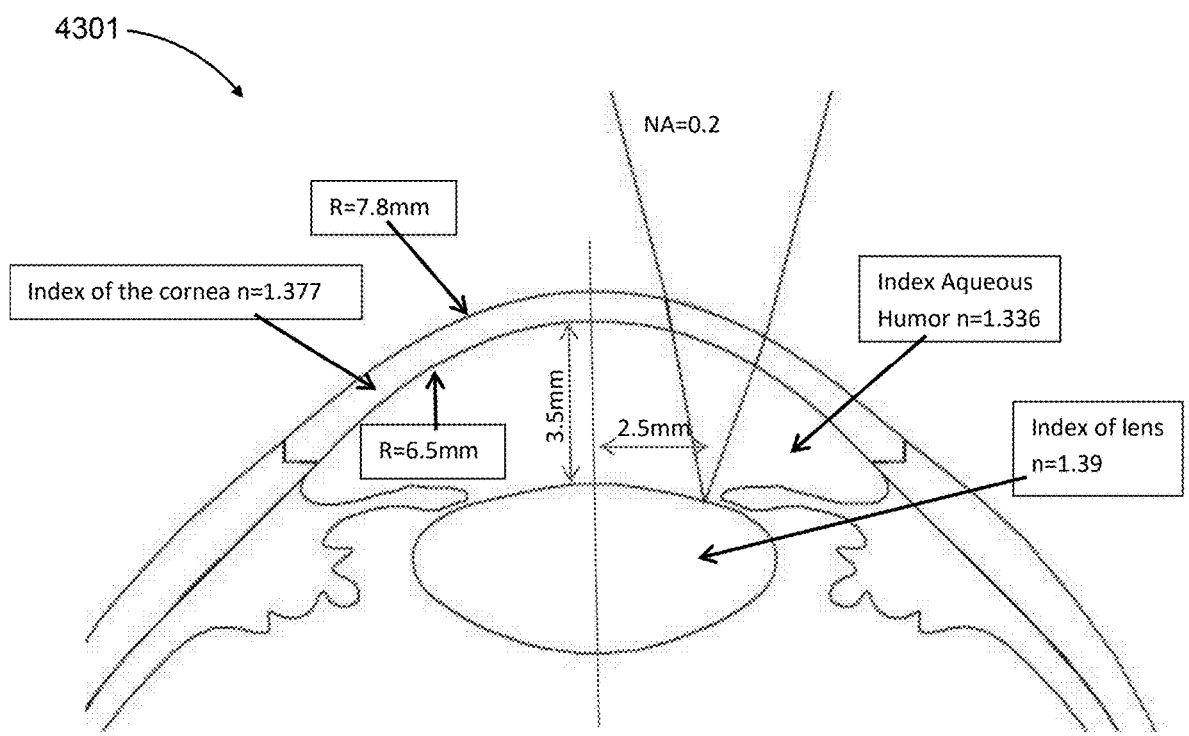
FIG. 41 shows a cross section through a human eye.

FIG. 41 shows a cross section through a human eye.

Figure 42:
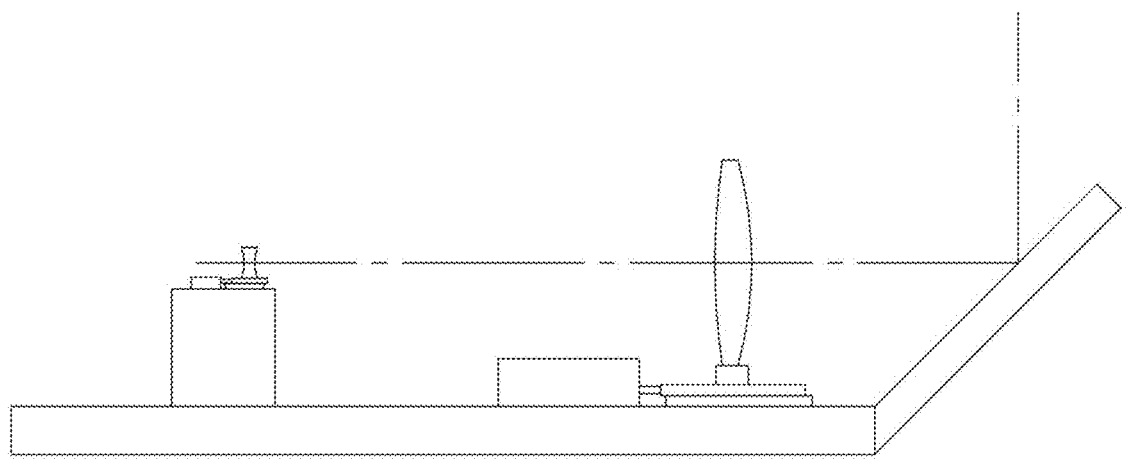
FIG. 42 shows an optical setup.

FIG. 42 shows an optical setup.

Figure 43:
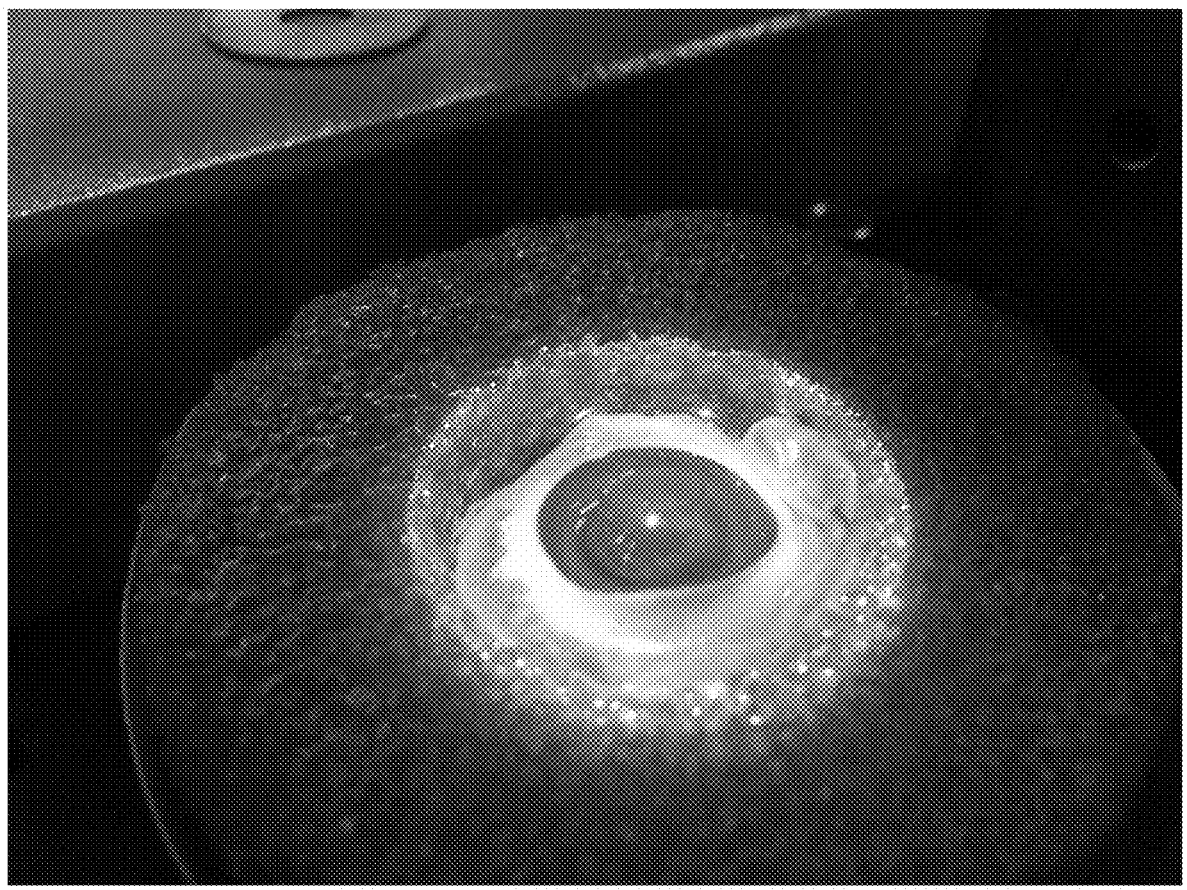

FIG. 43 shows a pig eye under the laser delivery system with the visible targeting laser beam on.

Figure 44:
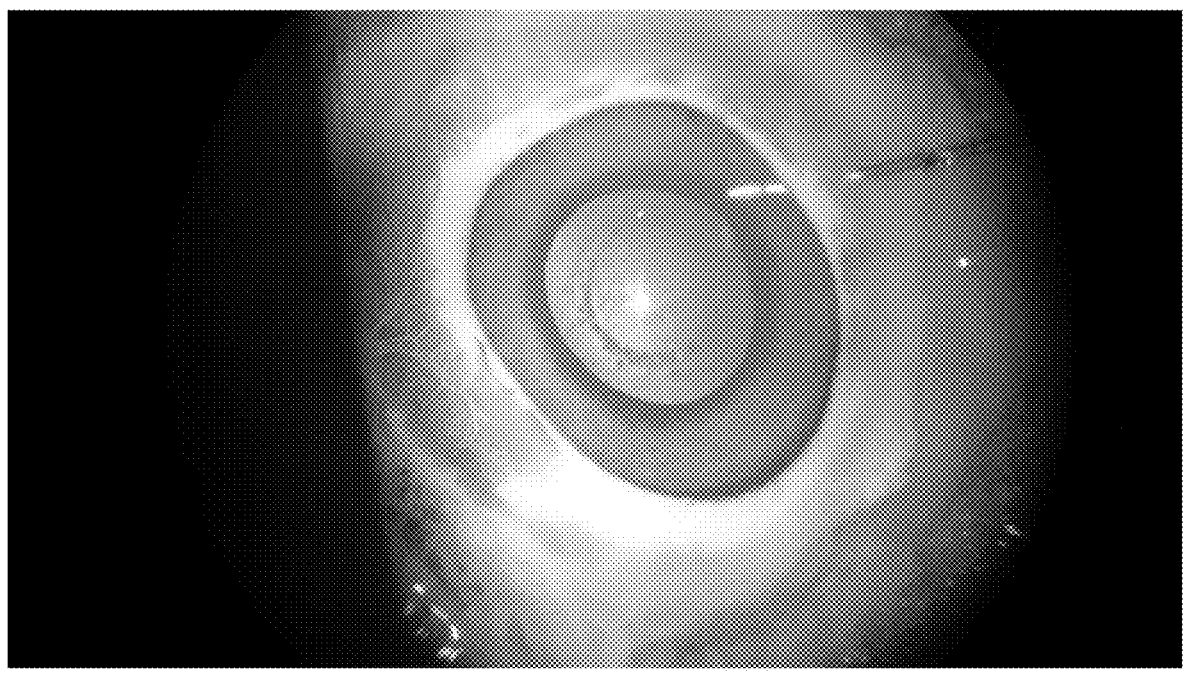
FIG. 44 shows a pig eye after a laser capsulotomy cut was completed.

FIG. 44 shows a pig eye after a laser capsulotomy cut was completed.

Figure 45:
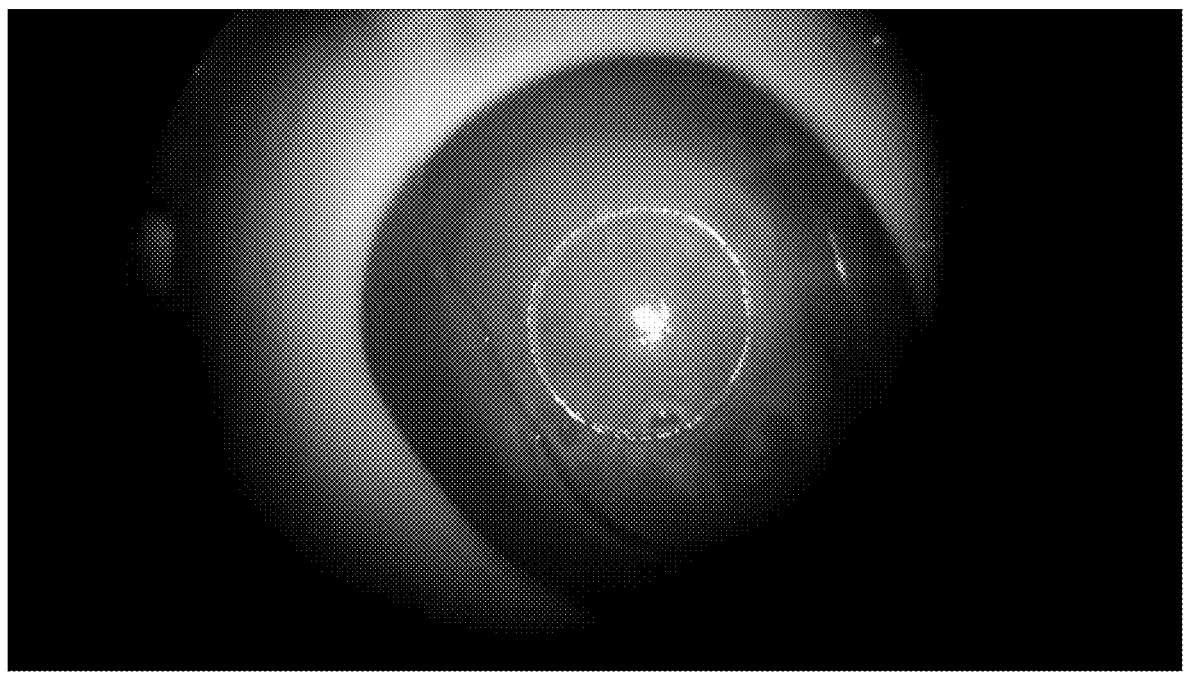
FIG. 45 shows a pig eye after a laser capsulotomy cut was completed.

FIG. 45 shows a pig eye after a laser capsulotomy cut was completed.

Figure 46:
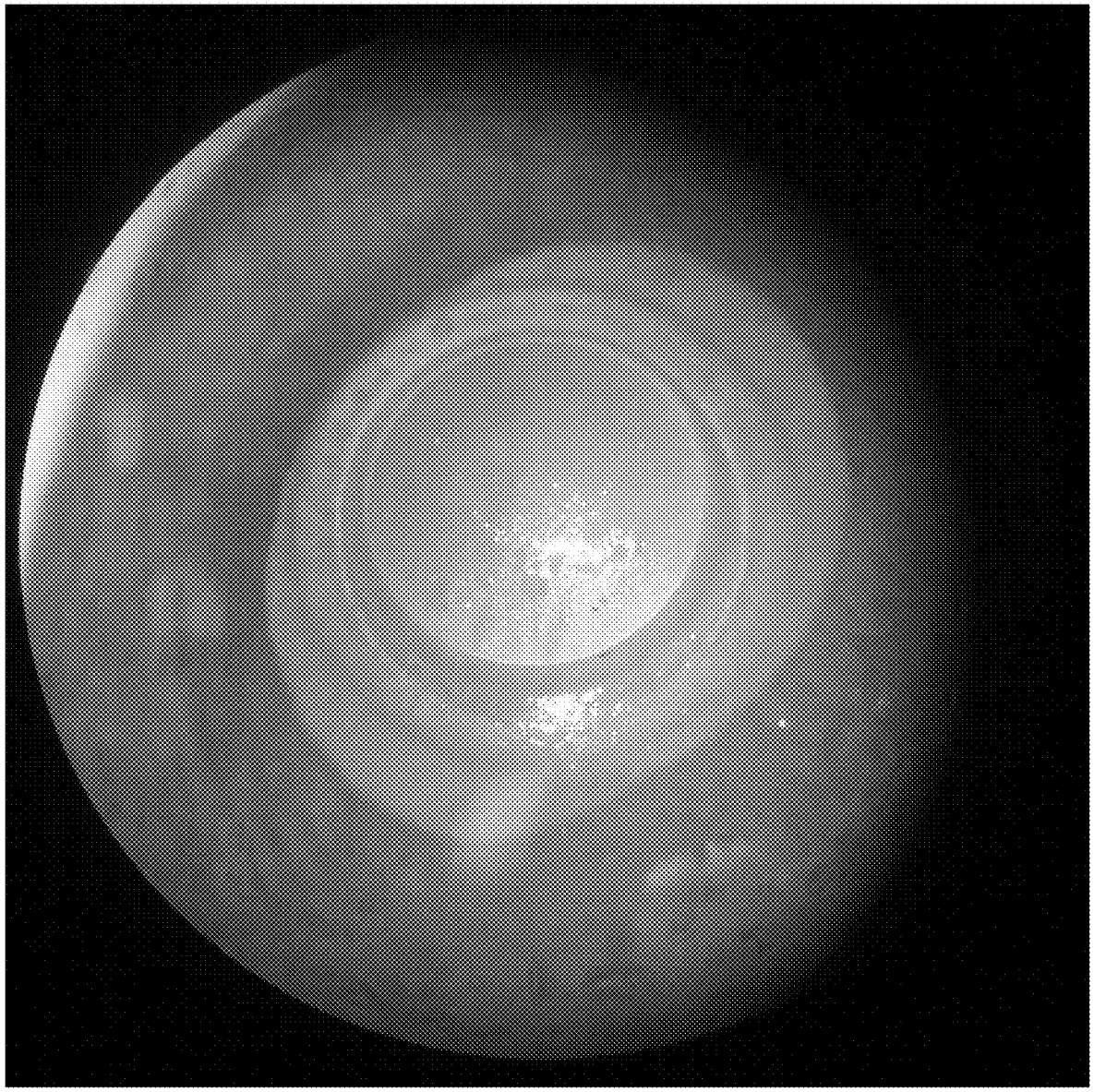
FIG. 46 shows a pig eye after a laser capsulotomy cut was completed.

FIG. 46 shows a pig eye after a laser capsulotomy cut was completed.

Figure 47:
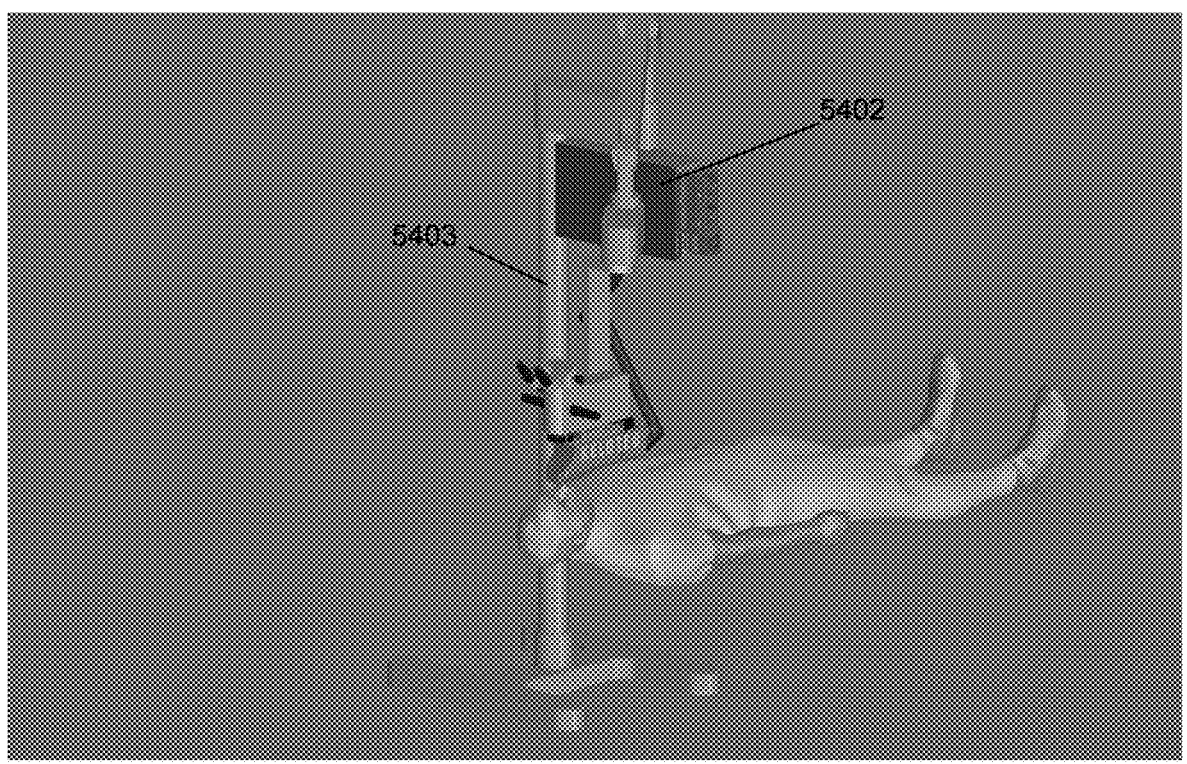
FIG. 47 shows the system setup with the laser engine mounted high up on the microscope arm.

FIG. 47 shows the system setup with the laser engine 5402 mounted high up on the microscope arm 5403.

Figure 48:
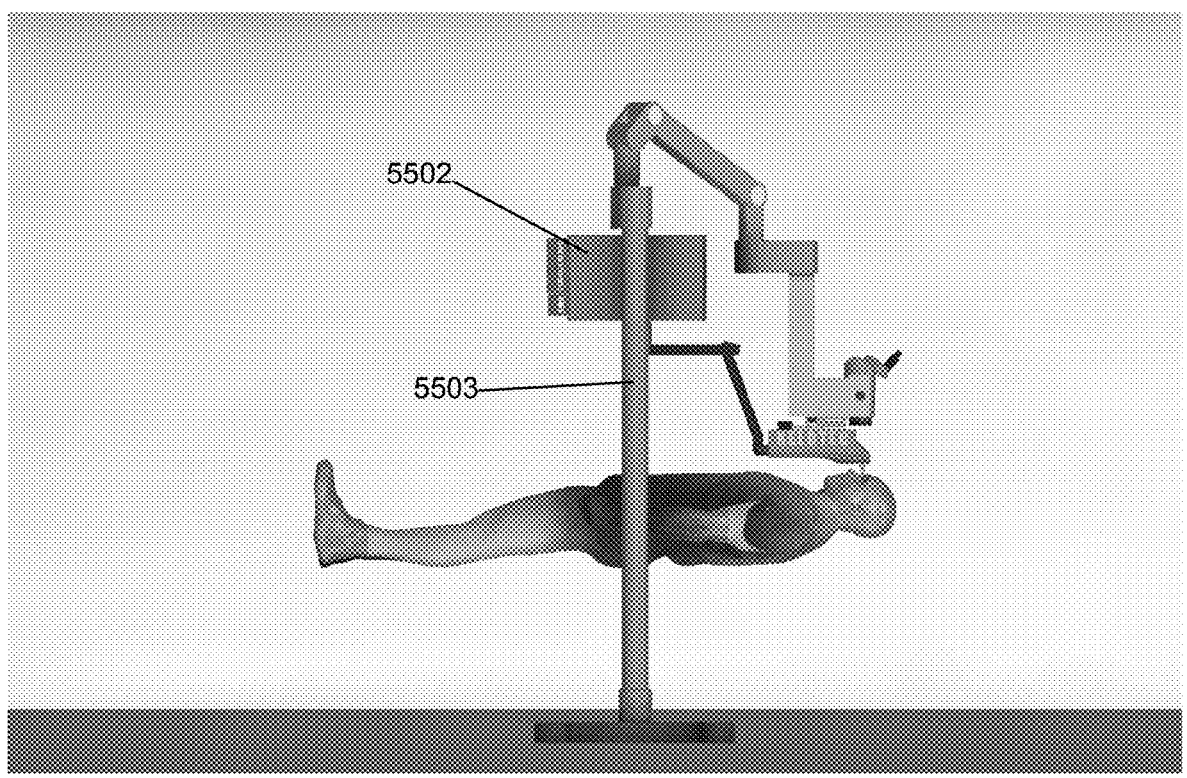
FIG. 48 same as FIG. 54 with different view angle.

FIG. 48 same as FIG. 54 with different view angle.

Figure 49:
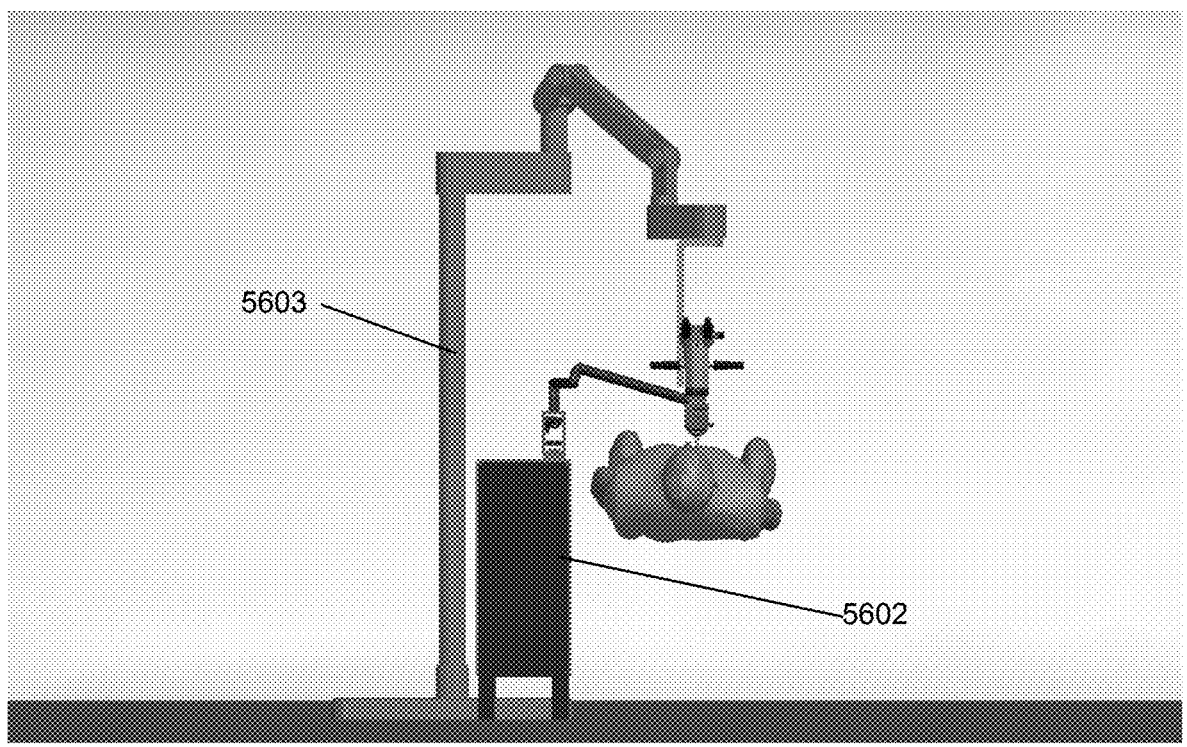
FIG. 49 shows a system setup with the laser engine box standing next to the microscope stand.

FIG. 49 shows a system setup with the laser engine box 5602 standing next to the microscope stand 5603.

Figure 50:
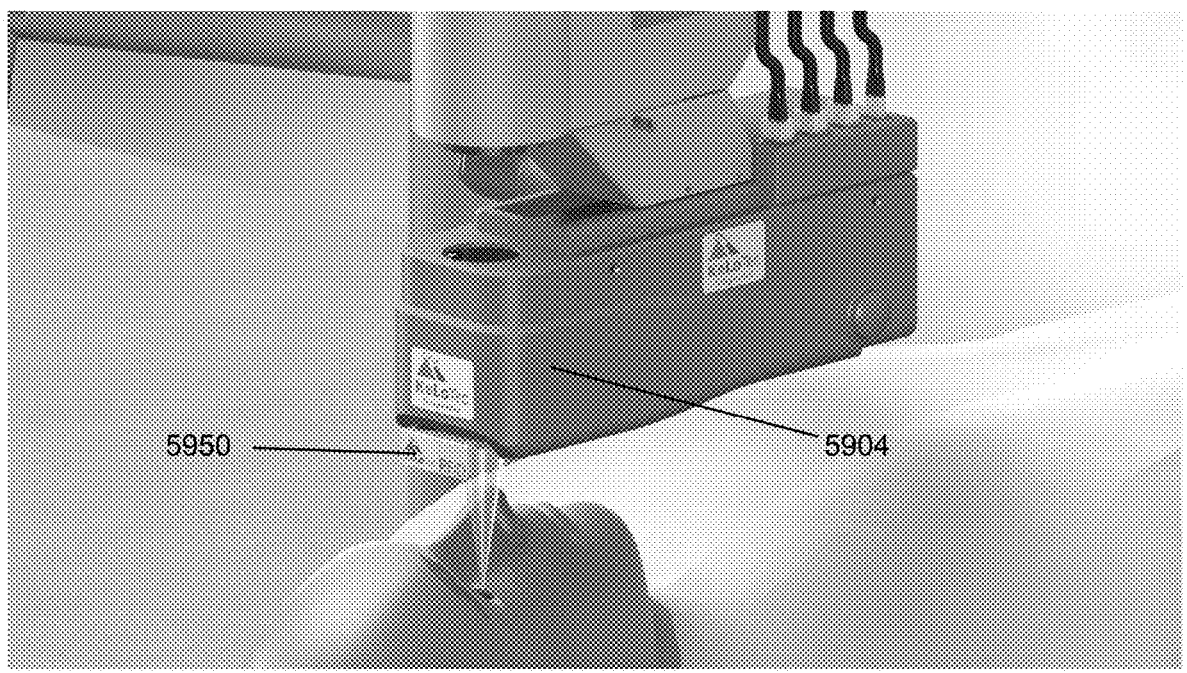
FIG. 50 shows a laser delivery system with an RFID card installed.

FIG. 50 shows a laser delivery system 5904 with an RFID card 5950 installed.

Figure 51:
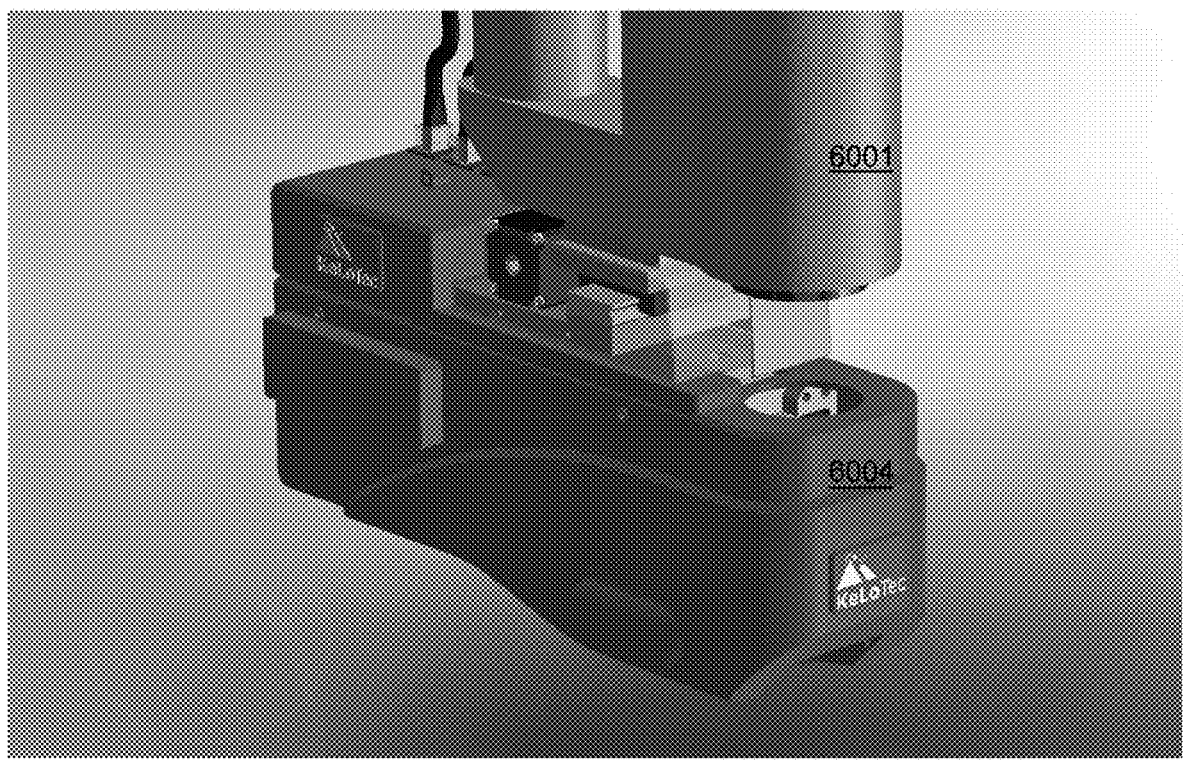
FIG. 51 shows a laser delivery system installed under a microscope.

FIG. 51 shows a laser delivery system 6004 installed under a microscope 6001.

FIG. 52 shows a laser delivery system 6204 in the "in" position under the microscope 6201.

FIG. 53 shows a laser delivery system 6204 in the "out" position under the microscope 6201.

FIG. 54 shows an eye with a patient interface attached to it.

FIG. 55 shows an eye with a patient interface attached to it.

FIG. 56 shows an eye with a patient interface attached to it.

FIG. 57 shows an eye with a patient interface attached to it.

FIG. 58 shows a patient eye under a delivery system prior to docking.

FIG. 59 shows a patient eye under a delivery system after docking.

FIG. 60 Optical cross section of a laser delivery system.

FIG. 61 Exploded component view of a laser delivery system.

FIG. 62 Shows an adjustable diameter offset rotatable lens mount in its 0 offset and maximum offset position.

FIG. 63 Shows an exploded view of an adjustable diameter offset rotatable lens mount.

What is claimed is:

1. A system for eye surgery, comprising:
a femtosecond laser delivery apparatus to cut a tissue structure of an eye with a sequence of multiple laser pulses creating micro cavitation bubbles; the femtosecond laser delivery apparatus comprising a laser engine and a laser delivery system, the laser engine and the laser delivery system in optical communication;
an optical microscope having a bottom side;
the laser delivery system in direct contact with and adjacent to the bottom side of the optical microscope; wherein the laser delivery system is in sliding engagement with the optical microscope;
whereby the laser delivery system is configured for sliding movement from a first position to a second position;
wherein the first position defines an in position and the second position defines an out position and;
wherein the laser delivery system remains adjacent to and in direct contact with the optical microscope in the first position and in the second position.

2. A system for eye surgery, comprising:
a laser delivery apparatus configured to cut a tissue structure of an eye with a sequence of multiple laser pulses; the laser delivery apparatus comprising a laser engine in optical communication with a laser delivery system;
an optical microscope integral with and directly adjacent to the laser delivery system;
wherein the optical microscope and the laser delivery system have a common support attached to a housing of the laser delivery system and the optical microscope; and,
the common support is configured to only provide horizontal movement; and is configured to move the laser delivery system in a horizontal direction from a first position to a second position;
wherein the first position defines an in position and the second position defines an out position, wherein the first position is horizontally spaced apart from the second position.

3. The system of claim 2, wherein the laser delivery system is a femtosecond laser delivery system.

4. A system for eye surgery, comprising:
an integrated phacoemulsification device, an optical microscope a laser engine and a laser delivery system in optical communication with the laser engine, and the laser engine and laser delivery system configured to deliver a laser beam to cut a tissue structure of an eye with a sequence of multiple laser pulses;
a bottom of the optical microscope directly attached to the laser delivery system, thereby forming the only attachment between the optical microscope and the laser delivery system; and,
whereby the system is configured to move the laser delivery system relative to the optical microscope only in a horizontal direction; wherein the system is configured to move the laser delivery system from a first position to a second position;
wherein the first position defines an in position and the second position defines an out position, wherein the first position is horizontally spaced apart from the second position.

5. The system of claim 4, wherein the laser engine is a femtosecond laser.

6. The system of claim 1, wherein the first position is horizontally spaced from the second position.

7. The system of claim 1, wherein the first position is horizontally spaced from the second position along a y-axis, the y-axis corresponding to a length of the laser delivery system.

8. The system of claim 7, wherein the system is configured for movement of the laser delivery system in an x-direction while in the in position.

9. The system of claim 2, wherein the laser delivery system remains directly adjacent to the optical microscope in first position and in the second position.

10. The system of claim 2, wherein the first position is horizontally spaced from the second position along a y-axis, the y-axis corresponding to a length of the laser delivery system.

11. The system of claim 10, wherein the system is configured for movement of the laser delivery system in an x-direction while in the in position.

12. The system of claim 1, 6, 7, or 8, comprising a motor and a side assembly.

13. The system of claim 1, 6, 7, or 8, wherein the laser delivery system comprises a motor and a side assembly positioned on a top side of the laser delivery system and attached to the bottom side of the optical microscope.

14. The system of claim 1, 6, 7, or 8, wherein the laser delivery system comprises a motor and a side assembly positioned on a top side of the laser delivery system and attached to a mounting positioned on the bottom side of the optical microscope.

15. The system of claim 2, 9, 10, or 11, wherein the common support comprises a motor and a side assembly positioned on a top side of the laser delivery system and positioned on a bottom side of the optical microscope.

16. The system of claim 2, 9, 10, or 11, wherein the common support comprises a motor, a side assembly positioned on a top side of the laser delivery system and a mounting positioned on a bottom side of the optical microscope.

17. The system of claim 4, wherein the first position is horizontally spaced from the second position along a y-axis, the y-axis corresponding to a length of the laser delivery system.

18. The system of claim 17, wherein the system is configured for movement of the laser delivery system in an x-direction while in the in position.

19. The system of claim 4, comprising a slide, a motor and a mounting.

20. The system of claim 1, 2, 4, 6, 7, or 9, wherein in the out position the system is configured to provide full access to an eye for the use of a phaco hand piece.

21. The system of claim 1, 2, 4, 6, 7, or 9, further comprising a slide, a motor and a mounting; and wherein in the out position the system is configured to provide full access to an eye for the use of a phaco hand piece.

22. The system of claim 1, 2, or 4, wherein the laser engine is directly attached to and adjacent the optical microscope.

23. The system of claim 1, 2, or 4, wherein the laser delivery system comprises a heads up module.

24. The system of claim 1, 2, or 4, wherein the laser delivery system comprises a diagnostic module.

* * * * *